(12) United States Patent
Ihle et al.

(10) Patent No.: US 8,580,812 B2
(45) Date of Patent: Nov. 12, 2013

(54) HETEROARYL AMIDE ANALOGUES AS P2X$_7$ ANTAGONISTS

(75) Inventors: David C. Ihle, Worcester, MA (US); Qin Guo, Waterford, CT (US); Kevin Hodgetts, Waterford, CT (US); Jun Yuan, Boston, MA (US)

(73) Assignee: H. Lundbeck A/S, Valby (DK)

(*) Notice: Subject to any disclaimer, the term of this patent is extended or adjusted under 35 U.S.C. 154(b) by 442 days.

(21) Appl. No.: 12/595,394

(22) PCT Filed: Apr. 9, 2008

(86) PCT No.: PCT/US2008/004563
§ 371 (c)(1),
(2), (4) Date: Jun. 28, 2010

(87) PCT Pub. No.: WO2008/124153
PCT Pub. Date: Oct. 16, 2008

(65) Prior Publication Data
US 2010/0266509 A1    Oct. 21, 2010

Related U.S. Application Data

(60) Provisional application No. 60/910,864, filed on Apr. 10, 2007.

(51) Int. Cl.
| | | |
|---|---|---|
| C07D 221/02 | (2006.01) | |
| C07D 491/02 | (2006.01) | |
| C07D 498/02 | (2006.01) | |
| A01N 43/42 | (2006.01) | |
| A61K 31/44 | (2006.01) | |

(52) U.S. Cl.
USPC ............ 514/299; 544/300; 546/112; 546/121

(58) Field of Classification Search
USPC ......................... 546/112, 121; 514/299, 300
See application file for complete search history.

(56) References Cited

U.S. PATENT DOCUMENTS

| | | | |
|---|---|---|---|
| 5,260,303 A * | 11/1993 | Becker et al. ............. | 514/30 |
| 5,707,997 A | 1/1998 | Shoji et al. | |
| 6,355,653 B1 | 3/2002 | Trottmann et al. | |
| 6,730,789 B1 | 5/2004 | Birault et al. | |
| 7,078,405 B2 | 7/2006 | Hibi et al. | |
| 7,091,215 B2 | 8/2006 | Hibi et al. | |
| 7,144,907 B2 | 12/2006 | Wallace et al. | |
| 7,230,099 B2 | 6/2007 | Wallace et al. | |
| 7,285,666 B2 | 10/2007 | Hibi et al. | |
| 7,491,821 B2 | 2/2009 | Brotherton-Pleiss et al. | |
| 7,538,120 B2 | 5/2009 | Koch et al. | |
| 7,578,855 B2 | 8/2009 | Fadli | |
| 2005/0049419 A1 | 3/2005 | Wallace et al. | |
| 2005/0054701 A1 | 3/2005 | Wallace et al. | |
| 2006/0030610 A1 | 2/2006 | Koch et al. | |
| 2006/0217448 A1 | 9/2006 | Kelly et al. | |
| 2008/0039478 A1 | 2/2008 | Kelly et al. | |
| 2008/0108648 A1 | 5/2008 | Alcouffe et al. | |
| 2010/0216763 A1 | 8/2010 | Hutchison et al. | |

FOREIGN PATENT DOCUMENTS

| | | |
|---|---|---|
| EP | 1277754 B1 | 7/2005 |
| JP | 9202786 A | 8/1997 |
| JP | 2004002826 | 1/2004 |
| WO | 9929660 A1 | 6/1999 |
| WO | 9929661 A1 | 6/1999 |
| WO | 0117999 A2 | 3/2001 |
| WO | 0194338 A1 | 12/2001 |
| WO | 02066478 A1 | 8/2002 |
| WO | 03035649 A1 | 5/2003 |
| WO | 03041707 A1 | 5/2003 |
| WO | 03078435 A1 | 9/2003 |
| WO | 03080579 A1 | 10/2003 |
| WO | 2004021984 A2 | 3/2004 |
| WO | 2004033454 A1 | 4/2004 |
| WO | 2004/106305 A | 12/2004 |
| WO | 2004108722 A1 | 12/2004 |
| WO | 2005014529 A1 | 2/2005 |
| WO | 2005089763 A1 | 9/2005 |
| WO | 2006025783 A1 | 3/2006 |

(Continued)

OTHER PUBLICATIONS

Abe et al., Journal of Medicinal Chemistry (1998), 41(4), 564-578.*
3. Sigova, V. I. et al, (1985) "Synthesis and biological activity of the aryl amides of 2-methylnicotinic and 2-phenylindolisine-8-carboxylic acids";Khimiko-Farmatsevticheskii Zhurnal, 19(3): 159-63, (STN Database No. 1985: 453910; XP002486879).

(Continued)

*Primary Examiner* — Niloofar Rahmani
(74) *Attorney, Agent, or Firm* — Kitae Lim

(57) ABSTRACT

Heteroaryl amide analogues are provided, of Formula (I), wherein variables are as described herein. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using such compounds to treat such disorders are provided, as are methods for using such ligands for receptor localization studies.

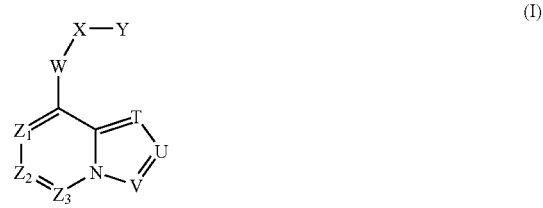

(I)

26 Claims, No Drawings

(56) References Cited

FOREIGN PATENT DOCUMENTS

| | | |
|---|---|---|
| WO | 2006038116 A2 | 4/2006 |
| WO | 2006/102588 A | 9/2006 |
| WO | 2006094235 A1 | 9/2006 |
| WO | 2006097625 A1 | 9/2006 |
| WO | 2006101455 A1 | 9/2006 |
| WO | 2006102610 A2 | 9/2006 |
| WO | 2006/110516 A | 10/2006 |
| WO | 2007027999 A2 | 3/2007 |
| WO | 2007087548 A2 | 8/2007 |
| WO | 2007087549 A2 | 8/2007 |
| WO | 2007113226 A1 | 10/2007 |
| WO | 2008019309 A1 | 2/2008 |
| WO | 2008/026687 A | 3/2008 |
| WO | 2008045688 A1 | 4/2008 |

OTHER PUBLICATIONS

Honore, P. et al. Sep. 18, 2006. A-740003 )N-(1{[(cyanoimino)(5-quinolinylamino) methyl]amino}-2,2-dimethylpropyl)-2-(3,4-dimethoxyphenyl)acetamide, A Novel and Selective P2X7 Receptor Antagonist Dose-Dependently Reduces Neuropathic Pain in the Rat. JPET 319(2): 1376-1385.

Nelson, D.W. et al. 2006. Structure-Activity Relationship Studies on a Series of Novel, Substituted 1-Benzyl-5-phenyltetrazole P2X7 Antagonists, J. Med. Chem. 49:3659-3666.

Seman et al. Oct. 2003. NAD-Induced T Cell Death: ADP-Ribosylation of Cell Surface Proteins by ART Activates the Cytolytic P2X7 Purinoceptor. Immunity 19:571-582.

Japanese Office Action issued Apr. 25, 2013 in Japanese Application No. 2010-503041 (with English Translation).

* cited by examiner

HETEROARYL AMIDE ANALOGUES AS P2X₇ ANTAGONISTS

CROSS-REFERENCE TO RELATED APPLICATIONS

The present application is a §371 U.S. National Stage Application of International Application No. PCT/US2008/04563, filed Apr. 9, 2008, which claims the benefit of priority of U.S. Provisional Application No. 60/910,864, filed Apr. 10, 2007. Each of these applications is hereby incorporated by reference in its entirety.

FIELD OF THE INVENTION

This invention relates generally to heteroaryl amide analogues that have useful pharmacological properties. The invention further relates to the use of such compounds for treating conditions related to $P2X_7$ receptor activation, for identifying other agents that bind to $P2X_7$ receptor, and as probes for the detection and localization of $P2X_7$ receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain, which typically results from damage to the nervous system, involves pain signal transmission in the absence of stimulus, pain from a normally innocuous stimulus (allodynia) and increased pain from a normally painful stimulus (hyperalgesia). In most instances, neuropathic pain is thought to occur because of sensitization in the peripheral and central nervous systems following initial damage to the peripheral nervous system (e.g., via direct injury or systemic disease). Neuropathic pain is typically burning, shooting and unrelenting in its intensity and can sometimes be more debilitating than the initial injury or disease process that induced it.

Existing treatments for neuropathic pain are generally suboptimal. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens, or to treatment with other drugs, such as gabapentin. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Another common condition for which existing therapies are insufficient or problematic is inflammation. Transient inflammation is a beneficial mechanism that protects mammals from invading pathogens. Uncontrolled inflammation, however, causes tissue damage and pain and is the underlying cause of many illnesses, including asthma, as well as other allergic, infectious, autoimmune, degenerative, and idiopathic diseases. Existing treatments often exhibit low, delayed or only temporary efficacy, undesirable side-effects and/or a lack of selectivity. There is a continuing need for new drugs that overcome one or more of the shortcomings of drugs currently used for immunosuppression or in the treatment or prevention of inflammatory disorders, including allergic disorders, autoimmune disorders, fibrogenic disorders, and neurodegenerative diseases, such as multiple sclerosis, amyotrophic lateral sclerosis, Alzheimer's disease, and Huntington's disease.

$P2X_7$ receptor ("$P2X_7$") is a ligand-gated ion channel that is activated by ATP and is present on a variety of cell types, including microglia in the central nervous system and cells involved in inflammation and immune system function. In particular, $P2X_7$ is involved in activation of lymphocytes and monocyte/macrophages leading to the increased release of pro-inflammatory cytokines (e.g., TNFalpha and IL-1beta) from these cells. Recent studies indicate that inhibiting $P2X_7$ activation in situations of inflammation (e.g., rheumatoid arthritis and other autoimmune diseases, osteoarthritis, uveitis, asthma, chronic obstructive pulmonary disease and inflammatory bowel disease) or interstitial fibrosis results in a therapeutic effect. These and other studies indicate that $P2X_7$ antagonists may find use in the treatment and prophylaxis of pain, including acute, chronic and neuropathic pain, as well as a variety of other conditions including osteoarthritis, rheumatoid arthritis, arthrosclerosis, inflammatory bowel disease, Alzheimer's disease, traumatic brain injury, asthma, chronic obstructive pulmonary disease, and fibrosis of internal organs (e.g., interstitial fibrosis).

Small molecule $P2X_7$ antagonists are desirable for such therapies. The present invention fulfills this need, and provides further related advantages.

SUMMARY OF THE INVENTION

The present invention provides heteroaryl amide analogues of Formula I:

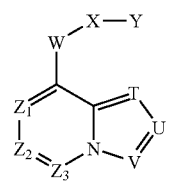

Formula I as well as pharmaceutically acceptable salts of such compounds.

Within Formula I:

T, U and V are independently chosen from $CR_3$, $CR_4$ and N; in certain embodiments, exactly one of T, U and V is $CR_4$;

W is —C(=O)NR₄—, —NR₄C(=O)— or —NR₄—NR₄—C(=O)—;

X is absent or $C_1$-$C_6$alkylene that is substituted with from 0 to 4 substituents independently chosen from: (i) $C_1$-$C_4$alkyl, ($C_3$-$C_8$cycloalkyl)$C_0$-$C_2$alkyl and phenyl$C_0$-$C_2$alkyl; (ii) substituents that are taken together to form a 3- to 7-membered cycloalkyl or heterocycloalkyl ring; and (iii) substituents that are taken together with $R_4$ to form a 4- to 7-membered heterocycloalkyl;

Y is $C_1$-$C_8$alkyl, $C_3$-$C_{16}$cycloalkyl, 4- to 16-membered heterocycloalkyl, 6- to 16-membered aryl or 5- to 16-membered heteroaryl, each of which is optionally substituted and each of which is preferably substituted with from 0 to 6 substituents independently chosen from hydroxy, halogen, cyano, amino, nitro, oxo, aminocarbonyl, aminosulfonyl, COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$-aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$Z_1$ and $Z_3$ are independently N, CH or substituted carbon (e.g., $CR_2$);

$Z_2$ is N, CH or substituted carbon (e.g., $CR_A$ or $CR_2$);

Each $R_2$ and each $R_3$ is independently chosen from hydrogen, halogen, cyano, amino, nitro, aminocarbonyl, aminosulfonyl, COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$-aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

Each $R_4$ is independently hydrogen, $C_1$-$C_6$alkyl, ($C_3$-$C_8$cycloalkyl)$C_0$-$C_2$alkyl or taken together with a substituent of X to form a 4- to 7-membered heterocycloalkyl; and $R_A$ is a group of the formula -L-A-M, wherein:

L is absent or $C_1$-$C_6$alkylene that is optionally modified by the replacement of a carbon-carbon single bond with a double or triple carbon-carbon bond, which alkylene is optionally substituted with oxo or an acidic moiety such as —COOH, —SO$_3$H, —SO$_2$NH$_2$, —PO$_3$H$_2$, tetrazole or oxadizaolone;

A is absent or CO, O, NR$_6$, S, SO, SO$_2$, CONR$_6$, NR$_6$CO, ($C_4$-$C_7$cycloalkyl)$C_0$-$C_4$alkylene or (4- to 7-membered heterocycloalkyl)$C_0$-$C_4$alkylene; wherein $R_6$ is hydrogen or $C_1$-$C_6$alkyl; and M is:
(i) hydroxy, cyano, amino, aminocarbonyl, aminosulfonyl or COOH; or
(ii) $C_1$-$C_6$haloalkyl, $C_1$-$C_6$alkoxy, 5- to 10-membered carbocycle, 4- to 10-membered heterocycle, $C_1$-$C_6$alkanoyloxy, $C_1$-$C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is optionally substituted and each of which is preferably substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

Within certain aspects, Y is $C_3$-$C_{16}$cycloalkyl, 4- to 16-membered heterocycloalkyl, 6- to 16-membered aryl or 5- to 16-membered heteroaryl, each of which is substituted with from 0 to 6 substituents independently chosen from hydroxy, halogen, cyano, amino, nitro, oxo, aminocarbonyl, aminosulfonyl, COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$-aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

Within certain aspects, heteroaryl amide analogues of Formula I are P2X$_7$ antagonists with an IC$_{50}$ value no greater than 20 micromolar, 10 micromolar, 5 micromolar, 1 micromolar, 500 nanomolar or 100 nanomolar in an in vitro assay for determination of P2X$_7$ antagonist activity. In certain embodiments, such P2X$_7$ antagonists exhibit no detectable agonist activity in an in vitro assay of P2X$_7$ activity (i.e., in an assay provided in Example 4, herein) at a concentration equal to the IC$_{50}$, 10 times the IC$_{50}$ or 100 times the IC$_{50}$ and/or at a concentration of 2,500 nM.

Within certain aspects, heteroaryl amide analogues provided herein are labeled with a detectable marker (e.g., radio-labeled or fluorescein conjugated).

The present invention further provides, within other aspects, pharmaceutical compositions comprising at least one heteroaryl amide analogue provided herein in combination with a physiologically acceptable carrier or excipient.

Within further aspects, methods are provided for modulating (e.g., reducing) cellular P2X$_7$ activation or activity, comprising contacting a cell (e.g., microglia, astrocyte or peripheral macrophage or monocyte) that expresses a P2X$_7$ with at least one P2X$_7$ modulator as described herein. Such contact may occur in vivo or in vitro and is generally performed using a concentration of P2X$_7$ modulator that is sufficient to detectably alter P2X$_7$ activity in vitro (as determined using an assay provided in Example 4).

The present invention further provides methods for treating a condition responsive to P2X$_7$ modulation in a patient, comprising administering to the patient a therapeutically effective amount of at least one P2X$_7$ antagonist as described herein.

Within other aspects, methods are provided for treating pain in a patient, comprising administering to a patient suffering from (or at risk for) pain a therapeutically effective amount of at least one P2X$_7$ antagonist as described herein.

Within other aspects, methods are provided for treating inflammation in a patient, comprising administering to a patient suffering from (or at risk for) inflammation a therapeutically effective amount of at least one P2X$_7$ antagonist as described herein.

Methods are further provided for treating osteoarthritis, rheumatoid arthritis, arthrosclerosis, inflammatory bowel disease, Alzheimer's disease, traumatic brain injury, asthma, chronic obstructive pulmonary disease, ocular conditions (e.g., glaucoma), cirrhosis, lupus, scleroderma, or fibrosis of internal organs (e.g., interstitial fibrosis) in a patient, comprising administering to a patient suffering from (or at risk for) one or more of the foregoing conditions a therapeutically effective amount of at least one P2X$_7$ antagonist as described herein.

Within still further aspects, the present invention provides methods for inhibiting death of retinal ganglion cells in a patient, comprising administering to the patient a therapeutically effective amount of at least one P2X$_7$ antagonist as described herein.

Methods are further provided for identifying an agent that binds to P2X$_7$, comprising: (a) contacting P2X$_7$ with a labeled compound that is a heteroaryl amide analogue as described herein under conditions that permit binding of the compound to P2X$_7$, thereby generating bound, labeled compound; (b) detecting a signal that corresponds to the amount of bound, labeled compound in the absence of test agent; (c) contacting the bound, labeled compound with a test agent; (d) detecting a signal that corresponds to the amount of bound labeled compound in the presence of test agent; and (e)

detecting a decrease in signal detected in step (d), as compared to the signal detected in step (b).

Within further aspects, the present invention provides methods for determining the presence or absence of P2X$_7$ in a sample, comprising: (a) contacting a sample with a compound as described herein under conditions that permit modulation by the compound of P2X$_7$ activity; and (b) detecting a signal indicative of a level of the compound modulating P2X$_7$ activity.

The present invention also provides packaged pharmaceutical preparations, comprising: (a) a pharmaceutical composition as described herein in a container; and (b) instructions for using the composition to (i) treat one or more conditions responsive to P2X$_7$ modulation, such as pain, osteoarthritis, rheumatoid arthritis, arthrosclerosis, inflammatory bowel disease, Alzheimer's disease, traumatic brain injury, asthma, chronic obstructive pulmonary disease, ocular conditions (e.g., glaucoma), cirrhosis, lupus, scleroderma, and/or fibrosis of internal organs (e.g., interstitial fibrosis) or (ii) provide retinal neuroprotection (e.g., inhibit death of retinal ganglion cells).

In yet another aspect, the present invention provides methods for preparing the compounds disclosed herein, including the intermediates.

These and other aspects of the invention will become apparent upon reference to the following detailed description.

DETAILED DESCRIPTION

As noted above, the present invention provides heteroaryl amide analogues. Such compounds may be used in vitro or in vivo, to modulate P2X$_7$ activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, A, X). Unless otherwise specified, each variable within such a formula is defined independently of any other variable, and any variable that occurs more than one time in a formula is defined independently at each occurrence.

The phrase "heteroaryl amide analogue," as used herein, encompasses all compounds of Formula I, as well as compounds of other Formulas provided herein (including any enantiomers, racemates and stereoisomers) and pharmaceutically acceptable salts thereof. In certain embodiments, substituted pyrimidinones provided herein are isolated so as to be substantially free of residual organic solvent (i.e., any such solvent in the preparation is present in an amount that is at or below the limit set for that solvent by the International Council on Harmonisation of Technical Requirements for Registration of Pharmaceuticals for Human Use (ICH)).

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutically acceptable anions for use in salt formation include, but are not limited to, acetate, 2-acetoxybenzoate, ascorbate, benzoate, bicarbonate, bromide, calcium edetate, carbonate, chloride, citrate, dihydrochloride, diphosphate, ditartrate, edetate, estolate (ethylsuccinate), formate, fumarate, gluceptate, gluconate, glutamate, glycolate, glycollylarsanilate, hexylresorcinate, hydrabamine, hydrobromide, hydrochloride, hydroiodide, hydroxymaleate, hydroxynaphthoate, iodide, isethionate, lactate, lactobionate, malate, maleate, mandelate, methylbromide, methylnitrate, methylsulfate, mucate, napsylate, nitrate, pamoate, pantothenate, phenylacetate, phosphate, polygalacturonate, propionate, salicylate, stearate, subacetate, succinate, sulfamate, sulfanilate, sulfate, sulfonates including besylate (benzenesulfonate), camsylate (camphorsulfonate), edisylate (ethane-1,2-disulfonate), esylate (ethanesulfonate) 2-hydroxyethylsulfonate, mesylate (methanesulfonate), triflate (trifluoromethanesulfonate) and tosylate (p-toluenesulfonate), tannate, tartrate, teoclate and triethiodide. Similarly, pharmaceutically acceptable cations for use in salt formation include, but are not limited to ammonium, benzathine, chloroprocaine, choline, diethanolamine, ethylenediamine, meglumine, procaine, and metals such as aluminum, calcium, lithium, magnesium, potassium, sodium and zinc. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, methanol, isopropanol or acetonitrile, is preferred.

It will be apparent that compounds and salts thereof provided herein may, but need not, be formulated as a hydrate, and that such hydrates are encompassed by the formulas, names and structures recited herein. In addition, the various non-hydrate solvates, non-covalent complexes, crystal forms and polymorphs of the compounds provided herein are within the scope of the present invention. Also provided herein are prodrugs of the compounds of the recited Formulas. A "prodrug" is a compound that may not fully satisfy the structural requirements of the compounds provided herein, but is modified in vivo, following administration to a patient, to produce a compound of a formula provided herein. For example, a prodrug may be an acylated derivative of such a compound. Prodrugs include compounds wherein hydroxy, amine or sulfhydryl groups are bonded to any group that, when administered to a mammalian subject, cleaves to form a free hydroxy, amino or sulfhydryl group, respectively. Examples of prodrugs include, but are not limited to, acetate, formate, benzoate and peptide derivatives of alcohol and amine functional groups within a compound provided herein. Prodrugs may generally be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group. In some instances, a substituent of an alkyl group is specifically indicated. For example, "$C_1$-$C_6$hydroxyalkyl" is a $C_1$-$C_6$alkyl group substituted with at least one —OH; "$C_1$-$C_6$aminoalkyl" is a $C_1$-$C_6$alkyl group substituted with at least one —NH$_2$; $C_1$-$C_6$cyanoalkyl is a $C_1$-$C_6$alkyl group substituted with at least one —CN.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "$C_2$-$C_6$cyanoalkenyl" is a $C_2$-$C_6$alkenyl group substituted with at least one —CN.

"Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

"Alkylene" refers to a divalent alkyl group, as defined above. $C_1$-$C_2$alkylene is methylene or ethylene; $C_0$-$C_4$alkylene is a single covalent bond or an alkylene group having 1, 2, 3 or carbon atoms; $C_0$-$C_2$alkylene is a single covalent bond, methylene or ethylene. A "$C_1$-$C_6$alkylene that is optionally modified by the replacement of a carbon-carbon single bond with a double or triple carbon-carbon bond" is a $C_1$-$C_6$alkylene group as described above, or a divalent $C_2$-$C_6$alkene or $C_2$-$C_6$alkyne.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, myrtanyl and partially saturated variants of the foregoing, such as cyclohexenyl. Cycloalkyl groups do not comprise an aromatic ring or a heterocyclic ring. Certain cycloalkyl groups are $C_3$-$C_7$cycloalkyl, in which the cycloalkyl group contains a single ring having from 3 to 7 ring members, all of which are carbon. A "($C_3$-$C_7$cycloalkyl)$C_0$-$C_4$alkyl" is a $C_3$-$C_7$cycloalkyl group linked via a single covalent bond or a $C_1$-$C_4$alkylene group.

A "($C_4$-$C_7$cycloalkyl)$C_0$-$C_4$alkylene" is a divalent ($C_3$-$C_7$cycloalkyl)$C_0$-$C_4$alkyl group that is linked via two single covalent bonds to two specified moieties. In general, one single covalent bond is located on the cyclic portion and the other is located on the alkylene portion, if present; alternatively, if no alkylene group is present, both single covalent bonds are on different ring members. For example, with respect to the group $R_4$, if A is ($C_6$cycloalkyl)$C_2$alkylene and M is COOH, one $R_A$ moiety so formed is:

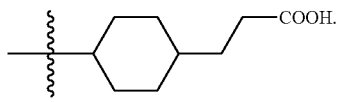

By "alkoxy," as used herein, is meant an alkyl group as described above attached via an oxygen bridge. Alkoxy groups include $C_1$-$C_6$alkoxy and $C_1$-$C_4$alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "oxo" is used herein to refer to an oxygen substituent of a carbon atom that results in the formation of a carbonyl group (C=O). An oxo group that is a substituent of a nonaromatic carbon atom results in a conversion of —CH$_2$— to —C(=O)—. An oxo group that is a substituent of an aromatic carbon atom results in a conversion of —CH— to —C(=O)— and may result in a loss of aromaticity.

The term "alkanoyl" refers to an acyl group (e.g., —(C=O)-alkyl), in which carbon atoms are in a linear or branched alkyl arrangement and where attachment is through the carbon of the keto group. Alkanoyl groups have the indicated number of carbon atoms, with the carbon of the keto group being included in the numbered carbon atoms. For example a $C_2$alkanoyl group is —(C=O)CH$_3$. Alkanoyl groups include, for example, $C_2$-$C_8$alkanoyl, $C_2$-$C_6$alkanoyl and $C_2$-$C_4$alkanoyl groups, which have from 2 to 8, from 2 to 6 or from 2 to 4 carbon atoms, respectively. "$C_1$alkanoyl" refers to —(C=O)H, which (along with $C_2$-$C_8$alkanoyl) is encompassed by the term "$C_1$-$C_8$alkanoyl."

"Alkyl ether" refers to a linear or branched ether substituent (i.e., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$ alkyl ether substituent is —CH$_2$—O—CH$_3$.

The term "alkoxycarbonyl" refers to an alkoxy group attached through a keto (—(C=O)—) bridge (i.e., a group having the general structure —C(=O)—O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group (i.e., the carbon of the keto bridge is not included in the indicated number of carbon atoms). "$C_1$alkoxycarbonyl" refers to —C(=O)—O—CH$_3$; $C_3$alkoxycarbonyl indicates —C(=O)—O—(CH$_2$)$_2$CH$_3$ or —C(=O)—O—(CH)(CH$_3$)$_2$.

"Alkanoyloxy," as used herein, refers to an alkanoyl group linked via an oxygen bridge (i.e., a group having the general structure —O—C(=O)-alkyl). Alkanoyloxy groups include $C_1$-$C_8$, $C_1$-$C_6$ and $C_1$-$C_4$alkanoyloxy groups, which have from 1 to 8, 6 or 4 carbon atoms, respectively, in the alkyl portion of the group. For example, "$C_1$alkanoyloxy" refers to —O—C(=O)—CH$_3$.

Similarly, "alkanoylamino," as used herein, refers to an alkanoyl group linked via a nitrogen bridge (i.e., a group having the general structure —N(R)—C(=O)-alkyl), in which R is hydrogen or $C_1$-$C_6$alkyl. Alkanoylamino groups include $C_1$-$C_8$, $C_1$-$C_6$ and $C_1$-$C_4$alkanoylamino groups, which have from 1 to 8, 6 or 4 carbon atoms within the alkanoyl group, respectively, in the alkyl portion of the group.

"Alkylsulfonyl" refers to groups of the formula —(SO$_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or from 1 to 4 carbon atoms, respectively. Methylsulfonyl is one representative alkylsulfonyl group. "$C_1$-$C_4$haloalkylsulfonyl" is an alkylsulfonyl group that has from 1 to 4 carbon atoms and is substituted with at least one halogen (e.g., trifluoromethylsulfonyl).

"Alkylsulfonylamino" refers to groups of the formula —N(R)—(SO$_2$)-alkyl, in which R is hydrogen or $C_1$-$C_6$alkyl and the nitrogen atom is the point of attachment. Alkylsulfonylamino groups include $C_1$-$C_6$alkylsulfonylamino and $C_1$-$C_4$alkylsulfonylamino groups, which have from 1 to 6 or 1 to 4 carbon atoms, respectively. Methylsulfonylamino is a representative alkylsulfonylamino group. "$C_1$-$C_6$haloalkylsulfonylamino" is an alkylsulfonylamino group that has from 1 to 6 carbon atoms and is substituted with at least one halogen (e.g., trifluoromethylsulfonylamino).

"Aminosulfonyl" refers to groups of the formula —(SO$_2$)—NH$_2$, in which the sulfur atom is the point of attachment. The term "mono- or di-(C$_1$-C$_6$alkyl)aminosulfonyl" refers to groups that satisfy the formula —(SO$_2$)—NR$_2$, in which the sulfur atom is the point of attachment, and in which one R is C$_1$-C$_6$alkyl and the other R is hydrogen or an independently chosen C$_1$-C$_6$alkyl.

"Alkylaminoalkyl" refers to an alkylamino group linked via an alkylene group (i.e., a group having the general structure -alkylene-NH-alkyl or -alkylene-N(alkyl)(alkyl)) in which each alkyl is selected independently from alkyl, cycloalkyl and (cycloalkyl)alkyl groups. Alkylaminoalkyl groups include, for example, mono- and di-(C$_1$-C$_8$alkyl)aminoC$_1$-C$_8$ alkyl, mono- and di-(C$_1$-C$_6$alkyl)aminoC$_1$-C$_6$alkyl and mono- and di-(C$_1$-C$_6$alkyl)aminoC$_1$-C$_4$alkyl. "Mono- or di-(C$_1$-C$_6$alkyl)aminoC$_0$-C$_6$alkyl" refers to a mono- or di-(C$_1$-C$_6$alkyl)amino group linked via a single covalent bond or a C$_1$-C$_6$alkylene group. The following are representative alkylaminoalkyl groups:

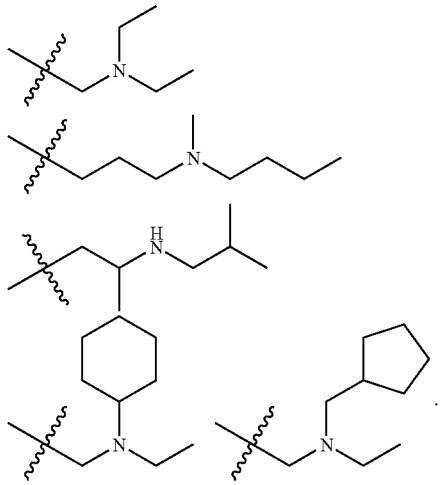

It will be apparent that the definition of "alkyl" as used in the terms "alkylamino" and "alkylaminoalkyl" differs from the definition of "alkyl" used for all other alkyl-containing groups, in the inclusion of cycloalkyl and (cycloalkyl)alkyl groups (e.g., (C$_3$-C$_7$cyclo alkyl)C$_0$-C$_6$alkyl).

The term "aminocarbonyl" refers to an amide group (i.e., —(C=O)NH$_2$). "Mono- or di-(C$_1$-C$_6$alkyl)aminocarbonyl" refers to groups of the formula —(C=O)—N(R)$_2$, in which the carbonyl is the point of attachment, one R is C$_1$-C$_6$alkyl and the other R is hydrogen or an independently chosen C$_1$-C$_6$alkyl.

"Mono- or di-(C$_1$-C$_6$alkyl)aminocarbonylC$_0$-C$_4$alkyl" is an aminocarbonyl group in which one or both of the hydrogen atoms is replaced with C$_1$-C$_6$alkyl, and which is linked via a single covalent bond (i.e., mono- or di-(C$_1$-C$_6$alkyl)aminocarbonyl) or a C$_1$-C$_4$alkylene group (i.e., —(C$_0$-C$_4$alkyl)-(C=O)N(C$_1$-C$_6$alkyl)$_2$). If both hydrogen atoms are so replaced, the C$_1$-C$_6$alkyl groups may be the same or different.

The term "aminosulfonyl" refers to a sulfonamide group (i.e., —(SO$_2$)NH$_2$). "Mono- or di-(C$_1$-C$_8$alkyl)aminosulfonyl" refers to groups of the formula —(SO$_2$)—N(R)$_2$, in which the sulfur atom is the point of attachment, one R is C$_1$-C$_8$alkyl and the other R is hydrogen or an independently chosen C$_1$-C$_8$alkyl.

"Mono- or di-(C$_1$-C$_6$alkyl)aminosulfonylC$_0$-C$_4$alkyl" is an aminosulfonyl group in which one or both of the hydrogen atoms is replaced with C$_1$-C$_6$alkyl, and which is linked via a single covalent bond (i.e., mono- or di-(C$_1$-C$_6$alkyl)aminosulfonyl) or a C$_1$-C$_4$alkylene group (i.e., —(C$_1$-C$_4$alkyl)-(SO$_2$)N(C$_1$-C$_6$alkyl)$_2$). If both hydrogen atoms are so replaced, the C$_1$-C$_6$alkyl groups may be the same or different.

The term "halogen" refers to fluorine, chlorine, bromine or iodine.

A "haloalkyl" is an alkyl group that is substituted with 1 or more independently chosen halogens (e.g., "C$_1$-C$_6$haloalkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above that is linked via an oxygen bridge.

A dash ("-") that is not between two letters or symbols is used to indicate a point of attachment for a substituent. For example, —CONH$_2$ is attached through the carbon atom.

A "carbocycle" or "carbocyclic group" comprises at least one ring formed entirely by carbon-carbon bonds (referred to herein as a carbocyclic ring), and does not contain a heterocycle. Unless otherwise specified, each ring within a carbocycle may be independently saturated, partially saturated or aromatic, and is optionally substituted as indicated. A carbocycle generally has from 1 to 3 fused, pendant or Spiro rings and optionally further contains one or more alkylene bridges; carbocycles within certain embodiments have one ring or two fused rings. Typically, each ring contains from 3 to 8 ring members (i.e., C$_3$-C$_8$); C$_5$-C$_7$ rings are recited in certain embodiments. Carbocycles comprising fused, pendant or Spiro rings typically contain from 9 to 16 ring members. Certain representative carbocycles are cycloalkyl as described above (e.g., cyclohexyl, cycloheptyl or adamantly). Other carbocycles are aryl (i.e., contain at least one aromatic carbocyclic ring, with or without one or more additional aromatic and/or cycloalkyl rings). Such aryl carbocycles include, for example, phenyl, naphthyl (e.g., 1-naphthyl and 2-naphthyl), fluorenyl, indanyl and 1,2,3,4-tetrahydronaphthyl.

Certain carbocycles recited herein are C$_6$-C$_{10}$arylC$_0$-C$_8$alkyl groups (i.e., groups in which a 6- to 10-membered carbocyclic group comprising at least one aromatic ring is linked via a single covalent bond or a C$_1$-C$_8$alkylene group). Phenyl groups linked via a single covalent bond or C$_1$-C$_2$alkylene group are designated phenylC$_0$-C$_2$alkyl (e.g., benzyl, 1-phenyl-ethyl and 2-phenyl-ethyl).

A "heterocycle" or "heterocyclic group" has from 1 to 3 fused, pendant or Spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or SO$_2$. Unless otherwise specified, a heterocycle may be a heterocycloalkyl group (i.e., each ring is saturated or partially saturated), such as a 4- to 7-membered heterocycloalkyl, which generally comprises 1, 2, 3 or 4 ring atoms that are independently chosen from C, O, N and S; or a heteroaryl group (i.e., at least one ring within the group is aromatic), such as a 5- to 10-membered heteroaryl (which may be monocyclic or bicyclic) or a 6-membered heteroaryl (e.g., pyridyl or pyrimidyl). N-linked heterocyclic groups are linked via a component nitrogen atom.

A "heterocycle$C_0$-$C_4$alkyl" is a heterocyclic group linked via a single covalent bond or $C_1$-$C_4$alkylene group. A "(4- to 7-membered heterocycloalkyl)$C_1$-$C_4$alkyl" is a heterocycloalkyl ring with from 4 to 7 ring members that is linked via a $C_1$-$C_4$alkylene group.

A "(4- to 7-membered heterocycloalkyl)$C_0$-$C_4$alkylene" is a divalent (4- to 7-membered heterocycloalkyl)$C_0$-$C_4$alkyl group that is linked via two single covalent bonds to two specified moieties. In general, one such single covalent bond is located on the cyclic portion and the other is located on the alkylene portion, if present; alternatively, if no alkylene group is present, both such single covalent bonds are located on different ring members. For example, with respect to the group $R_4$, if A is a (piperidinyl)$C_2$alkylene and M is COOH, one $R_4$ moiety so formed is:

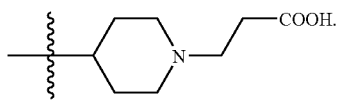 [SMILES: *C1CCN(CCC(=O)O)CC1]

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

The term "$P2X_7$" hereinbelow refers to any $P2X_7$ receptor, preferably a mammalian receptor such as the human or rat $P2X_7$ receptors disclosed in U.S. Pat. No. 6,133,434, as well as homologues thereof found in other species.

A "$P2X_7$ modulator," also referred to herein as a "modulator," is a compound that modulates $P2X_7$ activation and/or $P2X_7$-mediated activity (e.g., signal transduction). $P2X_7$ modulators specifically provided herein are compounds of Formula I and pharmaceutically acceptable salts thereof. A modulator may be a $P2X_7$ agonist or antagonist.

A modulator is considered an "antagonist" if it detectably inhibits $P2X_7$-mediated signal transduction (using, for example, a representative assay provided in Example 4); in general, such an antagonist inhibits $P2X_7$ activation with a $IC_{50}$ value of less than 20 micromolar, preferably less than 10 micromolar, more preferably less than 5 micromolar, more preferably less than 1 micromolar, still more preferably less than 500 nanomolar, and most preferably less than 100 nanomolar within an assay provided in Example 4. $P2X_7$ antagonists include neutral antagonists and inverse agonists.

An "inverse agonist" of $P2X_7$ is a compound that reduces the activity of $P2X_7$ below its basal activity level in the absence of added ligand. Inverse agonists of $P2X_7$ may also inhibit the activity of ligand at $P2X_7$ and/or binding of ligand to $P2X_7$. The basal activity of $P2X_7$, as well as a reduction in $P2X_7$ activity due to the presence of $P2X_7$ antagonist, may be determined from a calcium mobilization assay (e.g., the assay of Example 4).

A "neutral antagonist" of $P2X_7$ is a compound that inhibits the activity of ligand at $P2X_7$, but does not significantly change the basal activity of $P2X_7$ (i.e., within a calcium mobilization assay as described in Example 4 performed in the absence of ligand, $P2X_7$ activity is reduced by no more than 10%, preferably by no more than 5%, and more preferably by no more than 2%; most preferably, there is no detectable reduction in activity). Neutral antagonists of $P2X_7$ may inhibit the binding of ligand to $P2X_7$.

As used herein a "$P2X_7$ agonist" is a compound that elevates the activity of the $P2X_7$ above the basal activity level of $P2X_7$ (i.e., enhances $P2X_7$ activation and/or $P2X_7$-mediated activity, such as signal transduction). $P2X_7$ agonist activity may be detected using the representative assay provided in Example 4. $P2X_7$ agonists include ATP and 2'(3')-O-(4-benzoyl-benzoyl)adenosine 5'-triphosephate (BzATP).

A "therapeutically effective amount" (or dose) is an amount that, upon administration to a patient, results in a discernible patient benefit (e.g., provides detectable relief from at least one condition being treated). Such relief may be detected using any appropriate criteria, including alleviation of one or more symptoms such as pain. A therapeutically effective amount or dose generally results in a concentration of compound in a body fluid (such as blood, plasma, serum, CSF, synovial fluid, lymph, cellular interstitial fluid, tears or urine) that is sufficient to alter $P2X_7$-mediated signal transduction (using an assay provided in Example 4). It will be apparent that the discernible patient benefit may be apparent after administration of a single dose, or may become apparent following repeated administration of the therapeutically effective dose according to a predetermined regimen, depending upon the indication for which the compound is administered.

By "statistically significant," as used herein, is meant results varying from control at the $p<0.1$ level of significance as measured using a standard parametric assay of statistical significance such as a student's T test.

A "patient" is any individual treated with a compound provided herein. Patients include humans, as well as other animals such as companion animals (e.g., dogs and cats) and livestock. Patients may be experiencing one or more symptoms of a condition responsive to $P2X_7$ modulation or may be free of such symptom(s) (i.e., treatment may be prophylactic in a patient considered at risk for the development of such symptoms).

Heteroaryl Amide Analogues

As noted above, the present invention provides heteroaryl amide analogues of Formula I. Within certain aspects, such compounds are modulators that may be used in a variety of contexts, including in the treatment of conditions responsive to $P2X_7$ modulation, such as pain. Such modulators are also useful as probes for detection and localization of $P2X_7$ and as standards in $P2X_7$-mediated signal transduction assays.

Within Formula I, the heteroaryl core:

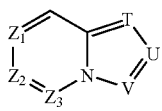

comprises at least one nitrogen atom, as indicated, and optionally comprises additional nitrogen atom(s) at one or more of T, U, V, $Z_1$, $Z_2$ and/or $Z_3$. In certain embodiments, $Z_3$ is $CR_2$; in further embodiments, $Z_3$ is CH. Within other embodiments, $Z_1$, $Z_2$ and $Z_3$ are each $CR_2$. The 5-membered ring portion of the core:

is, within certain embodiments,

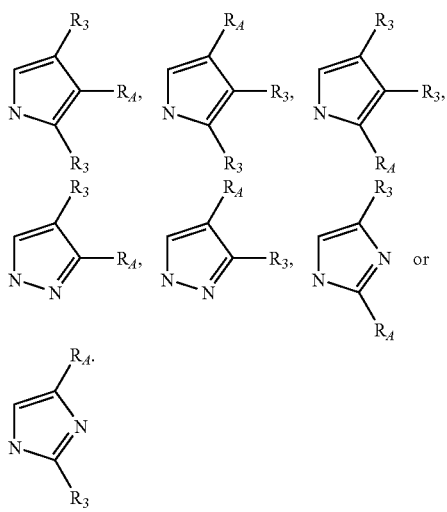

Where present, each $R_3$ is generally as described above; in certain compounds each $R_3$ is independently hydrogen or $C_1$-$C_4$alkyl.

The variable $R_A$ is a ring substituent as described above. In certain compounds, exactly one of T, U and V is $CR_A$ (i.e., one and only one of T, U and V is a carbon atom that is substituted with $R_A$). Representative $R_A$ groups include, for example, $C_1$-$C_6$hydroxyalkyl, $C_1$-$C_6$cyanoalkyl, $C_2$-$C_6$alkenyl, $C_2$-$C_6$alkyl ether, phenyl$C_0$-$C_4$alkyl (e.g., phenyl$C_1$-$C_4$alkyl), (4- to 7-membered heterocycle)$C_0$-$C_4$alkyl, ($C_1$-$C_6$alkylsulfonylamino)$C_0$-$C_4$alkyl, ($C_1$-$C_6$alkanoyloxy)$C_0$-$C_4$alkyl, ($C_1$-$C_6$alkylsulfonyloxy)$C_0$-$C_4$alkyl, (mono- or di-$C_1$-$C_6$alkylamino)$C_0$-$C_4$alkyl, and (mono- or di-$C_1$-$C_6$alkylaminocarbonyl)$C_0$-$C_4$alkyl; each of which is substituted with from 0 to 4 substituents independently chosen from: (i) oxo, halogen, amino, cyano, hydroxy, aminocarbonyl, aminosulfonyl and COOH; and (ii) $C_1$-$C_6$alkyl, $C_1$-$C_6$hydroxyalkyl, $C_1$-$C_6$alkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-$C_1$-$C_6$alkylaminocarbonyl, mono- or di-$C_1$-$C_6$alkylaminosulfonyl, phenyl and 4- to 7-membered heterocycle; each of which is substituted with from 0 to 4 substituents independently chosen from halogen, hydroxy, amino, oxo, aminocarbonyl, aminosulfonyl, COOH, $C_1$-$C_4$alkyl and $C_1$-$C_4$haloalkyl.

Within certain embodiments, $R_A$ is $C_1$-$C_6$hydroxyalkyl, $C_1$-$C_6$cyanoalkyl, $C_2$-$C_6$cyanoalkenyl, $C_2$-$C_6$alkyl ether, (mono- or di-$C_1$-$C_6$alkylamino)$C_0$-$C_4$alkyl, (mono- or di-$C_1$-$C_6$alkylaminocarbonyl)$C_0$-$C_4$alkyl, or (4- to 7-membered heterocycle)$C_1$-$C_4$alkyl; each of which is substituted with from 0 to 4 substituents independently chosen from amino, hydroxy, oxo, halogen, aminocarbonyl, aminosulfonyl, $C_1$-$C_6$alkyl, $C_1$-$C_6$hydroxyalkyl, $C_1$-$C_6$alkoxy, $C_2$-$C_6$alkyl ether, mono- or di-($C_1$-$C_6$alkyl)amino, mono- or di-$C_1$-$C_6$alkylaminocarbonyl, $C_1$-$C_6$alkylsulfonyl, $C_1$-$C_6$alkylsulfonylamino, 4- to 7-membered heterocycloalkyl, and 5- or 6-membered heteroaryl.

Within further embodiments, the "M" portion of $R_A$ is a N-linked heterocycloalkyl. Certain such $R_A$ groups satisfy the Formula:

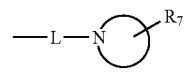

wherein: L is absent or $C_1$-$C_6$alkylene that is optionally substituted with oxo;

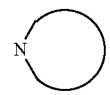

represents a 4- to 7-membered heterocycloalkyl that is optionally fused to phenyl or to a 5- or 6-membered heteroaryl; and $R_7$ represents from 0 to 4 substituents independently chosen from: (i) hydroxy, amino, oxo, aminocarbonyl, aminosulfonyl and COOH; (ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, and 4- to 7-membered heterocycle; each of which is substituted with from 0 to 4 substituents independently chosen from halogen, hydroxy, amino, oxo, aminocarbonyl, aminosulfonyl, COOH, $C_1$-$C_6$alkyl, $C_1$-$C_6$alkoxy, mono- or di-($C_1$-$C_6$alkyl)amino, and $C_1$-$C_6$alkylsulfonylamino; (iii) substituents that are taken together to form a bridge of the Formula —$(CH_2)_q$—P—$(CH_2)_r$—, wherein q and r are independently 0 or 1 and P is $CH_2$, O, NH or S; and (iv) substituents that are taken together to form a spiro 4- to 7-membered heterocycloalkyl ring that is substituted with from 0 to 2 substituents independently chosen from oxo and $C_1$-$C_4$alkyl.

Certain such $R_A$ moieties further satisfy the Formula:

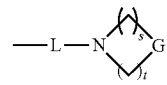

wherein: L is $C_1$-$C_2$alkylene that is optionally substituted with oxo; G is $CHR_8$, NH or O; s and t are independently 0, 1, 2, 3 or 4, such that the sum of s and t ranges from 2 to 5; and $R_8$ is: (i) hydrogen, amino, aminocarbonyl, aminosulfonyl or COOH; or (ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, or 4- to 7-membered heterocycle; each of which is substituted with from 0 to 4 substituents independently chosen from halogen, hydroxy, amino, oxo, aminocarbonyl, aminosulfonyl, COOH, $C_1$-$C_6$alkyl, $C_1$-$C_6$alkoxy, mono- or di-($C_1$-$C_6$alkyl)amino, and $C_1$-$C_6$alkylsulfonylamino.

Other such $R_A$ moieties further satisfy one of the following Formulas:

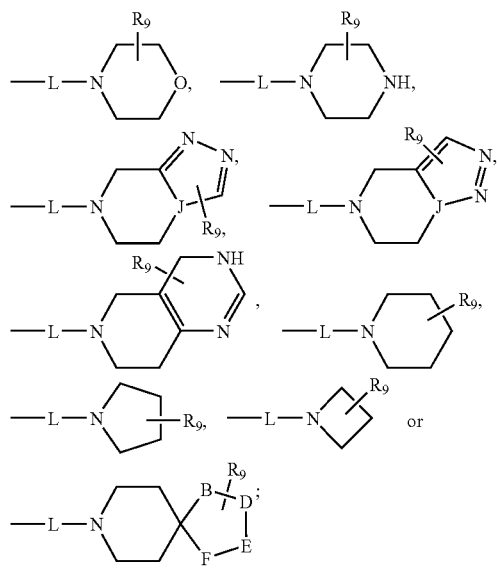

wherein J is CH or N; B, D, E and F are independently chosen from $CH_2$, NH and O; and $R_9$ represents from 0 to 2 substituents independently chosen from: (i) amino, aminocarbonyl and COOH; and (ii) $C_1$-$C_6$alkyl, mono- or di-($C_1$-$C_6$alkyl)amino$C_0$-$C_2$alkyl, $C_1$-$C_6$alkylsulfonyl and $C_1$-$C_6$alkylsulfonylamino; each of which is substituted with from 0 to 3 substituents independently chosen from halogen, hydroxy, oxo and COOH.

Within other embodiments, $R_A$ is $C_1$-$C_6$alkyl, $C_2$-$C_6$alkenyl, $C_2$-$C_6$alkyl ether, or mono- or di-($C_1$-$C_6$alkyl) amino$C_0$-$C_4$alkyl, each of which is substituted with from 1 to 4 substituents independently chosen from halogen, hydroxy, cyano, amino, oxo, aminocarbonyl, aminosulfonyl, COOH, $C_1$-$C_6$alkoxy, mono- or di-($C_1$-$C_6$alkyl)amino, $C_1$-$C_6$alkanoylamino, $C_1$-$C_6$alkylsulfonyl, $C_1$-$C_6$alkylsulfonyloxy, $C_6$alkylsulfonylamino, phenyl that is optionally substituted with halogen or $C_1$-$C_4$alkyl, and 4- to 7-membered heterocycle that is optionally substituted with $C_1$-$C_4$alkyl. Representative such $R_A$ groups include, for example, mono-($C_1$-$C_6$alkyl)amino$C_0$-$C_2$alkyl and $C_2$-$C_6$alkyl ether, each of which is substituted with from $C_1$-$C_4$alkyl and $C_1$-$C_4$alkoxy.

Within still further embodiments, $R_A$ is a group of the Formula L-A-M as described above, wherein L is not absent; A is absent; and M is phenyl or a 5- or 6-membered heteroaryl, each of which is substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle. Within certain such compounds, M is a 5- or 6-membered heteroaryl, each of which is optionally substituted. Certain such 5- or 6-membered heteroaryl moieties include, for example:

(i) imidazolyl, triazolyl, tetrazolyl, pyridyl, pyridazinyl or pyrimidinyl, each of which is substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle; and (ii)

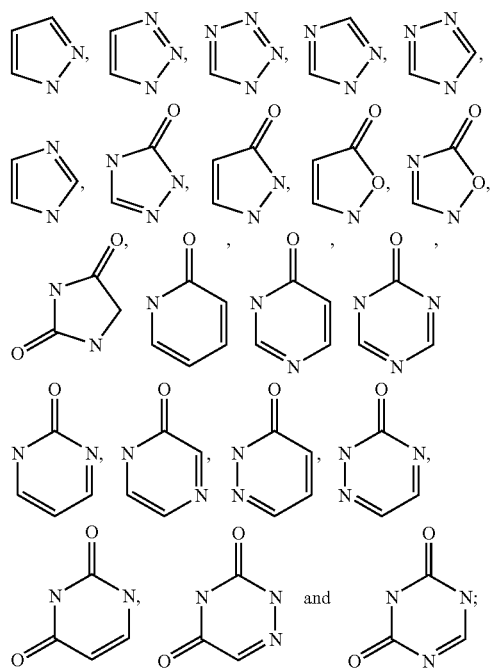

each of which is substituted with from 0 to 2 substituents independently chosen from amino, halogen, hydroxy, cyano, aminocarbonyl, aminosulfonyl, COOH, $C_1$-$C_6$hydroxyalkyl, $C_1$-$C_6$halo alkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino) carbonyl, and 4- to 7-membered heterocycle.

Within other embodiments, $R_A$ is a group of the Formula L-A-M, wherein L is $C_0$-$C_3$alkylene that is optionally substituted with oxo or COOH; A is absent; and M is phenyl that is substituted with amino, cyano, aminocarbonyl, aminosulfonyl, COOH or $C_1$-$C_6$alkyl.

Within other embodiments, $R_A$ is a group of the Formula L-A-M, wherein L is $C_1$-$C_2$alkylene that is optionally substituted with oxo; A is absent; and M is mono- or di-($C_1$-$C_6$alkyl)amino that is substituted with a 5- or 6-membered heteroaryl, each of which heteroaryl is substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di- ($C_1$-$C_6$)aminosulfonyl, mono- or di-($C_1$-$C_6$alkylamino)carbonyl, and 4- to 7-membered heterocycle. Representative 5- or 6-membered heteroaryls are as illustrated above.

As noted above, each of the variables $Z_1$, $Z_2$ and $Z_3$ in Formula A or Formula I is generally N, CH or substituted carbon. Within certain embodiments, $Z_1$, $Z_2$ and $Z_3$ are each $CR_2$; $Z_1$ is N and $Z_2$ and $Z_3$ are each $CR_2$; $Z_2$ is N and $Z_1$ and $Z_3$ are each $CR_2$; $Z_3$ is N and $Z_1$ and $Z_3$ are each $CR_2$; or $Z_1$ and $Z_3$ are N and $Z_2$ is $CR_2$. Each $R_2$, within certain such compounds, is hydrogen or $C_1$-$C_6$alkyl.

Certain representative heteroaryl cores:

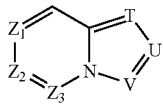

include, for example:

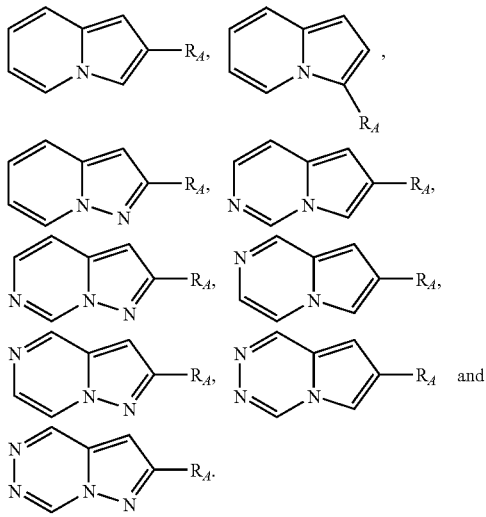

The variable "W," as noted above is generally W is —C(=O)$NR_4$—, —$NR_4$C(=O)— or —$NR_4$—$NR_4$—C(=O)—. It will be apparent that the orientation of these groups is intended to be retained; for example, in a compound in which W is —C(=O)$NR_4$—, the carbonyl of W is directly linked to the 6-membered ring of the bicyclic core and the nitrogen of W is directly linked to X. $R_4$ is generally as described above; in certain embodiments, $R_4$ is hydrogen or methyl.

The variable "X" is generally as described above; in certain embodiments, X is $C_1$-$C_4$alkylene (e.g., methylene or ethylene), each of which is substituted with from 0 to 4 substituents independently chosen from $C_1$-$C_4$alkyl, ($C_3$-$C_8$cycloalkyl)$C_0$-$C_2$alkyl, phenyl and substituents that are taken together to form a 3- to 7-membered cycloalkyl or heterocycloalkyl ring.

The variable "Y" is generally a cyclic moiety, optionally substituted. In certain compounds, Y is a cycloalkyl or heterocycloalkyl group, such as cyclopropyl, cyclobutyl, cyclopentyl, cyclohexyl, cycloheptyl, piperidinyl, piperazinyl, morpholinyl, or adamantyl, each of which is optionally substituted as described above; in certain such compounds, each Y moiety is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino.

Within certain heteroaryl amide analogues provided herein, —W—X—Y is:

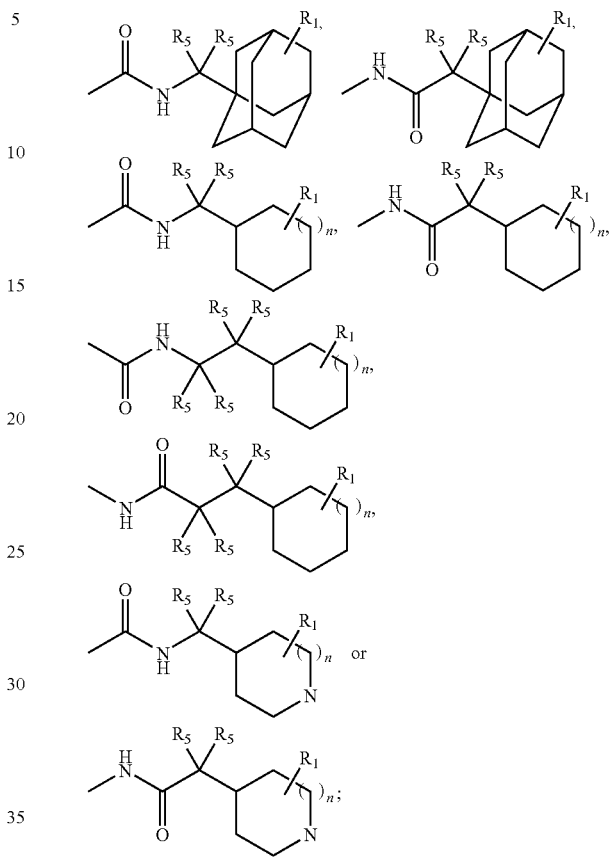

wherein: n is 0, 1 or 2; $R_1$ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; or two substituents represented by $R_1$ are taken together to form a $C_1$-$C_3$alkylene bridge or a fused or spiro 3- to 7-membered carbocyclic or heterocyclic ring; and each $R_5$ is independently hydrogen, $C_1$-$C_6$alkyl, $C_3$-$C_7$cycloalkyl or phenyl; or two $R_5$ are taken together to form a $C_3$-$C_8$cycloalkyl. Certain such compounds further satisfy the formula:

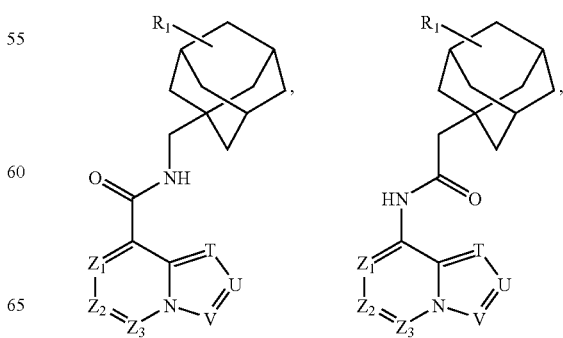

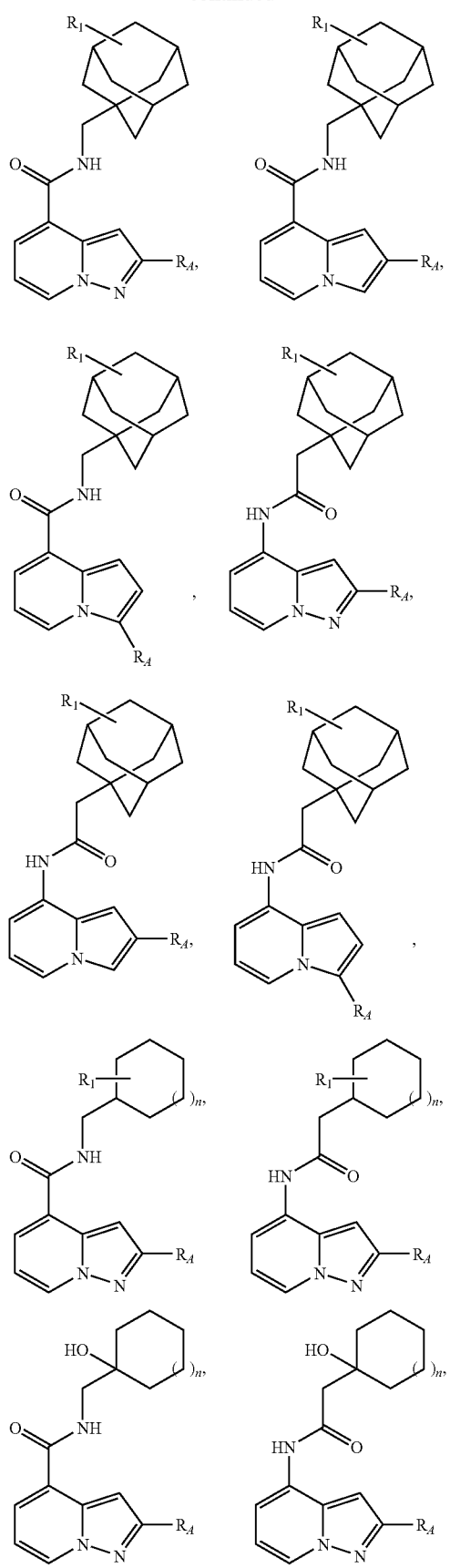

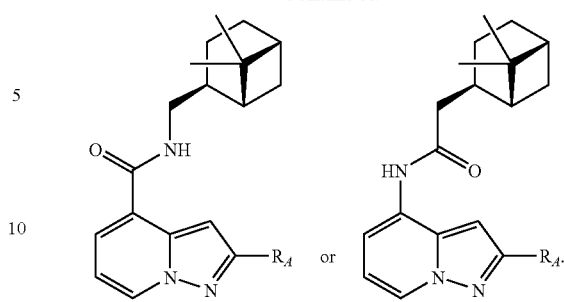

Within other compounds, Y is an aromatic moiety, such as: (i) phenyl or a 5- or 6-membered heteroaryl, each of which is optionally fused to a 5- to 7-membered carbocyclic or heterocyclic ring; or (ii)

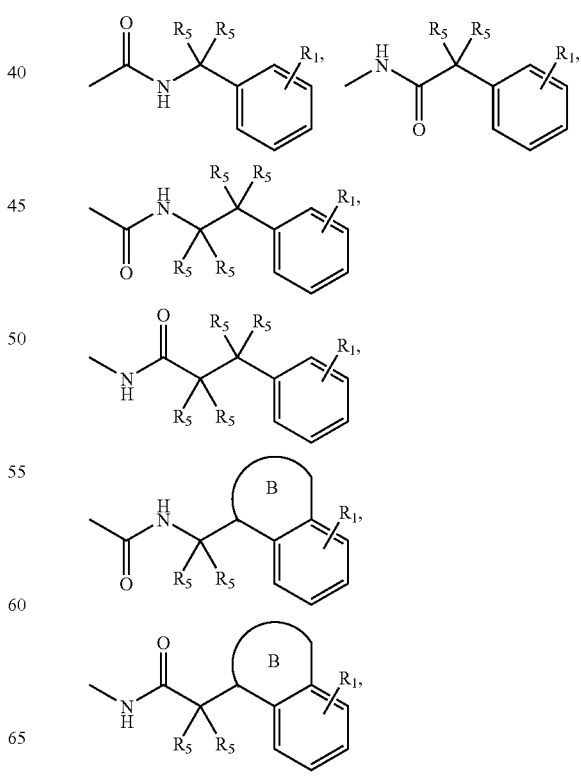

each of which Y is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy and mono- or di-($C_1$-$C_6$alkyl)amino. Within certain compounds, —W—X—Y is:

-continued

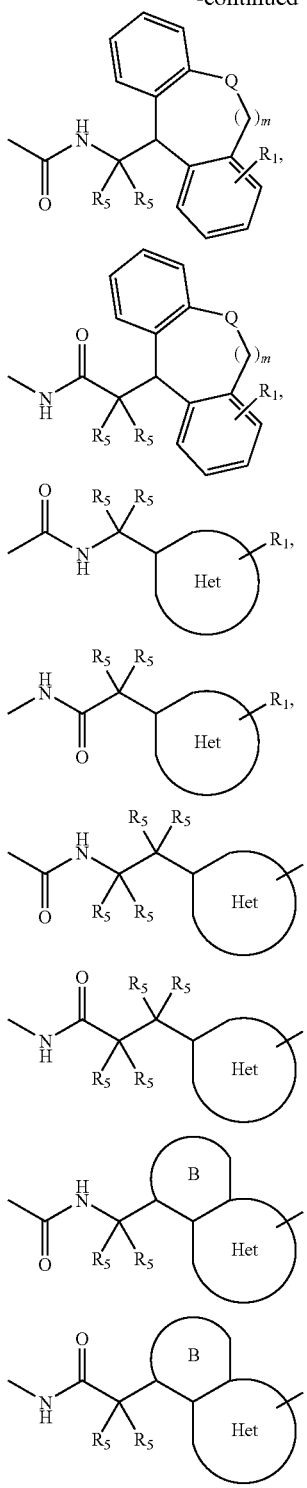

wherein:

is a 5- to 7-membered carbocyclic or heterocyclic ring;

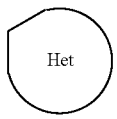

is a 5- or 6-membered heteroaryl; $R_1$ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl) amino; or two substituents represented by $R_1$ are taken together to form a fused or spiro 3- to 7-membered carbocyclic or heterocyclic ring; each $R_5$ is independently hydrogen, $C_1$-$C_6$alkyl, $C_3$-$C_7$cycloalkyl or phenyl; or two $R_5$ are taken together to form a $C_3$-$C_8$cycloalkyl; Q is $CH_2$, CO, O, NH, S, SO or $SO_2$; and m is 0 or 1. Certain such compounds further satisfy the formula:

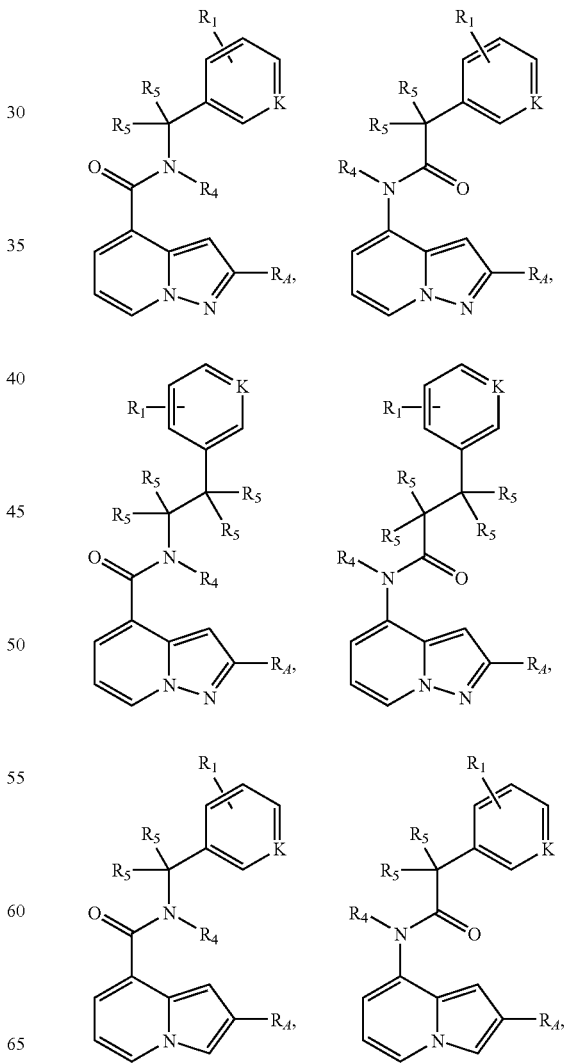

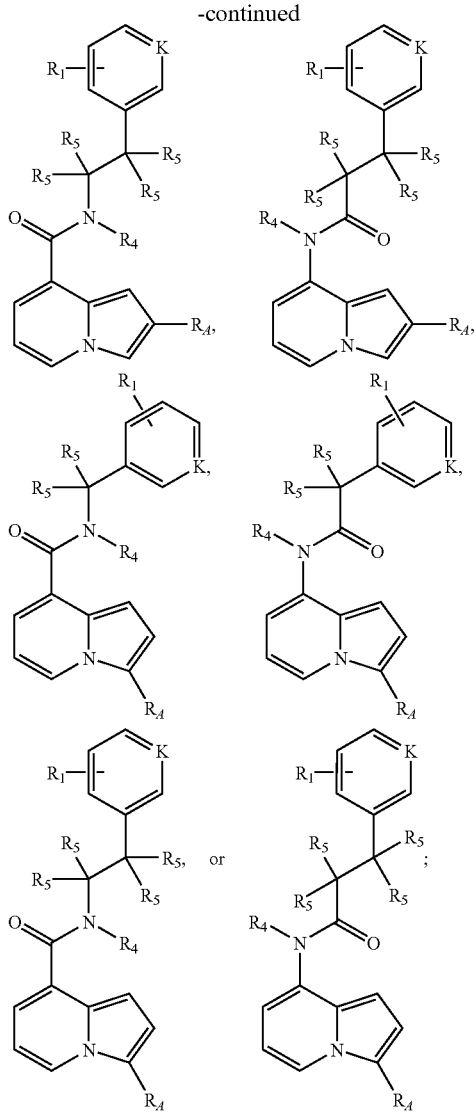

wherein K is CH or N. It will be apparent that when K is CH, the carbon atom at the K position may, but need not, be substituted with a substituent represented by $R_1$.

Representative heteroaryl amide analogues provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base, or as a pharmaceutically acceptable salt. In addition, other forms such as hydrates and prodrugs of such compounds are specifically contemplated by the present invention.

Within certain aspects of the present invention, heteroaryl amide analogues provided herein detectably alter (modulate) $P2X_7$ activity, as determined using an assay such as an assay recited in Example 4, herein. Additional assays that may be used for this purpose include assays that measure IL-1β release; assays that measure uptake of a membrane-impermeant fluorescent dye such as YO-PRO1; assays that measure lucifer yellow uptake; assays that measure ethidium bromide uptake; and assays that use calcium imaging to detect $P2X_7$ activity; all of which assays are well known in the art. Certain modulators provided herein detectably modulate $P2X_7$ activity at micromolar concentrations, at nanomolar concentrations, or at subnanomolar concentrations.

As noted above, compounds that are $P2X_7$ antagonists are preferred within certain embodiments. $IC_{50}$ values for such compounds may be determined using a standard in vitro $P2X_7$-mediated calcium mobilization assay, as provided in Example 4. Briefly, cells expressing $P2X_7$ are contacted with a compound of interest and with an indicator of intracellular calcium concentration (e.g., a membrane permeable calcium sensitivity dye such as Fluo-3, Fluo-4 or Fura-2 (Invitrogen, Carlsbad, Calif.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 hours). Cells are washed or filtered to remove excess dye and are then contacted with a $P2X_7$ agonist (e.g., ATP or 2'(3')-O-(4-benzoyl-benzoyl)adenosine 5'-triphosephate at, for example, a concentration equal to the agonist's $EC_{50}$), and a fluorescence response is measured. When agonist-contacted cells are contacted with a compound that is a $P2X_7$ antagonist, the fluorescence response is generally reduced by at least 20%, preferably at least 50% and more preferably at least 80%, as compared to cells that are contacted with the agonist in the absence of test compound. $IC_{50}$ stands for 50% Inhibitory Concentration, i.e., the concentration of compound that inhibits receptor (e.g., $P2X_7$) activity by 50% in an assay. Note that a lower $IC_{50}$ value for a compound at a particular receptor corresponds to the compound exhibiting more potency at that receptor, and higher $IC_{50}$ values correspond to less potency at that receptor. In certain embodiments, $P2X_7$ antagonists provided herein exhibit no detectable agonist activity an in vitro assay of $P2X_7$ agonism at a concentration of compound equal to the $IC_{50}$. Certain such antagonists exhibit no detectable agonist activity an in vitro assay of $P2X_7$ agonism at a concentration of compound that is 100-fold higher than the $IC_{50}$.

$P2X_7$ modulating activity may also, or alternatively, be assessed using an in vivo pain relief assay as provided in Example 5. Modulators provided herein preferably have a statistically significant specific effect on $P2X_7$ activity within such a functional assay.

In certain embodiments, preferred modulators are non-sedating. In other words, a dose of modulator that is twice the minimum dose sufficient to provide analgesia in an animal model for determining pain relief (such as a model provided in Example 5, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3):433-9). Preferably, a dose that is five times the minimum dose sufficient to provide analgesia does not produce statistically significant sedation. More preferably, a modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a therapeutically effective amount is administered to a subject), side effects (a preferred compound produces side effects comparable to placebo when a therapeutically effective amount of the compound is administered to a subject), serum protein binding and in vitro and in vivo half-life (a preferred compound exhibits an in vivo half-life allowing for no more than Q.I.D. dosing, preferably T.I.D. dosing, more preferably B.I.D. dosing, and most preferably once-a-day dosing). In addition, it may be desirable to select compounds with differential penetration of the blood brain barrier. For modulators used to treat pain or neurodegenerative disease by modulating CNS $P2X_7$ activity, high blood brain barrier penetration is preferred, such that total daily oral doses as described above provide such modulation in the CNS to a therapeutically effective extent, while compounds exhibiting low penetration of the blood brain barrier resulting in low brain levels of modulators may be preferred to treat peripheral nerve mediated pain or certain peripheral inflammatory diseases (e.g. rheumatoid arthritis). Preferably such low blood brain barrier penetrant compounds at such doses do not provide brain (e.g., CSF) levels of the compound sufficient to modulate $P2X_7$ activity to a clinically or therapeutically effective extent. Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described, for example, within Example 7 of U.S. Patent Application Publication Number 2005/0070547.

As noted above, preferred compounds provided herein are nontoxic. In general, the term "nontoxic" shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 8 of U.S. Patent Application Publication Number 2005/0070547. In other words, cells treated as described therein with 100 μM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ at $P2X_7$ for the compound does not elevate serum levels of ALT, LDH or AST in laboratory animals (e.g., rodents) by more than 100% over matched mock-treated controls. In more highly preferred embodiments, such doses do not elevate such serum levels by more than 75% or 50% over matched controls. Alternatively, a compound does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ at $P2X_7$ for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred compounds do not induce sister chromatid exchange (e.g., in Chinese hamster ovary cells) at such concentrations.

For detection purposes, as discussed in more detail below, modulators provided herein may be isotopically-labeled or radiolabeled. Substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Heteroaryl Amide Analogues

Heteroaryl amide analogues may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry. In some cases, protecting groups may be required during preparation. Such protecting groups can be removed by methods well known to those of ordinary skill in the art, such as methods described in Greene and Wuts, "Protective Groups in Organic Synthesis" (2nd Edition, John Wiley & Sons, 1991). In some cases, further organic transformations may be performed using methods well known to those of ordinary skill in the art, such as methods described in Richard C. Larock, "Comprehensive Organic Transformation," (VCH Publisher, Inc. 1989). Each variable in the following Schemes refers to any group consistent with the description of the compounds provided herein. Representative reaction conditions for use within the following schemes are provided in the Examples.

Certain abbreviations used in the following Schemes and elsewhere herein include:
Ac acetyl
aq. aqueous
ACN acetonitrile
BOP benzotriazol-1-yloxytris(dimethylamino)phosphonium hexafluorophosphate
Bu butyl
δ chemical shift
DCM dichloromethane
DIBAL-H diisobutylaluminium hydride
DMF dimethylformamide
DMSO dimethylsulfoxide
Et ethyl
EtOAc ethyl acetate
EtOH ethanol
h hour(s)
$^1$H NMR proton nuclear magnetic resonance
Hz hertz
iPr isopropyl
MeOH methanol
min minute(s)
Ms methanesulfonyl
(M+1) mass+1
Ph$_3$P triphenylphosphine
PTLC preparative thin layer chromatography
rt room temperature
TEA triethylamine
TFA trifluoroacetic acid
THF tetrahydrofuran

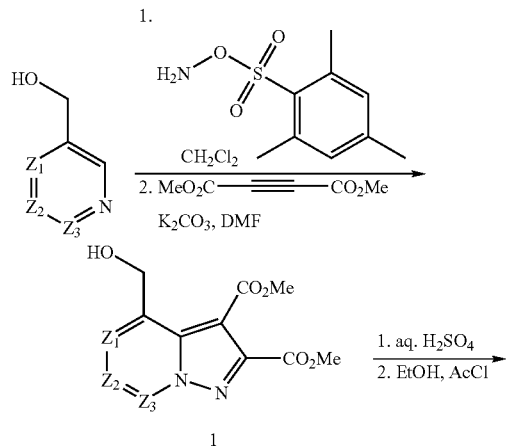

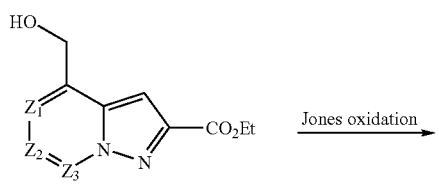

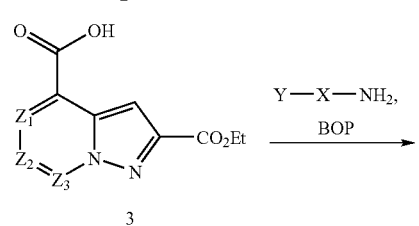

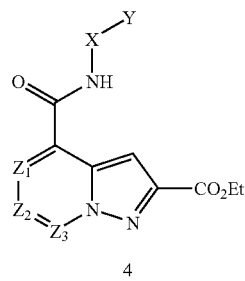

In Scheme I, dicarboxylic acid dimethyl ester 1 is prepared by reaction of the 3-pyridylcarbinol analogue with O-mesitylenesulfonylhydroxylamine in the presence of acetylene dicarboxylic acid dimethyl ester. Reaction of 1 with aqueous $H_2SO_4$ affords the 4-hydroxymethylpyrazolo[1,5-a]pyridine-2-carboxylic acid analogue, which is converted to the ethyl ester 2 by reaction with acetyl chloride in absolute ethanol. Oxidation of 2 with Jones reagent yields carboxylic acid 3, which is converted to amide 4 by reaction with an appropriate amine in the presence of BOP.

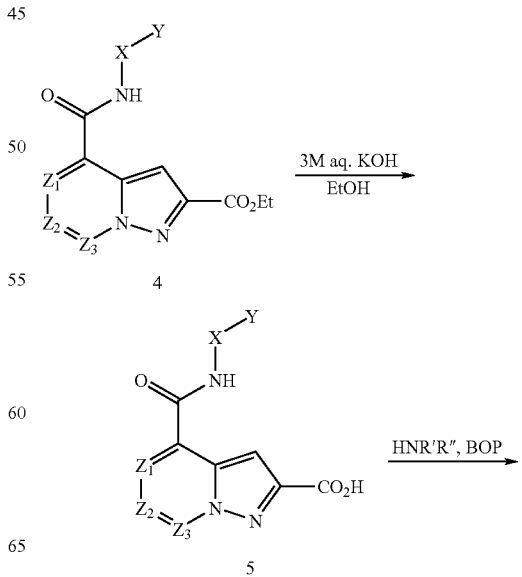

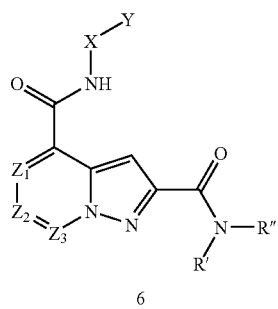

In Scheme II, ester 4 is hydrolyzed to yield the carboxylic acid 5. Amide 6 is prepared by reaction with an appropriate amine in the presence of BOP.

In Scheme III, ester 4 is reduced to the alcohol 7, which is converted to mesylate 8. Mesylate 8 is then used to generate amine 10 by reaction with an appropriate amine in the presence of potassium carbonate, or the cyanomethyl derivative 9 by reaction with sodium cyanide.

Scheme III

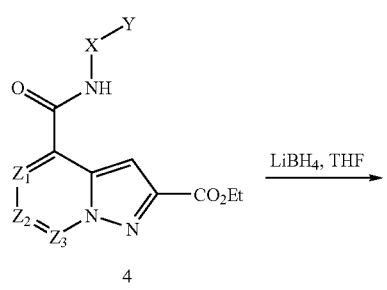

Scheme IV

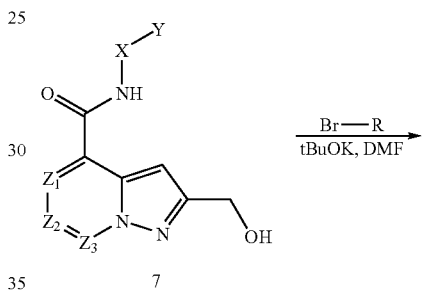

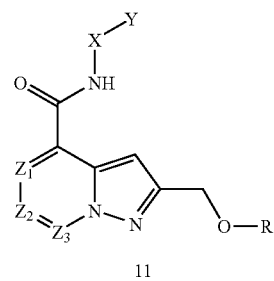

Scheme IV illustrates the conversion of alcohol 7 to any of a variety of ether moieties 11, via reaction with the appropriate brominated reagent.

Scheme V

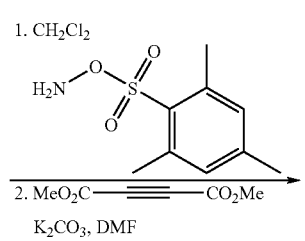

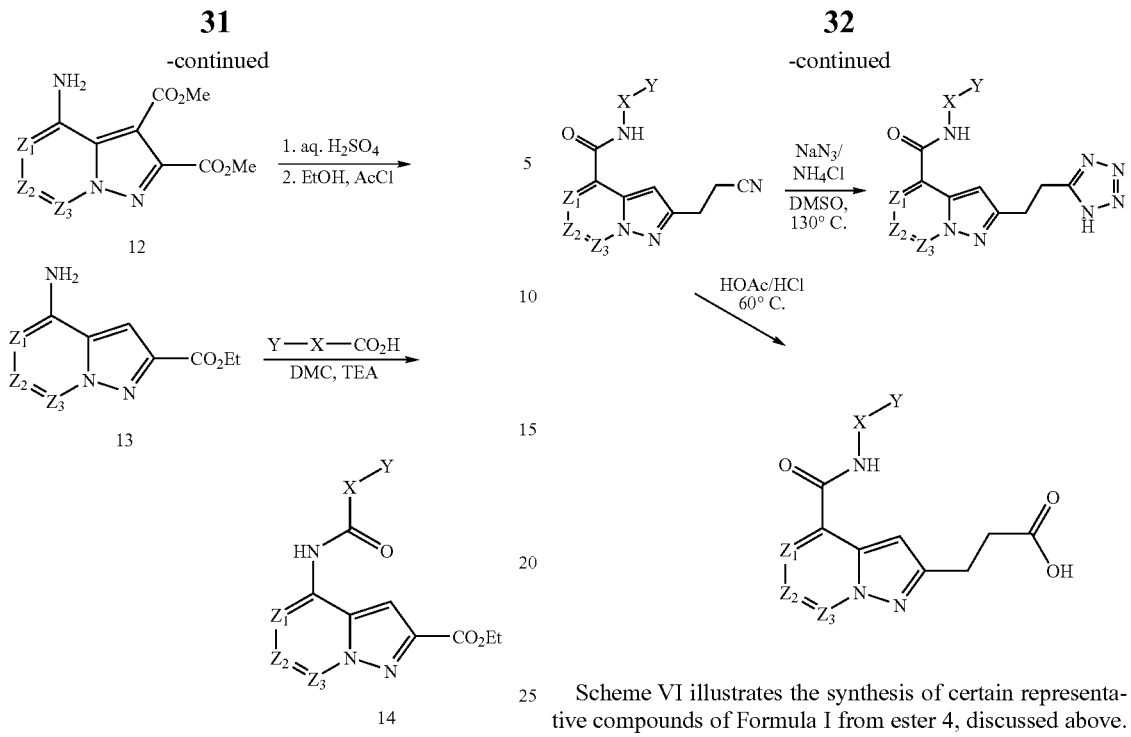

In Scheme V, dicarboxylic acid dimethyl ester 12 is prepared by reaction of the 3-aminopyridine analogue with O-mesitylenesulfonylhydroxylamine. Reaction of 12 with aqueous $H_2SO_4$ affords 4-aminopyrazolo[1,5-a]pyridine-2-carboxylic acid analogue 13, which is converted to the amide 14 by reaction with an appropriate carboxylic acid.

Scheme VI illustrates the synthesis of certain representative compounds of Formula I from ester 4, discussed above. The formyl derivative is generated by reaction with DIBAL, and is converted to the cyanovinyl derivative (a mixture of Z and E isomers) using $Ph_3P=CHCN$. Isomers can be separated using standard techniques. Reduction of the cyanovinyl compound (e.g., with Pd/C and 1 atm $H_2$) yields the cyanoethyl derivative, which can be converted to a variety of compounds, including the carboxylic acid and the tetrazolylethyl compounds illustrated.

Scheme VI

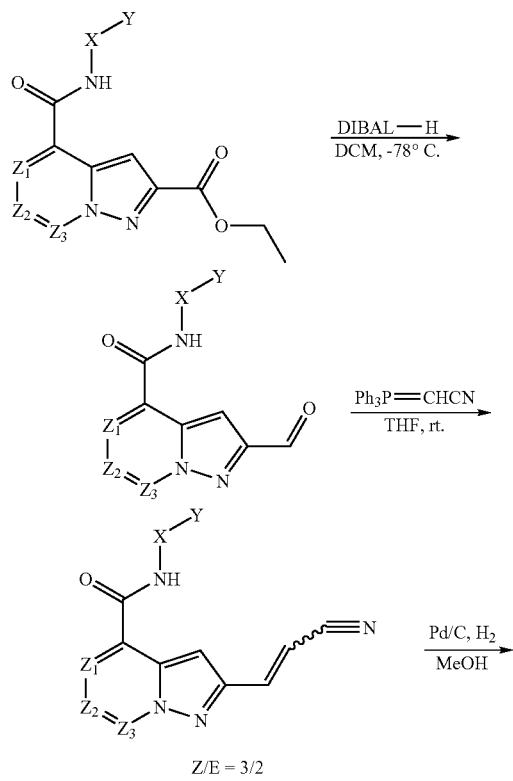

Scheme VII

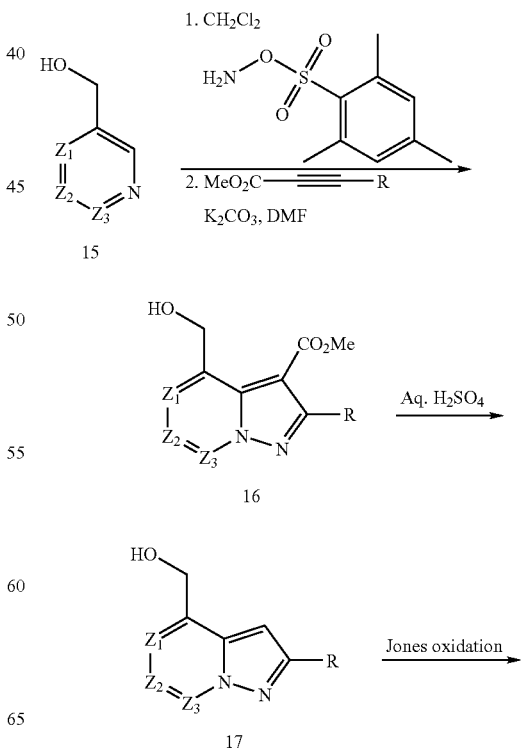

-continued

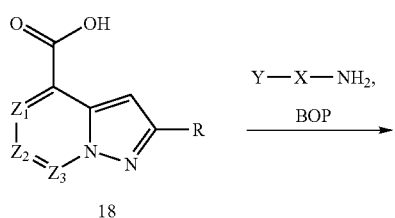
18

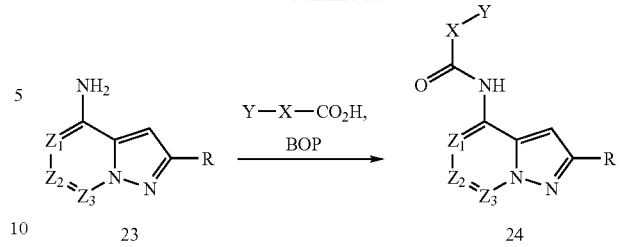
23  24

In Scheme VIII, carboxylic acid methyl ester 21 is prepared by reaction of the 3-aminopyridine analogue 20 with O-mesitylenesulfonylhydroxylamine in the presence of a methyl parpargellate derivative. Reaction of 21 with aqueous $H_2SO_4$ affords 4-aminopyrazolo[1,5-c]pyridine-2-carboxylic acid analogue 23, which is converted to the amide 24 by reaction with an appropriate carboxylic acid. Alternatively 21 can be directly reacted with an appropriate carboxylic acid to give amide 22.

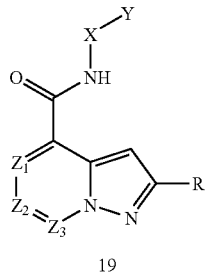
19

In Scheme VII, carboxylic acid methyl ester 16 is prepared by reaction of the 3-pyridylcarbinol analogue 15 with O-mesitylenesulfonylhydroxylamine in the presence of a propargyllic ester derivative, wherein R is hydrogen or any suitable group such as alkyl, cycloalkyl, heterocycloalkyl, aryl or heteroaryl each of which is optionally substituted. Reaction of 16 with aqueous $H_2SO_4$ affords the 4-hydroxymethylpyrazolo[1,5-a]pyridine 17. Oxidation of 17 with Jones reagent yields carboxylic acid 18, which is converted to amide 19 by reaction with an appropriate amine in the presence of BOP.

Scheme IX

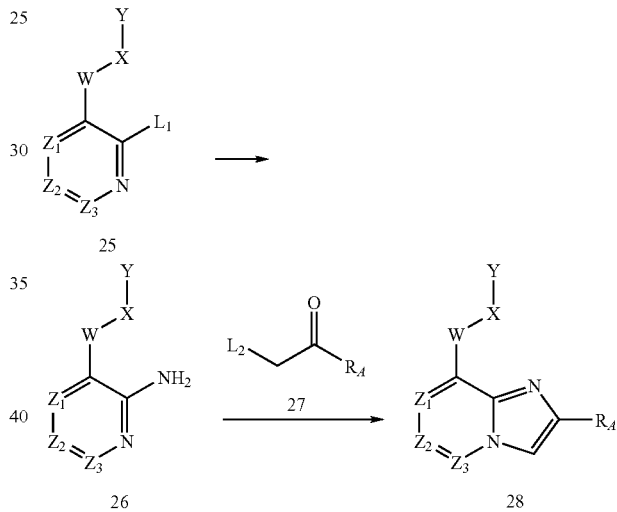

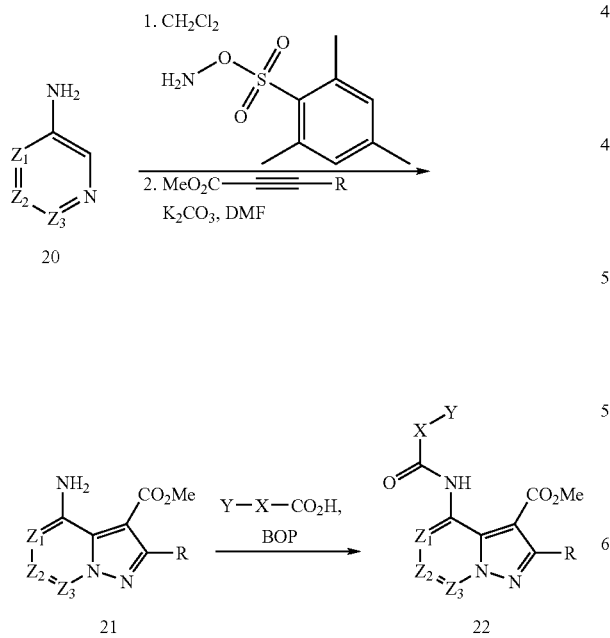

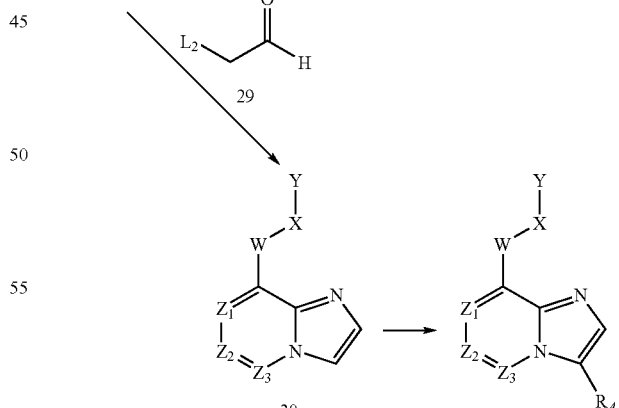

$L_1$ = F, Cl, Br, I
$L_2$ = Cl, Br

In Scheme IX, a nitrogen-containing heterocyclic halide 25 is converted to the aminoheterocycle 26 using any suitable method, such as ammonia in EtOH at rt or elevated temperature. Amino heterocycle 26 is reacted with an alpha halocarbonyl compound to give the substituted imidazoheterocycle 28. The alpha haloaldehyde 29 is reacted with aminoheterocycle 26 to give the unsubstituted imidazo heterocycle 30, which can be subsequently converted to substituted imidazoheterocycle 31 through electrophilic substitution of the imidazo functionality (e.g., via bromination to give the bromide), which can be converted to the desired imidazoheterocycle 31.

Scheme X

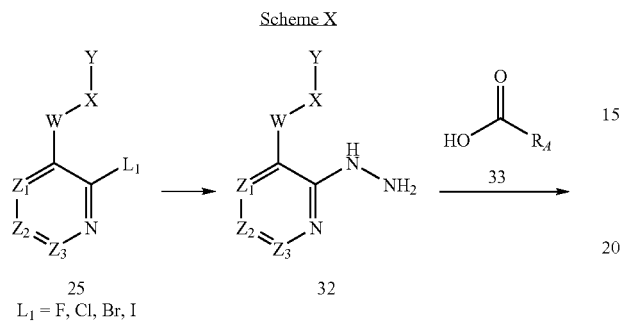

In Scheme X, a nitrogen-containing heterocyclic halide 25 is converted to the hydrazinoheterocycle 32 using any suitable method, such as, for example, reacting hydrazine in EtOH at RT or elevated temperature. Intermediate 32 is converted to triazoloheterocycle 34 by reacting with acid 33 without solvent or with solvent at rt or elevated temperature.

Scheme XI

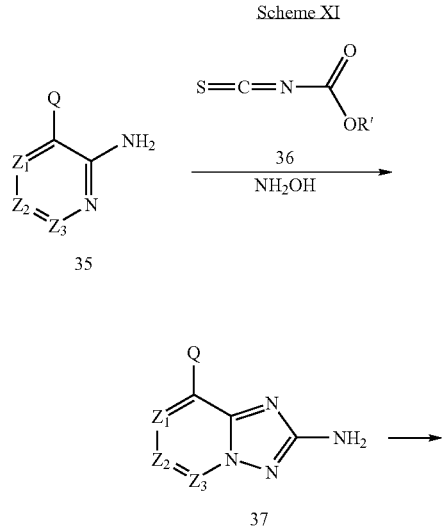

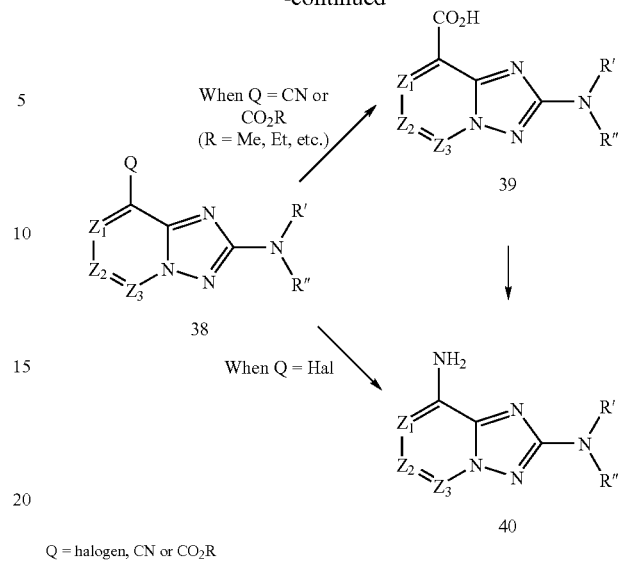

In Scheme XI, 35 is reacted with isothiocyanate 36 to form 37. The primary amine in compound 37 can be mono or di alylated or acylated to give compound 38. Hydrolysis of 38 (when Q is CN or an ester) under acidic conditions gives 39. Alternatively, if Q is a halogen, treatment of 38 with ammonium gives 40. 39 and 40 are readily converted to compounds of Formula I as illustrated above.

Scheme XII

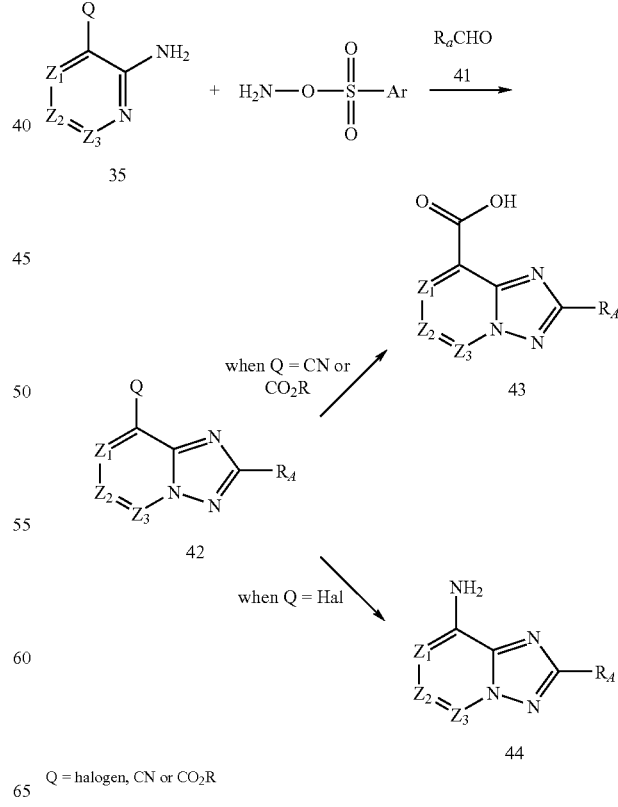

In Scheme XII, 35 is reacted with, for example, O-mesitylenesulfonyhydroxylamine at rt. Aldehyde 41 and aqueous KOH are then added to give intermediate 42. Hydrolysis of 42 (when Q is CN or an ester) under acidic conditions gives 43. Alternatively, if Q is a halogen, treatment of 42 with ammonium gives 44. 43 and 44 are readily converted to compounds of Formula I as illustrated above.

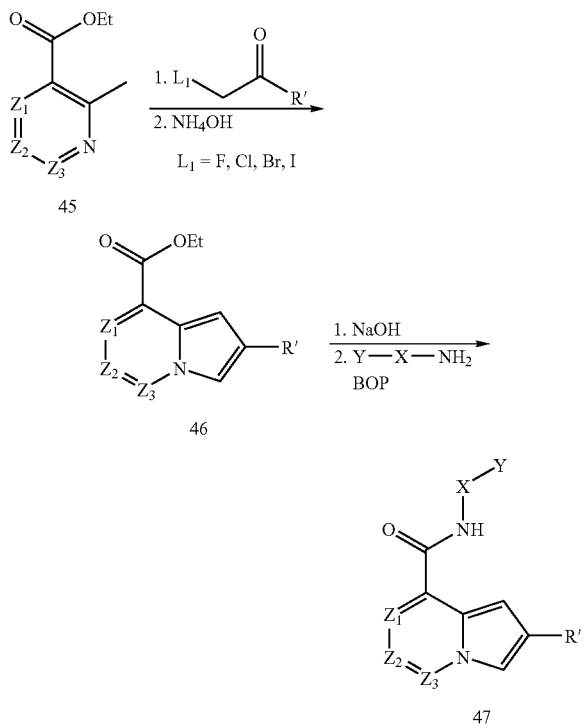

Scheme XIII

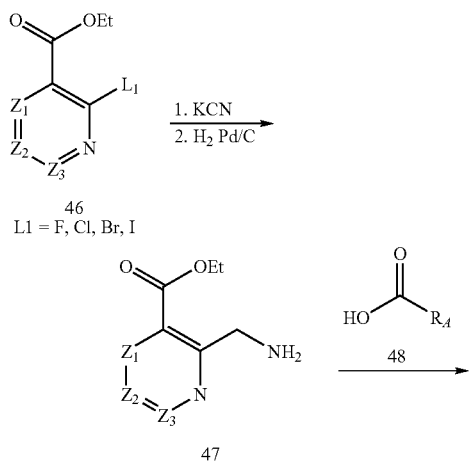

In Scheme XIII, a methyl substituted nitrogen heterocycle carboxylate ester 45 is reacted with an alpha-halocarbonyl compound and the intermediate slat is treated with ammonium hydroxide to give the ester 46. This is converted to the target compound 47 through standard conditions.

Scheme XIV

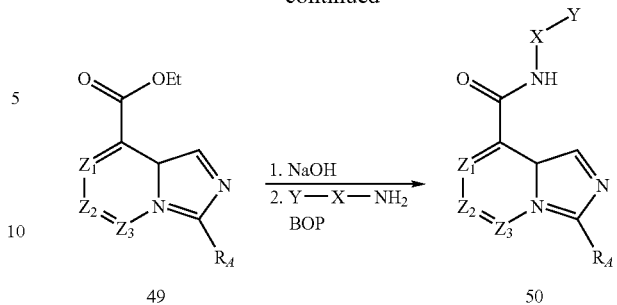

In Scheme XIV, a halogenated a nitrogen containing heterocyclic halide 46 is reacted with potassium cyanide and the resulting nitrile subjected to hydrogenation to give 47. 47 is condensed with acid 48 to give the heterocycle 49, which is converted to 50 by methods described herein.

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$) hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, one or more of water, buffers (e.g., sodium bicarbonate, neutral buffered saline or phosphate buffered saline), ethanol, mineral oil, vegetable oil, dimethylsulfoxide, carbohydrates (e.g., glucose, mannose, sucrose, starch, mannitol or dextrans), proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein.

Pharmaceutical compositions may be formulated for any appropriate manner of administration, including, for example, topical, oral, nasal, rectal, vaginal, or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, the compositions may be prepared as suppositories. In other embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, pharmaceutical compositions may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). Tablets may be formed using standard techniques, including dry granulation, direct compression and wet granulation. The tablets may be uncoated or they may be coated by known techniques.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with suitable excipients, such as suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and/or one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and *Remington: The Science and Practice of Pharmacy*, 21$^{st}$ ed., Lippincott Williams & Wilkins, Philadelphia, Pa. (2005). Formulations may comprise microcapsules, such as hydroxymethylcellulose or gelatin-microcapsules, liposomes, albumin microspheres, microemulsions, nanoparticles or nanocapsules.

A topical formulation may be prepared in any of a variety of physical forms including, for example, solids, pastes, ointments, creams, foams, lotions, gels, powders, aqueous liquids and emulsions. The physical appearance and viscosity of such pharmaceutically acceptable forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing.

A pharmaceutical composition may be prepared as a sterile injectible aqueous or oleaginous suspension. The compound(s) provided herein, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Pharmaceutical compositions may be formulated for release at a pre-determined rate. Instantaneous release may be achieved, for example, via sublingual administration (i.e., administration by mouth in such a way that the active ingredient(s) are rapidly absorbed via the blood vessels under the tongue rather than via the digestive tract). Controlled release formulations (i.e., formulations such as a capsule, tablet or coated tablet that slows and/or delays release of active ingredient(s) following administration) may be administered by, for example, oral, rectal or subcutaneous implantation, or by implantation at a target site. In general, a controlled release formulation comprises a matrix and/or coating that delays disintegration and absorption in the gastrointestinal tract (or implantation site) and thereby provides a delayed action or a sustained action over a longer period. One type of controlled-release formulation is a sustained-release formulation, in which at least one active ingredient is continuously released over a period of time at a constant rate. Preferably, the therapeutic agent is released at such a rate that blood (e.g., plasma) concentrations are maintained within the therapeutic range, but below toxic levels, over a period of time that is at least 4 hours, preferably at least 8 hours, and more preferably at least 12 hours. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

Controlled release may be achieved by combining the active ingredient(s) with a matrix material that itself alters release rate and/or through the use of a controlled-release coating. The release rate can be varied using methods well known in the art, including (a) varying the thickness or composition of coating, (b) altering the amount or manner of addition of plasticizer in a coating, (c) including additional ingredients, such as release-modifying agents, (d) altering the composition, particle size or particle shape of the matrix, and (e) providing one or more passageways through the coating. The amount of modulator contained within a sustained release formulation depends upon, for example, the method of administration (e.g., the site of implantation), the rate and expected duration of release and the nature of the condition to be treated or prevented.

The matrix material, which itself may or may not serve a controlled-release function, is generally any material that supports the active ingredient(s). For example, a time delay material such as glyceryl monosterate or glyceryl distearate may be employed. Active ingredient(s) may be combined with matrix material prior to formation of the dosage form (e.g., a tablet, a capsule, a troche, or a sprinkle). Alternatively, or in addition, active ingredient(s) may be coated on the surface of a particle, granule, sphere, microsphere, bead or pellet that comprises the matrix material. Such coating may be achieved by conventional means, such as by dissolving the active ingredient(s) in water or other suitable solvent and spraying. Optionally, additional ingredients are added prior to coating (e.g., to assist binding of the active ingredient(s) to the matrix material or to color the solution). The matrix may then be coated with a barrier agent prior to application of controlled-release coating. Multiple coated matrix units may, if desired, be encapsulated to generate the final dosage form.

In certain embodiments, a controlled release is achieved through the use of a controlled release coating (i.e., a coating that permits release of active ingredient(s) at a controlled rate in aqueous medium). The controlled release coating should be a strong, continuous film that is smooth, capable of supporting pigments and other additives, non-toxic, inert and tack-free. Coatings that regulate release of the modulator include pH-independent coatings, pH-dependent coatings (which may be used to release modulator in the stomach) and enteric coatings (which allow the formulation to pass intact through the stomach and into the small intestine, where the coating dissolves and the contents are absorbed by the body). It will be apparent that multiple coatings may be employed (e.g., to allow release of a portion of the dose in the stomach and a portion further along the gastrointestinal tract). For example, a portion of active ingredient(s) may be coated over an enteric coating, and thereby released in the stomach, while the remainder of active ingredient(s) in the matrix core is protected by the enteric coating and released further down the GI tract. pH dependent coatings include, for example, shellac, cellulose acetate phthalate, polyvinyl acetate phthalate, hydroxypropylmethylcellulose phthalate, methacrylic acid ester copolymers and zein.

In certain embodiments, the coating is a hydrophobic material, preferably used in an amount effective to slow the hydration of the gelling agent following administration. Suitable hydrophobic materials include alkyl celluloses (e.g., ethylcellulose or carboxymethylcellulose), cellulose ethers, cellulose esters, acrylic polymers (e.g., poly(acrylic acid), poly(methacrylic acid), acrylic acid and methacrylic acid copolymers, methyl methacrylate copolymers, ethoxy ethyl methacrylates, cyanoethyl methacrylate, methacrylic acid alkamide copolymer, poly(methyl methacrylate), polyacrylamide, ammonio methacrylate copolymers, aminoalkyl methacrylate copolymer, poly(methacrylic acid anhydride) and glycidyl methacrylate copolymers) and mixtures of the foregoing. Representative aqueous dispersions of ethylcellulose include, for example, AQUACOAT® (FMC Corp., Philadelphia, Pa.) and SURELEASE® (Colorcon, Inc., West Point, Pa.), both of which can be applied to the substrate according to the manufacturer's instructions. Representative acrylic polymers include, for example, the various EUDRAGIT® (Rohm America, Piscataway, N.J.) polymers, which may be used singly or in combination depending on the desired release profile, according to the manufacturer's instructions.

The physical properties of coatings that comprise an aqueous dispersion of a hydrophobic material may be improved by the addition or one or more plasticizers. Suitable plasticizers for alkyl celluloses include, for example, dibutyl sebacate, diethyl phthalate, triethyl citrate, tributyl citrate and triacetin. Suitable plasticizers for acrylic polymers include, for example, citric acid esters such as triethyl citrate and tributyl citrate, dibutyl phthalate, polyethylene glycols, propylene glycol, diethyl phthalate, castor oil and triacetin.

Controlled-release coatings are generally applied using conventional techniques, such as by spraying in the form of an aqueous dispersion. If desired, the coating may comprise pores or channels or to facilitate release of active ingredient. Pores and channels may be generated by well known methods, including the addition of organic or inorganic material that is dissolved, extracted or leached from the coating in the environment of use. Certain such pore-forming materials include hydrophilic polymers, such as hydroxyalkylcelluloses (e.g., hydroxypropylmethylcellulose), cellulose ethers, synthetic water-soluble polymers (e.g., polyvinylpyrrolidone, cross-linked polyvinylpyrrolidone and polyethylene oxide), water-soluble polydextrose, saccharides and polysaccharides and alkali metal salts. Alternatively, or in addition, a controlled release coating may include one or more orifices, which may be formed my methods such as those described in U.S. Pat. Nos. 3,845,770; 4,034,758; 4,077,407; 4,088,864; 4,783,337 and 5,071,607. Controlled-release may also be achieved through the use of transdermal patches, using conventional technology (see, e.g., U.S. Pat. No. 4,668,232).

Further examples of controlled release formulations, and components thereof, may be found, for example, in U.S. Pat. Nos. 4,572,833; 4,587,117; 4,606,909; 4,610,870; 4,684,516; 4,777,049; 4,994,276; 4,996,058; 5,128,143; 5,202,128; 5,376,384; 5,384,133; 5,445,829; 5,510,119; 5,618,560; 5,643,604; 5,891,474; 5,958,456; 6,039,980; 6,143,353; 6,126,969; 6,156,342; 6,197,347; 6,387,394; 6,399,096; 6,437,000; 6,447,796; 6,475,493; 6,491,950; 6,524,615; 6,838,094; 6,905,709; 6,923,984; 6,923,988; and 6,911,217; each of which is hereby incorporated by reference for its teaching of the preparation of controlled release dosage forms.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds are generally administered in a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated, the particular mode of administration and any other co-administered drugs. Dosage units generally contain between from about 10 μg to about 500 mg of active ingredient. Optimal dosages may be established using routine testing, and procedures that are well known in the art.

Pharmaceutical compositions may be packaged for treating conditions responsive to $P2X_7$ modulation (e.g., pain, inflammation, neurodegeneration or other condition described herein). Packaged pharmaceutical compositions generally include (i) a container holding a pharmaceutical composition that comprises at least one modulator as described herein and (ii) instructions (e.g., labeling or a package insert) indicating that the contained composition is to be used for treating a condition responsive to $P2X_7$ modulation in the patient.

Methods of Use $P2X_7$ modulators provided herein may be used to alter activity and/or activation of $P2X_7$ in a variety of contexts, both in vitro and in vivo. Within certain aspects, $P2X_7$ antagonists may be used to inhibit the binding of ligand agonist to $P2X_7$ in vitro or in vivo. In general, such methods comprise the step of contacting a $P2X_7$ with one or more $P2X_7$ modulators provided herein, in the presence of ligand in aqueous solution and under conditions otherwise suitable for binding of the ligand to $P2X_7$. The modulator(s) are generally present at a concentration that is sufficient to alter $P2X_7$-mediated signal transduction (using an assay provided in Example 4). The $P2X_7$ may be present in solution or suspension (e.g., in an isolated membrane or cell preparation), or in a cultured or isolated cell. Within certain embodiments, the $P2X_7$ is expressed by a cell that is present in a patient, and the aqueous solution is a body fluid. Preferably, one or more modulators are administered to an animal in an amount such that the modulator is present in at least one body fluid of the animal at a therapeutically effective concentration that is 20 micromolar or less, 10 micromolar or less, 5 micromolar or less, or 1 micromolar or less. For example, such compounds may be administered at a therapeutically effective dose that is less than 20 mg/kg body weight, preferably less than 5 mg/kg and, in some instances, less than 1 mg/kg.

Also provided herein are methods for modulating, preferably reducing, cellular $P2X_7$ activation and/or activity, such as signal-transducing activity (e.g., calcium conductance). Such modulation may be achieved by contacting a $P2X_7$ (either in vitro or in vivo) with one or more modulators provided herein under conditions suitable for binding of the modulator(s) to $P2X_7$. The modulator(s) are generally present at a concentration that is sufficient to alter $P2X_7$-mediated signal transduction as described herein. $P2X_7$ may be present in solution or suspension, in a cultured or isolated cell preparation or in a cell within a patient. For example, the cell may be contacted in vivo in an animal. Modulation of signal transducing activity may be assessed by detecting an effect on calcium ion conductance (also referred to as calcium mobilization or flux). Modulation of signal transducing activity may alternatively be assessed by detecting an alteration of a symptom (e.g., pain or inflammation) of a patient being treated with one or more modulators provided herein.

$P2X_7$ modulator(s) provided herein are preferably administered to a patient (e.g., a human) orally or topically, and are present within at least one body fluid of the animal while modulating $P2X_7$ signal-transducing activity.

The present invention further provides methods for treating conditions responsive to $P2X_7$ modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to $P2X_7$ modulation" if it is characterized by inappropriate activity of a $P2X_7$, regardless of the amount of $P2X_7$ agonist present locally, and/or if modulation of $P2X_7$ activity results in alleviation of the condition or a symptom thereof. Such conditions include, for example, pain, inflammation, cardiovascular disorders, ocular disorders, neurodegenerative disorders and respiratory disorders (such as cough, asthma, chronic obstructive pulmonary disease, chronic bronchitis, cystic fibrosis and rhinitis, including allergic rhinitis, such as seasonal an perennial rhinitis, and non-allergic rhinitis), fibrosis as well as other conditions described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated; however, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Pain that may be treated using the modulators provided herein includes, for example, acute, chronic, inflammatory, and neuropathic pain. Specific pain indications that may be treated as described herein include, but are not limited to, pain associated with osteoarthritis or rheumatoid arthritis; various neuropathic pain syndromes (such as post-herpetic neuralgia, trigeminal neuralgia, reflex sympathetic dystrophy, diabetic neuropathy, Guillian Barre syndrome, fibromyalgia, oral neuropathic pain, phantom limb pain, post-mastectomy pain, peripheral neuropathy, myofascial pain syndromes, MS-related neuropathy, HIV or AIDS-related neuropathy, and chemotherapy-induced and other iatrogenic neuropathies); visceral pain, (such as that associated with gastroesophageal reflux disease (GERD), irritable bowel syndrome, inflammatory bowel disease, pancreatitis, intestinal gas, gynecological disorders (e.g., menstrual pain, dysmenorrhoea, pain associated with cystitis, labor pain, chronic pelvic pain, chronic prostitis, endometriosis, heart pain and abdominal pain), and urological disorders); dental pain (e.g., toothache, denture pain, nerve root pain, pain resulting from periodontal disease, and pain due to dental surgery including operative and post-operative pain); headache (e.g., headaches involving peripheral nerve activity, sinus headache, cluster headache (i.e., migranous neuralgia) tension headache, migraine, temporomandibular pain and maxillary sinus pain); stump pain; meralgia paresthetica; burning-mouth syndrome; pain associated with nerve and root damage, including as pain associated with peripheral nerve disorders (e.g., nerve entrapment and brachial plexus avulsions, amputation, peripheral neuropathies including bilateral peripheral neuropathy, tic douloureux, atypical facial pain, nerve root damage, and arachnoiditis), causalgia, neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia); surgery-related pain; musculoskeletal pain; central nervous system pain (e.g., pain due to brain stem damage, sciatica, and ankylosing spondylitis); and spinal pain, including spinal cord injury-related pain.

Further pain conditions that can be treated as described herein include Charcot's pains, ear pain, muscle pain, eye pain, orofacial pain (e.g., odontalgia), carpel tunnel syndrome, acute and chronic back pain (e.g., lower back pain), gout, scar pain, hemorrhoidal pain, dyspeptic pains, angina, nerve root pain, "non-painful" neuropathies, complex regional pain syndrome, homotopic pain and heterotopic pain—including pain associated with carcinoma, often referred to as cancer-associated pain (e.g., in patients with bone cancer), pain (and inflammation) associated with venom exposure (e.g., due to snake bite, spider bite, or insect sting) and trauma-associated pain (e.g., post-surgical pain, episiotomy pain, pain from cuts, musculoskeletal pain, bruises and broken bones, and burn pain, especially primary hyperalgesia associated therewith). Additional pain conditions that may be treated as described herein include pain associated with autoimmune diseases or immunodeficiency disorders, hot flashes, burns, sunburn, and pain that results from exposure to heat, cold or external chemical stimuli.

Conditions associated with inflammation and/or immune system disorders that may be treated using the modulators provided herein include, but are not limited to, arthritis (including osteoarthritis, rheumatoid arthritis, psoriatic arthritis, Reiter's syndrome, gout, traumatic arthritis, rubella arthritis, rheumatoid spondylitis, gouty arthritis and juvenile arthritis); cystic fibrosis; uveitis; systemic lupus erythematosus (and associated glomerulonephritis); spondyloarthropathies; psoriasis; scleritis; allergic conditions (including allergic reactions, allergic rhinitis, allergic contact hypersensitivity, allergic dermatitis, eczema and contact dermatitis), reperfusion injury (e.g., cardiac and renal reperfusion injury), respiratory system disorders (including hyper-responsiveness of the airway, cough, asthma (e.g., to prevent or decrease the severity of both acute early phase asthma attack and the late phase reactions that follow such an asthma attack; including bronchial, allergic, intrinsic, extrinsic, exercise-induced, drug-induced (e.g., aspirin or NSAID-induced) and dust-induced asthma), reactive airway disease, emphysema, acute (adult) respiratory distress syndrome (ARDS), bronchitis (e.g., infectious and eosinophilic bronchitis), bronchiectasis, chronic pulmonary obstructive disorder (COPD), chronic pulmonary inflammatory disease, silicosis, pulmonary sarcoidosis, farmer's lung, hypersensitivity pneumonitis and lung fibrosis), viral infection, fungal infection, bacterial infection, Crohn's disease, glomerulornephritis, HIV infection and AIDS, irritable bowel syndrome, inflammatory bowel disease, dermatomyositis, multiple sclerosis, pemphigus, pemphigoid, scleroderma, myasthenia gravis, autoimmune hemolytic and thrombocytopenic states, Goodpasture's syndrome (and associated glomerulonephritis and pulmonary hemorrhage), tissue graft rejection, hyperacute rejection of transplanted organs, allograft rejection, organ transplant toxicity, neutropenia, sepsis, septic shock, endotoxic shock, conjunctivitis shock, toxic shock syndrome, Alzheimer's disease, inflammation associated with severe burns, lung injury, systemic inflammatory response syndrome (SIRS), neonatal-onset multisystem inflammatory disease (NOMID), Hashimoto's thyroiditis, Grave's disease, Addison's disease, idiopathic thrombocytopaenic purprua, eosinophilic fascitis, hyper-IgE syndrome, antiphospholipid syndrome, leprosy, Sezary syndrome, paraneoplastic syndromes, Muckle-Wells syndrome, lichen planus, familial cold autoinflammatory syndrome (FCAS), colitis, ruptured abdominal aortic aneurysm and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, macular degeneration, contact sensitivity responses, and inflammation resulting from contact of blood with artificial surfaces as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Still further conditions that may be treated using the modulators provided herein include:

Cardiovascular disorders, such as cardiovascular disease, stroke, cerebral ischemia, myocardial infarction, atherosclerosis, ischemic heart disease, ischemia-reperfusion injury, aortic aneurysm, and congestive heart failure;

Ocular disorders such as glaucoma;

Neurological disorders (e.g., neurodegeneration), such as neurodegenerative conditions associated with progressive CNS disorders, including, but not limited to, Alzheimer's disease, Parkinson's disease, amyotrophic lateral sclerosis, Huntington's disease, Creutzfeldt-Jakob disease, dementia with Lewy bodies, traumatic brain injury, spinal cord injury, neurotrauma, cerebral amyloid angiopathy, and encephalitis; epilepsy and seizure disorders; multiple sclerosis and other demyelinating syndromes; cerebral atherosclerosis; vasculitis; temporal arteritis; myasthenia gravis; neurosarcoidosis; and central and peripheral nervous system complications of malignant, infectious or autoimmune processes; the modulators provided herein may also be used to promote neuroregeneration;

Centrally-mediated neuropsychiatric disorders, such as depression, depression mania, bipolar disease, anxiety, schizophrenia, eating disorders, sleep disorders and cognition disorders; and Other disorders, such as cirrhosis, interstitial fibrosis, prostate, bladder and bowel dysfunction (e.g., urinary incontinence, urinary hesitancy, rectal hypersensitivity, fecal incontinence and benign prostatic hypertrophy); itch/pruritus; obesity; lipid disorders; cancer; hypertension; renal disorders; abnormal wound healing; myoblastic leukemia; diabetes; meningitis; varicose veins; muscle degeneration; cachexia; restenosis; thrombosis; cerebral malaria; disorders of bones and joints (e.g., osteoporosis, bone resorption disease, loosening of artificial joint implants, and others listed above); epidermolysis bullosa; ocular angiogenesis; corneal injury; corneal scarring; and tissue ulceration.

Modulators provided herein may also be used for neuroprotection of the optic nerve (e.g., to inhibit the death of retinal ganglion cells in a patient).

Within other aspects, modulators provided herein may be used within combination therapy for the treatment of conditions responsive to $P2X_7$ modulation (e.g., conditions involving pain and/or inflammatory components). Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebro-vascular disease and certain infectious diseases.

Within such combination therapy, a modulator is administered to a patient along with a second therapeutic agent (e.g., an analgesic and/or anti-inflammatory agent). The modulator and second therapeutic agent may be present in the same pharmaceutical composition, or may be administered separately in either order. Anti-inflammatory agents include, for example, non-steroidal anti-inflammatory drugs (NSAIDs), non-specific and cyclooxygenase-2 (COX-2) specific cyclooxygenase enzyme inhibitors, gold compounds, corticosteroids, methotrexate, leflunomide, cyclosporine A, IM gold, minocycline, azathioprine, tumor necrosis factor (TNF) receptor antagonists, soluble TNF alpha receptor (etanercept), anti-TNF alpha antibodies (e.g., infliximab and adalimumab), anti-05 antibodies, interleukin-1 (IL-1) receptor antagonists (e.g., anakinra or IL-1 trap), IL-18 binding protein, CTLA4-Ig (e.g., abatacept), anti-human IL-6 receptor monoclonal antibody (e.g., tocilizumab), LFA-3-Ig fusion proteins (e.g., alefacept), LFA-1 antagonists, anti-VLA4 monoantibody (e.g., natalizumab), anti-CD11a monoclonal antibody, anti-CD20 monoclonal antibody (e.g., rituximab), anti-IL-12 monoclonal antibody, anti-IL-15 monoclonal antibody, CDP 484, CDP 870, chemokine receptor antagonists, selective iNOS inhibitors, p38 kinase inhibitors, integrin antagonists, angiogenesis inhibitors, and TMI-1 dual inhibitors. Further anti-inflammatory agents include meloxicam, rofecoxib, celecoxib, etoricoxib, parecoxib, valdecoxib and tilicoxib.

NSAIDs include, but are not limited to, ibuprofen, flurbiprofen, naproxen or naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. One class of NSAIDs consists of compounds that inhibit cyclooxygenase (COX) enzymes; such compounds include celecoxib and rofecoxib. NSAIDs further include salicylates such as acetylsalicylic acid or aspirin, sodium salicylate, choline and magnesium salicylates, and salsalate, as well as corticosteroids such as cortisone, dexamethasone, methylprednisolone, prednisolone, prednisolone sodium phosphate, and prednisone.

Suitable dosages for $P2X_7$ modulator within such combination therapy are generally as described above. Dosages and methods of administration of anti-inflammatory agents can be found, for example, in the manufacturer's instructions in the *Physician's Desk Reference*. In certain embodiments, the combination administration of a modulator with an anti-inflammatory agent results in a reduction of the dosage of the anti-inflammatory agent required to produce a therapeutic effect (i.e., a decrease in the minimum therapeutically effective amount). Thus, preferably, the dosage of anti-inflammatory agent in a combination or combination treatment method is less than the maximum dose advised by the manufacturer for administration of the anti-inflammatory agent without combination administration of a modulator. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a modulator. It will be apparent that the dosage amount of modulator component of the combination needed to achieve the desired effect may similarly be reduced by the co-administration of the anti-inflammatory agent.

In certain preferred embodiments, the combination administration of a modulator with an anti-inflammatory agent is accomplished by packaging one or more modulators and one or more anti-inflammatory agents in the same package, either in separate containers within the package or in the same contained as a mixture of one or more modulators and one or more anti-inflammatory agents. Preferred mixtures are formulated for oral administration (e.g., as pills, capsules, tablets or the like). In certain embodiments, the package comprises a label bearing indicia indicating that the one or more modulators and one or more anti-inflammatory agents are to be taken together for the treatment of an inflammatory pain condition.

Within further aspects, modulators provided herein may be used in combination with one or more additional pain relief medications. Certain such medications are also anti-inflammatory agents, and are listed above. Other such medications are analgesic agents, including narcotic agents which typically act at one or more opioid receptor subtypes (e.g., μ, κ and/or δ), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanil, alphaprodine, anileridine, bezitramide, buprenorphine, butorphanol, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, nalbuphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, sulfentanyl, thebaine and pharmaceutically acceptable salts and hydrates of the foregoing agents.

Other examples of narcotic analgesic agents include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine, methylpromide, morphine methylsulfonate, morphine-N-oxide, myrophin, naloxone, naltyhexone, nicocodeine, nicomorphine, noracymethadol, norlevorphanol, normethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example acetaminophen (paracetamol); aspirin and other NSAIDs described above; NR2B antagonists; bradykinin antagonists; anti-migraine agents; anticonvulsants such as oxcarbazepine and carbamazepine; antidepressants (such as TCAs, SSRIs, SNRIs, substance P antagonists, etc.); spinal blocks; pentazocine/naloxone; meperidine; levorphanol; buprenorphine; hydromorphone; fentanyl; sufentanyl; oxycodone; oxycodone/acetaminophen, nalbuphine and oxymorphone. Still further analgesic agents include CB2-receptor agonists, such as AM1241, capsaicin receptor antagonists and compounds that bind to the α2δ subunit of voltage-gated calcium channels, such as gabapentin and pregabalin.

Representative anti-migraine agents for use in combination with a modulator provided herein include CGRP antagonists, capsaicin receptor antagonists, ergotamines and 5-$HT_1$ agonists, such as sumatripan, naratriptan, zolmatriptan and rizatriptan.

Within still further aspects, modulators provided herein may be used, for example, in the treatment of pulmonary disorders such as asthma, in combination with one or more beta(2)-adrenergic receptor agonists or leukotriene receptor antagonists (e.g., agents that inhibits the cysteinyl leukotriene $CysLT_1$ receptor). $CysLT_1$ antagonists include montelukast, zafirlukast, and pranlukast.

For retinal neuroprotection and treatment of ocular disorders, $P2X_7$ modulators may be administered to the eye in combination with, for example, one or more of an agent that inhibits ATP release, an agent that enhances conversion of ATP to adenosine and/or an agent that inhibits $Ca^{+2}$ influx into retinal ganglion cells. Such agents include, for example, adenosine $A_3$ receptor agonists, adenosine $A_1$ receptor agonists, ectonucleotidase agonists, $Ca^{+2}$ chelating agents and NMDA receptor antagonists.

Suitable dosages for $P2X_7$ modulator within such combination therapy are generally as described above. Dosages and methods of administration of other pain relief medications can be found, for example, in the manufacturer's instructions in the *Physician's Desk Reference*. In certain embodiments, the combination administration of a modulator with one or more additional pain medications results in a reduction of the dosage of each therapeutic agent required to produce a therapeutic effect (e.g., the dosage or one or both agent may less than ¾, less than ½, less than ¼ or less than 10% of the maximum dose listed above or advised by the manufacturer).

For use in combination therapy, pharmaceutical compositions as described above may further comprise one or more additional medications as described above. In certain such compositions, the additional medication is an analgesic. Also provided herein are packaged pharmaceutical preparations comprising one or more modulators and one or more additional medications (e.g., analgesics) in the same package. Such packaged pharmaceutical preparations generally include (i) a container holding a pharmaceutical composition that comprises at least one modulator as described herein; (ii) a container holding a pharmaceutical composition that comprises at least one additional medication (such as a pain relief and/or anti-inflammatory medication) as described above and (iii) instructions (e.g., labeling or a package insert) indicating that the compositions are to be used simultaneously, separately or sequentially for treating or preventing a condition responsive to $P2X_7$ modulation in the patient (such as a condition in which pain and/or inflammation predominates).

Within separate aspects, the present invention provides a variety of non-pharmaceutical in vitro and in vivo uses for the modulator compounds provided herein. For example, such compounds may be labeled and used as probes for the detection and localization of $P2X_7$ (in samples such as cell preparations or tissue sections, preparations or fractions thereof). In addition, modulators provided herein that comprise a suitable reactive group (such as an aryl carbonyl, nitro or azide group) may be used in photoaffinity labeling studies of receptor binding sites. In addition, modulators provided herein may be used as positive controls in assays for receptor activity or as radiotracers (e.g., in receptor mapping procedures). For example, a modulator compound may be labeled using any of a variety of well known techniques (e.g., radiolabeled with a radionuclide such as tritium, as described herein), and used as a probe for receptor autoradiography (receptor mapping) of $P2X_7$ in cultured cells or tissue samples, which may be performed as described by Kuhar in sections 8.1.1 to 8.1.9 of Current Protocols in Pharmacology (1998) John Wiley & Sons, New York, which sections are incorporated herein by reference. Such receptor mapping procedures also include methods that can be used to characterize $P2X_7$ in living subjects, such as positron emission tomography (PET) imaging or single photon emission computerized tomography (SPECT).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass spectroscopy data provided herein is Electrospray MS, obtained in positive ion mode. Unless otherwise specified, such data is obtained using a Micromass Time-of-Flight LCT (Waters Corp.; Milford, Mass.), equipped with a Waters 600 pump (Waters Corp.), Waters 996 photodiode array detector (Waters Corp.), and a Gilson 215 autosampler (Gilson, Inc.; Middleton, Wis.). MassLynx™ (Waters Corp.) version 4.0 software with OpenLynx Global Server™, OpenLynx™ and AutoLynx™ processing is used for data collection and analysis. MS conditions are as follows: capillary voltage=3.5 kV; cone voltage=30 V, desolvation and source temperature=350° C. and 120° C., respectively; mass range=181-750 with a scan time of 0.22 seconds and an interscan delay of 0.05 seconds.

For data marked with a "§," mass spectroscopy data is obtained using a Waters ZMD II Mass Spectrometer (Waters Corp.), equipped with a Waters 600 pump (Waters Corp.), Waters 996 photodiode array detector (Waters Corp.), and a Gilson 215 autosampler (Gilson, Inc.; Middleton, Wis.). MassLynx™ (Waters Corp.) version 4.0 software with OpenLynx Global Server™, OpenLynx™ and AutoLynx™ processing is used for data collection and analysis. MS conditions are as follows: capillary voltage=3.5 kV; cone voltage=30 V, desolvation and source temperature=250° C. and 100° C., respectively; mass range=100-800 with a scan time of 0.5 seconds and an interscan delay of 0.1 seconds.

For either method, sample volume of 1 microliter is injected onto a 50×4.6 mm Chromolith SpeedROD RP-18e column (Merck KGaA, Darmstadt, Germany), and eluted using a 2-phase linear gradient at a flow rate of 6 ml/min. Sample is detected using total absorbance count over the 220-340 nm UV range. The elution conditions are: Mobile Phase A—95% water, 5% MeOH with 0.05% TFA; Mobile Phase B—5% water, 95% MeOH with 0.025% TFA. The following gradient is used: 0-0.5 min 10-100% B, hold at 100% B to 1.2 min, return to 10% B at 1.21 min. Inject to inject cycle is 2.15 min.

Where indicated, retention times ($R_T$) are provided in minutes.

Example 1

Preparation of Representative Heteroaryl Amide Analogues

This Example illustrates the preparation of representative heteroaryl amide analogues of Formula I, as well as certain intermediates useful in the preparation of such compounds. The P2X$_7$ IC$_{50}$, determined as described in Example 4A, is 2 micromolar or less for Compounds 1-15.

A. 4-[(Adamantan-1-ylmethyl)carbamoyl]pyrazolo[1,5-a]pyridine-2-carboxylic acid ethyl ester (Compound 1)

Step 1. 4-Hydroxymethylpyrazolo[1,5-a]pyridine-2,3-dicarboxylic acid dimethyl ester

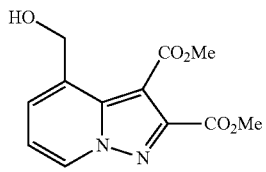 [SMILES: COC(=O)c1nn2cccc(CO)c2c1C(=O)OC]

A solution of O-mesitylenesulfonylhydroxylamine, ~30-35% water, (14.5 g, 52 mmol) and CH$_2$Cl$_2$ (100 mL) is added to a solution of 3-pyridylcarbinol (5.0 mL, 52 mmol) and CH$_2$Cl$_2$ (100 mL) at 0° C. dropwise over 40 min. After 30 min at 0° C., the ice bath is removed and the solution is stirred at ambient temperature for 20 min. The volatiles are removed under reduced pressure to afford N-amino-3-hydroxymethylpyridinium mesityl sulfonate as a yellow oil. DMF (100 mL) and K$_2$CO$_3$ (15 g, 110 mmol) are added. The dark brown mixture is cooled in a water bath. Dimethyl acetylenedicarboxylate (6.9 mL, 56 mmol) are added dropwise over 10 min. After 15 min, the water bath is removed and the mixture is left to vigorously stir under air for 18 h. After filtering through Celite (CH$_2$Cl$_2$ rinse), the volatiles are removed under reduced pressure. The residue is slurried in EtOAc and the mixture is filtered through Celite (EtOAc rinse). The volatiles are removed under reduced pressure to afford a dark brown oil. Purification by flash column chromatography (2:1 hexanes:EtOAc to 1:1 hexanes:EtOAc) affords the title compound as a light yellow solid. LC-MS m/z (M+Na$^+$): 287.08$^§$.

Step 2. 4-Hydroxymethylpyrazolo[1,5-a]pyridine-2-carboxylic acid ethyl ester

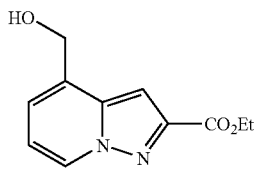

50% Aqueous H$_2$SO$_4$ (400 mL) is added to 4-hydroxymethylpyrazolo[1,5-a]pyridine-2,3-dicarboxylic acid dimethyl ester (11.6 g, 43.9 mmol) under air. The mixture is warmed to 80° C. After 3.5 h, the solution is transferred to a 2 L flask and cooled to 0° C. The solution is neutralized with 10 N aq. NaOH. The resulting slurry is acidified to pH 3 with 1 M aq. HCl. The volatiles are removed under reduced pressure. The residue is washed with 30% EtOH in CH$_2$Cl$_2$. The volatiles are removed under reduced pressure to afford the title compound as a tan solid. LC-MS m/z (M+H$^+$): 193.07.

Acetyl chloride (9.5 mL, 130 mmol) is added to absolute ethanol (200 mL). After 30 min, the solution is poured into the flask containing 4-hydroxymethyl-pyrazolo[1,5-a]pyridine-2-carboxylic acid. The mixture is warmed to 50° C. for 3.5 h. After cooling to rt, the mixture is made basic with dropwise addition of sat. aq. NaHCO$_3$. The volatiles are removed under reduced pressure. The aqueous solution is extracted with EtOAc. The organics are dried over Na$_2$SO$_4$, filtered, and concentrated to afford the title compound as a tan powder. LC-MS m/z (M+Na$^+$): 242.98$^§$.

Step 3. Pyrazolo[1,5-a]pyridine-2,4-dicarboxylic acid 2-ethyl ester

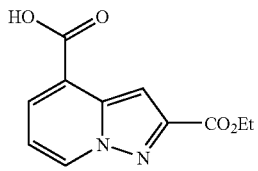 [SMILES: CCOC(=O)c1cc2c(C(=O)O)cccn2n1]

A 2.65 M solution of the Jones reagent (28 mL) is added dropwise over 40 min to a solution of 4-hydroxymethylpyrazolo[1,5-a]pyridine-2-carboxylic acid ethyl ester (5.30 g, 24.1 mmol) and acetone (240 mL) under air cooled by a water bath. After 20 min, isopropanol (3 mL) is added dropwise. After stirring for 30 min, the blue-green mixture is filtered (acetone rinse). The organics are concentrated under reduced pressure. The residue is dissolved in water. Et$_2$O is added and the mixture is stirred for 15 min. The resulting solid is collected by filtration. The filtrate is dried to afford the title compound as a tan solid. LC-MS m/z (M+Na$^+$): 257.02$^§$.

Step 4. 4-[(Adamantan-1-ylmethyl)carbamoyl]pyrazolo[1,5-a]pyridine-2-carboxylic acid ethyl ester Compound 1

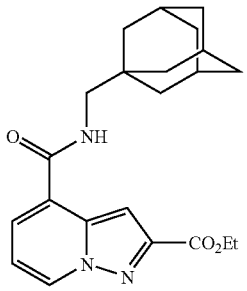

BOP (11 g, 24 mmol) is added to a slurry of pyrazolo[1,5-a]pyridine-2,4-dicarboxylic acid 2-ethyl ester (5.6 g, 24 mmol), adamantan-1-ylmethylamine (4.4 g, 27 mmol), iPr$_2$NEt (21 mL, 120 mmol), and DMF (240 mL) under N$_2$. The reaction vessel is sealed and the mixture is left to stir for 15 h. EtOAc (200 mL) is added. The solution is washed with 50% sat. aq. NH$_4$Cl (2×500 mL). The aqueous phases are extracted with EtOAc (3×200 mL). The combined organics are dried over Na$_2$SO$_4$, filtered, and concentrated. Purification by flash column chromatography (2:1 hexanes:EtOAc to 1:1 hexanes:EtOAc) affords the title compound as a tan solid. $^1$H NMR (400 MHz, CDCl$_3$) δ: 8.62 (d, 1H), 7.60 (d, 1H), 7.44 (s, 1H), 7.00 (t, 1H), 6.23 (bs, 1H), 4.48 (q, 2H), 3.23 (d, 2H), 1.98-2.07 (m, 3H), 1.57-1.78 (m, 12H), 1.45 (t, 3H). LC-MS m/z (M+H$^+$): 382.2; R$_T$=1.09 min.

B. N-(adamantan-1-ylmethyl)-2-{[(3R)-3-aminopyrrolidin-1-yl]carbonyl}pyrazolo[1,5-a]pyridine-4-carboxamide (Compound 2)

Step 1. 4-[(Adamantan-1-ylmethyl)carbamoyl]pyrazolo[1,5-a]pyridine-2-carboxylic acid

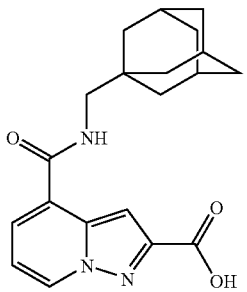 [SMILES: O=C(O)c1cc2c(C(=O)NCC34CC5CC(CC(C5)C3)C4)cccn2n1]

3 M Aqueous KOH (2.6 mL) is added to a mixture of 4-[(adamantan-1-ylmethyl)carbamoyl]-pyrazolo[1,5-a]pyridine-2-carboxylic acid ethyl ester (503 mg, 1.32 mmol) and EtOH (6.6 mL). After 4 h, the volatiles are removed under reduced pressure. The aqueous residue is diluted with water (2 mL) and then acidified with 1 M aq. HCl to ~pH 2. The solids are collected by filtration and then dried to afford the title compound as a light yellow powder. $^1$H NMR (400 MHz, ((CD$_3$)$_2$SO) δ: 8.86 (d, 1H), 8.50 (t, 1H), 7.71 (d, 1H), 7.26 (s, 1H), 7.12 (t, 1H), 3.00 (d, 2H), 1.88-1.98 (m, 3H), 1.48-1.69 (m, 12H). LC-MS m/z (M+H$^+$): 354.09.

Step 2. N-(adamantan-1-ylmethyl)-2-{[(3R)-3-aminopyrrolidin-1-yl]carbonyl}pyrazolo[1,5-a]pyridine-4-carboxamide Compound 2

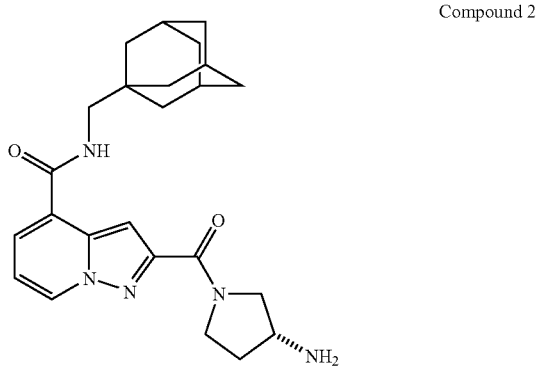 [SMILES: N[C@@H]1CCN(C(=O)c2cc3c(C(=O)NCC45CC6CC(CC(C6)C4)C5)cccn3n2)C1]

BOP (680 mg, 1.5 mmol) is added to a mixture of 4-[(adamantan-1-ylmethyl)carbamoyl]-pyrazolo[1,5-a]pyridine-2-carboxylic acid (417 mg, 1.18 mmol), tert-butyl (R)-pyrrolidin-3-ylcarbamate (242 mg, 1.30 mmol), iPr$_2$Net (620 µL, 3.6 mmol) and DMF (12 mL) under N$_2$. The reaction vessel is sealed and the solution is left to stir for 20 h. EtOAc (50 mL) is added. The solution is washed with H$_2$O (2×50 mL) and brine (50 mL). The organics are dried over Na$_2$SO$_4$, filtered, and concentrated. Purification by flash column chromatography (2% MeOH in CH$_2$Cl$_2$) affords (R)-(1-{4-[(adamantan-1-ylmethyl)carbamoyl]pyrazolo[1,5-a]-pyridine-2-carbonyl}pyrrolidin-3-yl)carbamic acid tert-butyl ester as a tan solid. MeOH (6.8 mL) and 4 M HCl in dioxane (1.7 mL) are added. After 20 h, the volatiles are removed under reduced pressure to afford a light tan solid. 15% Aqueous K$_2$CO$_3$ (50 mL) is added. The solution is extracted with EtOAc (5×50 mL). The combined organics are dried over Na$_2$SO$_4$, filtered, and concentrated. Purification by flash column chromatography (1% NH$_4$OH in 9:1 CH$_2$Cl$_2$:MeOH) affords the title compound as a tan foam. $^1$H NMR (300 MHz, CDCl$_3$) δ: 8.48 (ddd, 1H), 7.62 (dd, 1H), 7.22 (dd, 1H), 6.87 (t, 1H), 6.50 (bt, 1H), 3.42-4.20 (m, 5H), 3.20 (d, 2H), 2.14 (septet, 1H), 1.96-2.04 (m, 3H), 1.55-1.88 (m, 12H). LC-MS m/z (M+H$^+$): 422.3; R$_T$=1.2 min.

C. N-(adamantan-1-ylmethyl)-2-(hydroxymethyl)pyrazolo[1,5-a]pyridine-4-carboxamide (Compound 3)

Compound 3

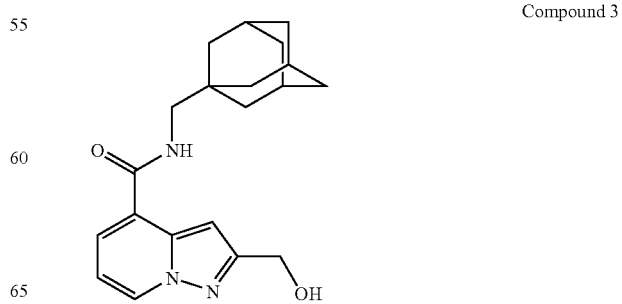

A 2.0 M solution of LiBH₄ in THF (5.8 mL) is added dropwise to a solution of 4-[(adamantan-1-ylmethyl)carbamoyl]pyrazolo[1,5-a]pyridine-2-carboxylic acid ethyl ester (2.01 g, 5.27 mmol) and THF (50 mL) at 0° C. under N₂. After 10 min, the ice bath is removed. After 3 h, additional 2.0 M solution of LiBH₄ in THF (2.0 mL) is added. After 4 h, sat. aq. NH₄Cl is added dropwise. The volatiles are removed under reduced pressure. H₂O (20 mL) is added and the solids are collected by filtration. The solids are slurried in MeOH (75 mL) and warmed to 50° C. for 4 h. The volatiles are removed under reduced pressure to afford the title compound as a light tan solid. ¹H NMR (300 MHz, CDCl₃) δ: 8.58 (ddd, 1H), 7.56 (dd, 1H), 6.92 (t, 1H), 6.90 (s, 1H), 4.80 (s, 2H), 3.12 (s, 2H), 1.96-2.04 (m, 3H), 1.62-1.84 (m, 12H). LC-MS m/z (M+H⁺): 340.3; $R_T$=1.27 min.

D. N-(adamantan-1-ylmethyl)-2-{[(3R)-3-aminopyrrolidin-1-yl]methyl}pyrazolo[1,5-a]pyridine-4-carboxamide (Compound 4)

Step 1. Methanesulfonic acid 4-[(adamantly-1-ylmethyl)carbamoyl]pyrazolo[1,5-a]pyridine-2-ylmethyl ester

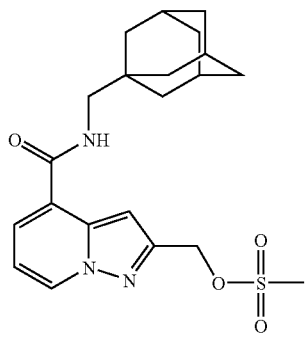 [SMILES: CS(=O)(=O)OCc1cc2c(C(=O)NCC34CC5CC(CC(C5)C3)C4)cccn2n1]

Methanesulfonyl chloride (140 μL, 1.2 mmol) is added to a slurry of 2-hydroxymethyl-pyrazolo[1,5-a]pyridine-4-carboxylic acid (adamantan-1-ylmethyl)amide (510 mg, 1.5 mmol) in THF (15 mL) and triethylamine (310 μL, 2.3 mmol) under N₂. After 1 h, the mixture is filtered (THF rinse). The volatiles are removed under reduced pressure to afford the title compound as a pale yellow solid. LC-MS m/z (M+Na⁺): 440.04.

Step 2. N-(adamantan-1-ylmethyl)-2-{[(3R)-3-aminopyrrolidin-1-yl]methyl}pyrazolo[1,5-a]pyridine-4-carboxamide Compound 4

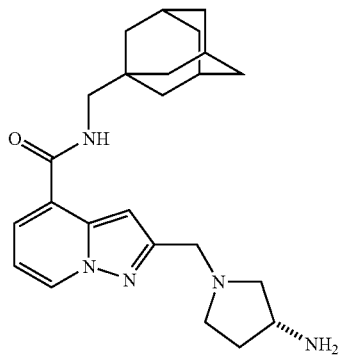

tert-Butyl (R)-pyrrolidin-3-ylcarbamate (420 mg, 2.3 mmol) is added to a mixture of methanesulfonic acid 4-[(adamantly-1-ylmethyl)carbamoyl]pyrazolo[1,5-a]pyridine-2-ylmethyl ester (630 mg, 1.5 mmol), K₂CO₃ (530 mg, 3.8 mmol) and DMF (15 mL) under N₂. After 3 h, H₂O (50 mL) is added. The solution is extracted with EtOAc (50 mL). The organics are washed with H₂O (50 mL) and brine (50 mL) and then dried over Na₂SO₄, filtered and concentrated. Purification by flash column chromatography (1% NH₄OH in 95:5 CH₂Cl₂:MeOH) affords (R)-(1-{4-[(adamantan-1-ylmethyl)carbamoyl]pyrazolo[1,5-a]pyridin-2-ylmethyl}pyrrolidin-3-yl)carbamic acid tert-butyl ester as a tan foam. The foam is dissolved in MeOH (12 mL) and 4 M HCl in dioxane (3.0 mL). After 6 h, the volatiles are removed under reduced pressure to afford a tan foam. 15% Sat. aq. K₂CO₃ (50 mL) is added and the mixture is extracted with EtOAc (5×25 mL). The combined organics are dried over Na₂SO₄, filtered and concentrated. Purification by flash column chromatography (1% NH₄OH in 9:1 CH₂Cl₂:MeOH to 2% NH₄OH in 4:1 CH₂Cl₂:MeOH) affords the title compound as a tan foam. ¹H NMR (300 MHz, CDCl₃) δ: 8.49 (d, 1H), 7.54 (dd, 1H), 6.77 (s, 1H), 6.75 (t, 1H), 6.30 (bt, 1H), 4.85 (dd, 2H), 3.48-3.58 (m, 1H), 3.20 (d, 2H), 2.77-2.88 (m, 2H), 2.52 (m, 1H), 2.43 (dd, 1H), 2.14-2.28 (m, 1H), 1.45-2.05 (m, 18H). LC-MS m/z (M+H⁺): 408.3; $R_T$=1.15 min.

E. N-(adamantan-1-ylmethyl)-2-(cyanomethyl)pyrazolo[1,5-a]pyridine-4-carboxamide (Compound 5)

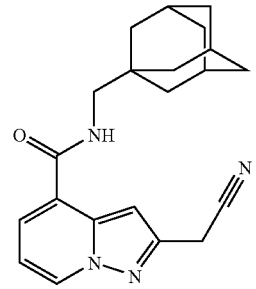

Compound 5

Sodium cyanide (520 mg, 11 mmol) is added to a solution of methanesulfonic acid 4-[(adamantly-1-ylmethyl)carbamoyl]pyrazolo[1,5-a]pyridine-2-ylmethyl ester (720 mg, 2.1 mmol) and DMF (20 mL) under N₂. The mixture is warmed to 60° C. for 1 h. After cooling to rt, the mixture is diluted with EtOAc (50 mL) and then washed with 50% sat. aq. NaHCO₃ (2×50 mL) and brine (50 mL) The organics are dried over Na₂SO₄, filtered and concentrated. Purification by flash column chromatography (2:1 EtOAc:hexanes) affords the title compound as a tan foam. ¹H NMR (300 MHz, CDCl₃) δ: 8.48 (d, 1H), 7.54 (dd, 1H), 6.91 (s, 1H), 6.83 (t, 1H), 6.26 (bs, 1H), 3.97 (s, 2H), 3.20 (d, 2H), 1.97-2.05 (m, 3H), 1.55-1.79 (m, 12H). LC-MS m/z (M+H⁺): 349.3; $R_T$=1.28 min.

F. {4-[(Adamantan-1-ylmethyl)carbamoyl]pyrazolo[1,5-a]pyridin-2-yl}acetic acid (Compound 6)

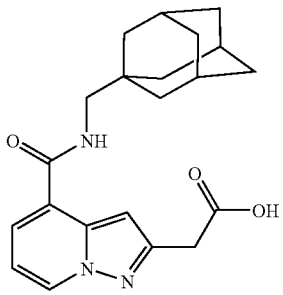

Compound 6

A solution of conc. HCl (2.3 mL) and AcOH (4.6 mL) is added to 2-cyanomethylpyrazolo[1,5-a]pyridine-4-carboxylic acid (adamantan-1-ylmethyl)amide. The solution is warmed to 60° C. for 20 h. The volatiles are removed under reduced pressure, and the residue is dissolved in 1 M aq. NaOH (10 mL). The solution is washed with Et$_2$O (20 mL). The aqueous layer is acidified to ~pH 3 with 1 M aq. HCl. The mixture is filtered and the filtrate dried to afford the title compound as a light tan solid. $^1$H NMR (400 MHz, ((CD$_3$)$_2$SO) δ: 8.71 (d, 1H), 8.40 (bt, 1H), 7.60 (d, 1H), 6.90 (t, 1H), 6.79 (s, 1H), 3.75 (s, 2H), 2.99 (d, 2H), 1.88-1.96 (m, 3H), 1.46-1.70 (m, 12H). LC-MS m/z+H$^+$): 368.3; R$_T$=1.27 min.

G. N-(adamantan-1-ylmethyl)-2-{2-[(3R)-3-aminopiperidin-1-yl]-2-oxoethyl}pyrazolo[1,5-a]pyridine-4-carboxamide (Compound 7)

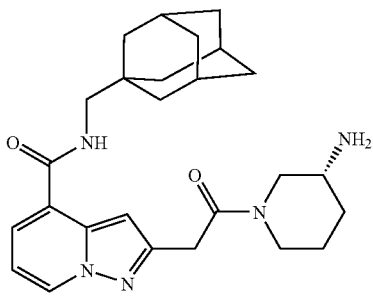

Compound 7

BOP (250 mg, 570 mmol) is added to a mixture of {4-[(adamantan-1-ylmethyl)carbamoyl]-pyrazolo[1,5-a]pyridin-2-yl}acetic acid (160 mg, 435 µmol), tert-butyl (R)-piperidin-3-ylcarbamate (96 mg, 480 µmol), iPr$_2$NEt (230 µL, 1.3 mmol), and DMF (2.2 mL) under N$_2$. The reaction vessel is sealed and the solution is left to stir for 15 h. EtOAc (25 mL) is added. The solution is washed with H$_2$O (2×25 mL) and brine (25 mL). The organics are dried over Na$_2$SO$_4$, filtered and concentrated. Purification by flash column chromatography (95:5 CH$_2$Cl$_2$:MeOH) affords (R)-(1-{4-[(adamantan-1-ylmethyl)carbamoyl]pyrazolo[1,5-a]pyridin-2-yl}acetyl)piperidin-3-yl]carbamic acid tert-butyl ester as an orange foam. MeOH (4.2 mL) and 4 M HCl in dioxane (1.1 mL) are added. After 16 h, the volatiles are removed under reduced pressure to afford a light tan solid. 15% Aqueous K$_2$CO$_3$ (30 mL) is added. The solution is extracted with EtOAc (3×30 mL). The combined organics are dried over Na$_2$SO$_4$, filtered and concentrated. Purification by flash column chromatography (1% NH$_4$OH in 9:1 CH$_2$Cl$_2$:MeOH) affords the title compound as a tan foam. $^1$H NMR (400 MHz, CDCl$_3$) δ: 8.46-8.64 (m, 1H), 7.44 (bs, 1H), 6.68-6.80 (m, 2H), 3.86-4.17 (m, 3H), 3.38-3.61 (m, 3H), 3.12-3.25 (m, 3H), 1.40-2.04 (m, 19H). LC-MS m/z (M+H$^+$): 450.3; R$_T$=1.17.

H. {4-[(Adamantan-1-ylmethyl)carbamoyl]pyrazolo[1,5-a]pyridin-2-ylmethoxy}acetic acid ethyl ester (Compound 8)

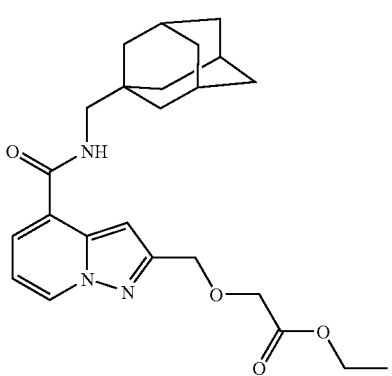

Compound 8

A 1.0 M solution of tBuOK in THF (0.3 mL) is added to a mixture of 2-hydroxymethyl-pyrazolo[1,5-a]pyridine-4-carboxylic acid (adamantan-1-ylmethyl)amide (73 mg, 210 µmol) and DMF (1 mL) at 0° C. under N$_2$. After 5 min, ethyl bromoacetate (30 µL, 280 µmol) is added. The cold bath is removed and the mixture is left to stir for 23 h. 50% Sat. aq. NaHCO$_3$ is added and the solution is extracted with EtOAc (20 mL). The organics are dried over Na$_2$SO$_4$, filtered and concentrated. Purification by PTLC (2:1 EtOAc:hexanes) affords the title compound as a pale yellow film. $^1$H NMR (400 MHz, CDCl$_3$) δ: 8.50 (dd, 1H), 7.57 (d, 1H), 6.88 (s, 1H), 6.81 (dt, 1H), 6.27 (bs, 1H), 4.88 (s, 2H), 4.22 (q, 2H), 4.19 (s, 2H), 3.21 (d, 2H), 1.94-2.04 (m, 3H), 1.56-1.78 (m, 12H), 1.28 (t, 3H). LC-MS m/z (M+H$^+$): 426.3; R$_T$=1.31.

I. {4-[(Adamantan-1-ylmethyl)carbamoyl]pyrazolo[1,5-a]pyridin-2-ylmethoxy}acetic acid (Compound 9)

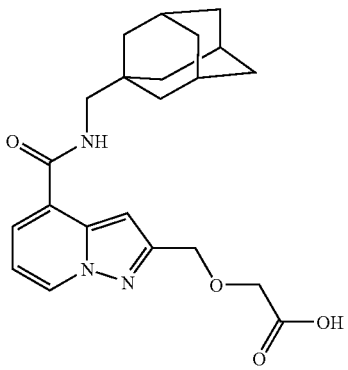

Compound 9

3 M Aq. KOH (50 μL) is added to a solution of {4-[(adamantan-1-ylmethyl)carbamoyl]-pyrazolo[1,5-a]pyridin-2-ylmethoxy}acetic acid ethyl ester (11 mg, 25 μmol) and EtOH (250 μL). After 18 h, the volatiles are removed under reduced pressure. The residue is diluted with $H_2O$ (0.3 mL) and then acidified with 1 M aq. HCl. The title compound is collected by filtration. $^1$H NMR (400 MHz, (($CD_3)_2SO$) δ: 8.74 (d, 1H), 8.42 (bs, 1H), 7.62 (d, 1H), 6.93 (t, 1H), 6.84 (s, 1H), 4.70 (s, 2H), 4.08 (s, 2H), 2.99 (d, 2H), 1.86-2.00 (m, 3H), 1.48-1.73 (m, 12H). LC-MS m/z (M+H$^+$): 398.3; $R_T$=1.26.

J. 4-(2-Adamantan-1-ylacetylamino)pyrazolo[1,5-a]pyridine-2-carboxylic acid ethyl ester (Compound 10)

Step 1.
4-Aminopyrazolo[1,5-a]pyridine-2,3-dicarboxylic acid dimethyl ester

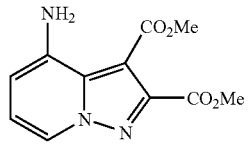 [SMILES: COC(=O)c1nn2cccc(N)c2c1C(=O)OC]

A solution of O-mesitylenesulfonylhydroxylamine, ~30-35% water, (14.5 g, 52 mmol) and $CH_2Cl_2$ (100 mL) is added to a solution of 3-aminopyridine (4.9 g, 52 mmol) and $CH_2Cl_2$ (100 mL) at 0° C. dropwise over 30 min. After 30 min at 0° C., the ice bath is removed and the solution is stirred at rt for 30 min. The volatiles are removed under reduced pressure to afford a yellow oil, N-amino-3-aminopyridinium mesityl sulfonate. DMF (100 mL) and $K_2CO_3$ (15 g, 110 mmol) are added. The dark brown mixture is cooled in a water bath. Dimethyl acetylenedicarboxylate (6.9 mL, 56 mmol) are added dropwise over 10 min. After 15 min, the water bath is removed and the mixture is left to vigorously stir under air for 66 h. The volatiles are removed under reduced pressure. The residue is slurried in MeOH and the mixture is filtered through Celite (MeOH rinse). The volatiles are removed under reduced pressure to afford a dark brown oil. 33% Sat. aq. $NaHCO_3$ (150 mL) is added and the solution is extracted with EtOAc (6×200 mL). The combined organics are dried over $Na_2SO_4$, filtered, and concentrated. Purification by flash column chromatography ($CH_2Cl_2$) affords the title compound as an orange-red oil. LC-MS m/z (M+Na$^+$): 272.01.

Step 2.
4-Aminopyrazolo[1,5-a]pyridine-2-carboxylic acid ethyl ester

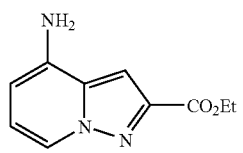 [SMILES: CCOC(=O)c1cc2c(N)cccn2n1]

50% Aqueous $H_2SO_4$ (60 mL) is added to 4-Aminopyrazolo[1,5-a]pyridine-2,3-dicarboxylic acid dimethyl ester (1.47 g, 5.90 mmol) under air. The mixture is warmed to 80° C. After 6.5 h, the solution is cooled to 0° C. and then neutralized with 10 N aq. NaOH. The resulting slurry is acidified to pH 3 with 1 M aq. HCl. The volatiles are removed under reduced pressure. The residue is washed with 30% EtOH in $CH_2Cl_2$. The volatiles are removed under reduced pressure to afford 4-aminopyrazolo[1,5-a]pyridine-2-carboxylic acid in $Na_2SO_4$. LC-MS m/z (M+H$^+$): 178.01. A solution of conc. $H_2SO_4$ (6.0 mL) and ethanol (120 mL) is added to the crude 4-aminopyrazolo[1,5-a]pyridine-2-carboxylic acid. The mixture is warmed to 75° C. for 3.5 h. After cooling to rt, the mixture is made basic with dropwise addition of sat. aq. $NaHCO_3$. The volatiles are removed under reduced pressure. The aqueous mixture is filtered (EtOAc rinse). The aqueous solution is extracted with EtOAc (3×250 mL). The combined organics are dried over $Na_2SO_4$, filtered, and concentrated to afford the title compound as dark brown solid. LC-MS m/z (M+Na$^+$): 228.03.

Step 3. 4-(2-Adamantan-1-ylacetylamino)pyrazolo[1,5-a]pyridine-2-carboxylic acid ethyl ester

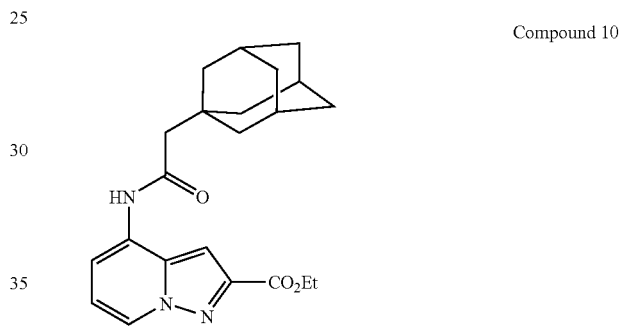

Compound 10

A 1.0 M solution of triethylamine in toluene (0.3 mL) is added to a solution of 1-adamantaneacetic acid (14 mg, 80 μmol) and 4-aminopyrazolo[1,5-a]pyridine-2-carboxylic acid ethyl ester (12 mg, 60 μmol) in DMF (0.3 mL) under $N_2$. A solution of 2-chloro-1,3-dimethylimidazolinium chloride (20 mg, 120 μmol) in ACN (0.3 mL) is added. The reaction vessel is sealed and the mixture is warmed to 50° C. for 2 h. The mixture is cooled to rt. 50% Sat. aq. $NaHCO_3$ (2 mL) is added. The solution is extracted with Et OAc (2×1 mL). The combined organics are concentrated. Purification by preparative thin layer chromatography (2:1 hexanes:EtOAc) affords the title compound as a light tan solid. $^1$H NMR (400 MHz, $CDCl_3$) δ: 8.32 (d, 1H), 8.05 (d, 1H), 7.15 (s, 1H), 7.05 (s, 1H), 6.91 (t, 1H), 4.59 (q, 2H), 2.21 (s, 2H), 1.98-2.06 (m, 3H), 1.56-1.78 (m, 12H), 1.46 (t, 3H). LC-MS m/z (M+H$^+$): 382.10.

Example 2

Synthesis of Additional Representative Heteroaryl Amide Analogues

This Example illustrates the synthesis of additional representative heteroaryl amide analogues of Formula I, as well as certain intermediates useful in the preparation of such compounds.

A. 2-(2-Cyano-vinyl)-pyrazolo[1,5-a]pyridine-4-carboxylic acid (adamantan-1-ylmethyl)-amide (Compound 11)

Step 1. 2-Formyl-pyrazolo[1,5-a]pyridine-4-carboxylic acid (adaman-1-ylmethy)-amide

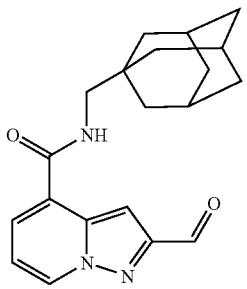 [SMILES: O=Cc1cc2c(C(=O)NCC34CC5CC(CC(C5)C3)C4)cccn2n1]

A solution of 4-[(adaman-1-ylmethyl)-carbomoy]-pyrazolo[1,5-a]pyridine-2-carboxylic acid ethyl ester (1.2 g, 3.1 mmol) in THF (25 mL) is cooled to −78° C. A solution of DIBAL-H (25 mL, 1M in hexane) is added dropwise. The mixture is stirred for 2 h at −78° C. A saturated Rochelle salt solution is added, and the mixture is stirred for 4 h at rt. The mixture is extracted with DCM (4×70 mL), and the organic layer is dried over $Na_2SO_4$. Purification by a flash column (eluted with 2-3% MeOH in DCM) gives the title compound.

Step 2. 2-(2-Cyano-vinyl)-pyrazolo[1,5-a]pyridine-4-carboxylic acid (adamantan-1-ylmethyl)-amide Compound 11

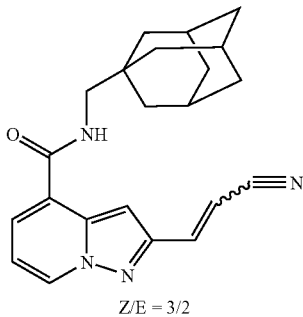

Z/E = 3/2

$Ph_3P$=CHCN (735 mg, 2.5 mmol) is added to a solution of 2-formyl-pyrazolo[1,5-a]pyridine-4-carboxylic acid (adaman-1-ylmethy)-amide (700 mg, 2.1 mmol) in THF at rt. The mixture is stirred for 2 h. The solvent is removed, and the resulting mixture of Z and E isomers is separated by a flash column (eluted with 20 to 30% EtOAc in hexane) into pure Z isomer, pure E isomer and a mixture (Z/E).

B. N-(adamantan-1-ylmethyl)-2-(2-cyanoethyl)pyrazolo[1,5-a]pyridine-4-carboxamide (Compound 12)

Compound 12

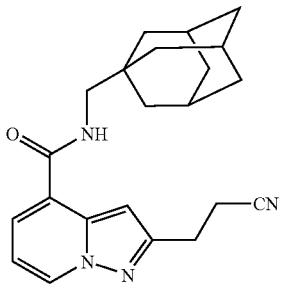

Pd/C (50 mg) is added to a solution of 2-(2-cyano-vinyl)-pyrazolo[1,5-a]pyridine-4-carboxylic acid (adamantan-1-ylmethyl)-amide in MeOH. The mixture is stirred under hydrogen balloon for 6 h. The mixture is filtered through celite and the celite and solvent are removed to give the title compound. LC-MS m/z (M+H$^+$): 363.

C. 2-[2-(1H-Tetrazol-5-yl)-ethyl]-pyrazolo[1,5-a]pyridine-4-carboxylic acid (adamantan-1-ylmethyl)-amide (Compound 13)

Compound 13

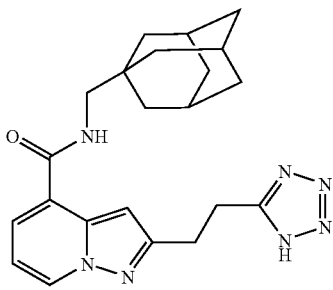

$NaN_3$ (65 mg, 0.48 mmol) and $NH_4Cl$ (26 mg, 0.48 mmol) are added to a solution of 2-(2-cyano-ethyl)-pyrazolo[1,5-a]pyridine-4-carboxylic acid (adamantan-1-ylmethyl)-amide (58 mg, 0.16 mmol) in DMSO at rt. The mixture is heated to 130° C. for 6 h. Additional $NaN_3$ (65 mg, 0.48 mmol) is added, and the mixture is heated for 14 h. The mixture is cooled to rt. $H_2O$ is added and pH is adjusted to about 7. The aqueous layer is extracted with EtOAc (3×15 mL), dried over $Na_2SO_4$ and the solvent is removed to dryness. The crude product is purified by PTLC (eluted with 2% MeOH in DCM) to give the title compound. $^1$H NMR (CDCl$_3$): 8.49-8.47 (d, 1H), 7.52-7.50 (d, 1H), 6.79-6.69 (t, 1H), 6.69 (s, 1H), 6.40 (b, 1H), 3.44-3.41 (m, 2H), 3.31-3.29 (m, 2H), 3.20-3.19 (m, 2H), 2.00 (b, 3H), 1.74-1.60 (m, 12H). LC-MS m/z (M+H$^+$): 406.07.

D. N-(adamantan-1-ylmethyl)-3-(3-cyanobenzoyl)indolizine-8-carboxamide (Compound 14)

Step 1. N-(Adamantan-1-ylmethyl)-2-methylnicotinamide

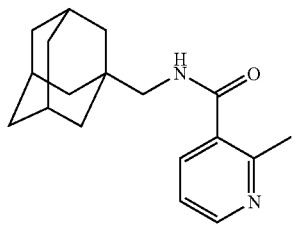 [SMILES: Cc1ncccc1C(=O)NCC12CC3CC(CC(C3)C1)C2]

To a mixture of 2-methylnicotinic acid (2.06 g, 15 mmol) in 40 mL of DMF is added sequentially diisopropylethylamine (5.2 mL, 30 mmol), 1-adamantan-1-ylmethanamine (2.5 g, 15 mmol), and benzotriazol-1-yloxytris-(dimethylamino)-phosphonium hexafluorophosphate (BOP reagent, 8 g, 18 mmol). The resulting mixture is stirred at rt for 17 h. The mixture is then poured into ice water (150 mL), and the precipitated solid is collected by vacuum filtration and dried in vacuo to afford the title compound as an off-white solid. Mass spec. (285.19, M+H).

Step 2. 3-[(Adamantan-1-ylmethyl)carbamoyl]-1-[2-(3-cyanophenyl)-2-oxoethyl]-2-methylpyridinium bromide

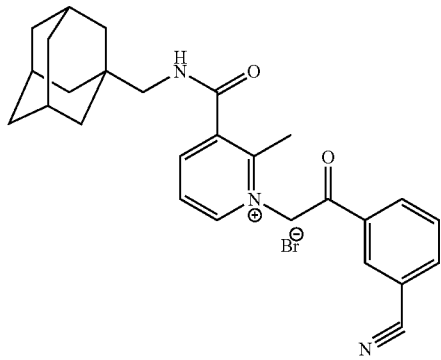 [SMILES: Cc1c(C(=O)NCC23CC4CC(CC(C4)C2)C3)ccc[n+]1CC(=O)c1cccc(C#N)c1 ; [Br-]]

A mixture of N-(adamantan-1-ylmethyl)-2-methylnicotinamide (300 mg, 1.05 mmol) and 3-(bromoacetyl)benzonitrile (235 mg, 1.05 mmol) in 10 mL of acetone is stirred at reflux for 2.5 days. After cooling to rt, most of the acetone is evaporated, and the remaining mixture is filtered. The collected solid is dried in vacuo to give the title compound as a white solid. $^1$H NMR (400 MHz, DMSO-$d_6$) δ 8.93 (1H, m), 8.86 (1H, bs), 8.62 (1H, d), 8.58 (1H, s), 8.33 (1H, d), 8.26 (1H, d), 8.14 (1H, t), 7.87 (1H, t), 6.60 (2H, s), 3.01 (2H, d), 2.67 (3H, s), 1.94 (3H, s), 1.63 (6H, m), 1.51 (6H, s).

Step 3. N-(Adamantan-1-ylmethyl)-3-(3-cyanobenzoyl)indolizine-8-carboxamide

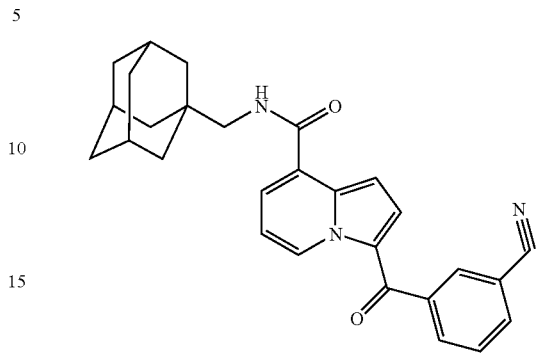

A mixture of 3-[(adamantan-1-ylmethyl)carbamoyl]-1-[2-(3-cyanophenyl)-2-oxoethyl]-2-methylpyridinium bromide (400 mg, 0.81 mmol) and N,N-dimethylformamide dimethyl acetal (0.22 mL, 1.62 mmol) in DMF (2.0 mL) is stirred at 110° C. for 3 h. The mixture is concentrated in vacuo and purified by column chromatography (gradient from $CH_2Cl_2$ to 10% EtOAc/$CH_2Cl_2$) to give the title compound as a yellow solid. $^1$H NMR (400 MHz, DMSO-$d_6$) δ 9.91 (1H, d), 8.53 (1H, t), 8.15 (1H, m), 8.05 (2H, m), 7.74 (1H, t), 7.66 (1H, dd), 7.44 (1H, d), 7.22 (1H, t), 6.95 (1H, d), 3.01 (2H, d), 1.93 (3H, s), 1.63 (6H, m), 1.52 (6H, s). Mass spec. (438.19, M+H).

E. N-(Adamantan-1-ylmethyl)-3-(3-carbamoylbenzoyl)indolizine-8-carboxamide (Compound 15)

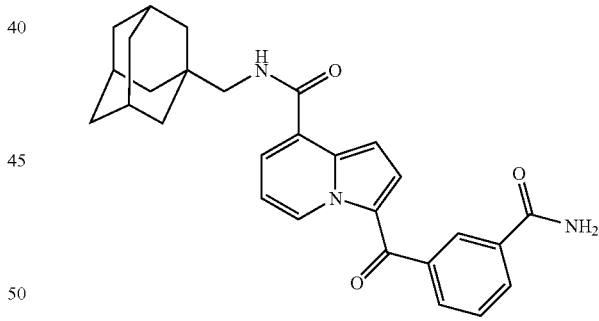

To ice cold $H_2SO_4$ (0.5 mL) is added in one portion N-(adamantan-1-ylmethyl)-3-(3-cyano-benzoyl)indolizine-8-carboxamide (50 mg, 0.11 mmol). The mixture is stirred at 0° C. until it becomes homogeneous, at which time the ice bath is removed and the reaction is warmed to rt. After stirring for 12 h, the mixture is cooled back to 0° C. and quenched with ice. The resulting solution is neutralized to pH=7-8 with 5N NaOH and extracted with EtOAc (20 mL). The EtOAc extract is dried ($Na_2SO_4$), filtered, and evaporated to give the title compound as a yellow solid. $^1$H NMR (400 MHz, DMSO-$d_6$) δ 9.92 (1H, d), 8.50 (1H, t), 8.22 (1H, s), 8.09 (2H, m), 7.88 (1H, d), 7.62 (2H, m), 7.48 (1H, s), 7.40 (1H, d), 7.19 (1H, t), 6.94 (1H, d), 3.00 (2H, s), 1.93 (3H, s), 1.62 (6H, m), 1.52 (6H, s). Mass spec. (456.21, M+H).

Example 3

Synthesis of Additional Representative Heteroaryl Amide Analogues

Using routine modifications, the starting materials may be varied and additional steps employed to produce other compounds provided herein. Compounds listed in Tables I and H are prepared using such methods. In the column of Table I labeled "IC$_{50}$," a "*" indicates that the IC$_{50}$ determined as described in Example 4A is 2 micromolar or less (i.e., the concentration of such compounds that is required to provide a 50% decrease in the fluorescence response of cells exposed to 80 μM of (2'(3')-O-(4-benzoyl-benzoyl)adenosine 5'-triphosephate is 2 micromolar or less).

Mass spectroscopy data is provided in Table I as (M+1) in the column headed "MS." The retention time, in minutes, is provided in the column headed R$_T$.

TABLE I

Representative Heteroaryl Amide Analogues

| Compound | | Name | MS | R$_T$ | IC$_{50}$ |
|---|---|---|---|---|---|
| 16 | 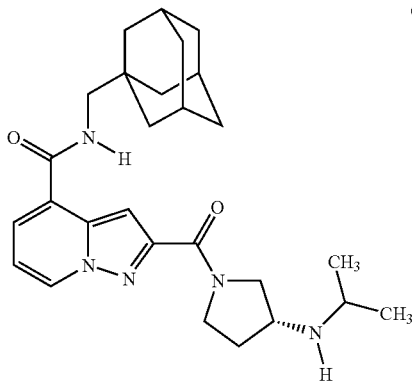 Chiral | N-(adamantan-1-ylmethyl)-2-{[(3R)-3-(isopropylamino)pyrrolidin-1-yl]carbonyl}pyrazolo[1,5-a]pyridine-4-carboxamide | 464.3 | 1.21 | * |
| 17 | 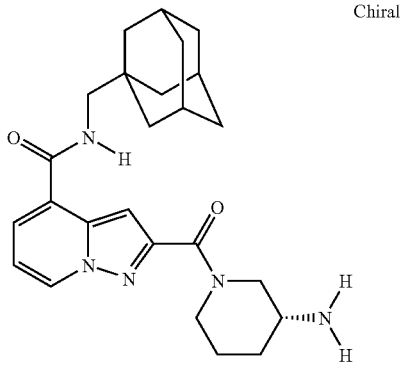 [SMILES: N[C@@H]1CCCN(C(=O)c2cc3c(C(=O)NCC45CC6CC(CC(C6)C4)C5)cccn3n2)C1] Chiral | N-(adamantan-1-ylmethyl)-2-{[(3R)-3-aminopiperidin-1-yl]carbonyl}pyrazolo[1,5-a]pyridine-4-carboxamide | 436.3 | 1.18 | * |
| 18 | 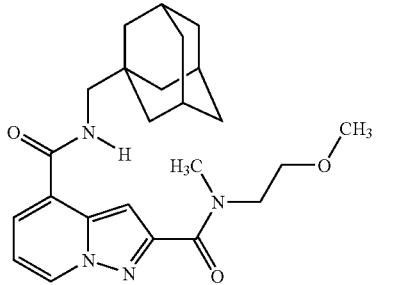 [SMILES: COCCN(C)C(=O)c1cc2c(C(=O)NCC34CC5CC(CC(C5)C3)C4)cccn2n1] | 4-N-(adamantan-1-ylmethyl)-2-N-(2-methoxyethyl)-2-N-methylpyrazolo[1,5-a]pyridine-2,4-dicarboxamide | 425.3 | 1.3 | * |

TABLE I-continued

Representative Heteroaryl Amide Analogues

| Compound | | Name | MS | $R_T$ | $IC_{50}$ |
|---|---|---|---|---|---|
| 19 | 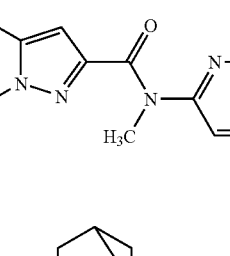 | 4-N-(adamantan-1-ylmethyl)-2-N-methyl-2-N-pyridin-2-ylpyrazolo[1,5-a]pyridine-2,4-dicarboxamide | 444.3 | 1.28 | * |
| 20 | 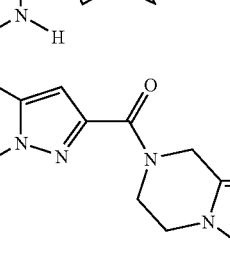 | N-(adamantan-1-ylmethyl)-2-(5,6-dihydroimidazo[1,5-a]pyrazin-7(8H)-ylcarbonyl)pyrazolo[1,5-a]pyridine-4-carboxamide | 459.3 | 1.2 | * |
| 21 | 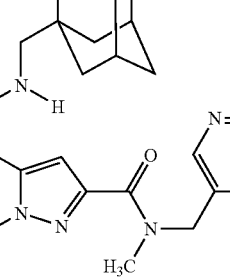 | 4-N-(adamantan-1-ylmethyl)-2-N-methyl-2-N-(pyridin-3-ylmethyl)pyrazolo[1,5-a]pyridine-2,4-dicarboxamide | 458.2 | 1.37 | * |
| 22 | 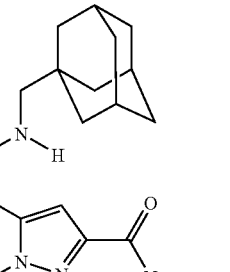 | N-(adamantan-1-ylmethyl)-2-(morpholin-4-ylcarbonyl)pyrazolo[1,5-a]pyridine-4-carboxamide | 423.2 | 1.44 | * |

TABLE I-continued

Representative Heteroaryl Amide Analogues

| Compound | Name | MS | R$_T$ | IC$_{50}$ |
|---|---|---|---|---|
| 23 | ethyl N-({4-[(adamantan-1-ylmethyl)carbamoyl]pyrazolo[1,5-a]pyridin-2-yl}carbonyl)-N-methylglycinate | 453.3 | 1.3 | * |
| 24 | N-(adamantan-1-ylmethyl)-2-(5,6-dihydro[1,2,4]triazolo[4,3-a]pyrazin-7(8H)-ylcarbonyl)pyrazolo[1,5-a]pyridine-4-carboxamide | 460.3 | 1.24 | * |
| 25 | N-(adamantan-1-ylmethyl)-2-(2-morpholin-4-yl-2-oxoethyl)pyrazolo[1,5-a]pyridine-4-carboxamide | 437.2 | 1.39 | * |
| 26 | 4-N-(adamantan-1-ylmethyl)-2-N-methyl-2-N-[(1-methyl-1H-imidazol-5-yl)methyl]pyrazolo[1,5-a]pyridine-2,4-dicarboxamide | 461.3 | 1.2 | * |

TABLE I-continued

Representative Heteroaryl Amide Analogues

| Compound | | | Name | MS | $R_T$ | $IC_{50}$ |
|---|---|---|---|---|---|---|
| 27 | 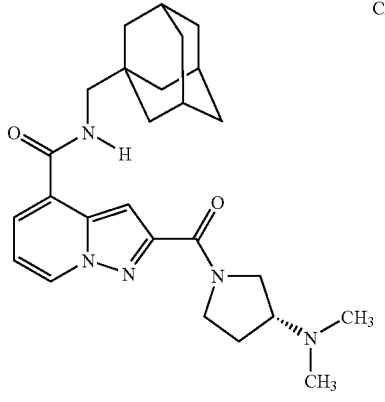 | Chiral | N-(adamantan-1-ylmethyl)-2-{[(3R)-3-(dimethylamino)pyrrolidin-1-yl]carbonyl}pyrazolo[1,5-a]pyridine-4-carboxamide | 450.3 | 1.17 | * |
| 28 | 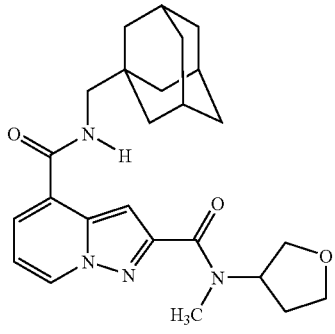 [SMILES: CN(C(=O)c1cc2c(C(=O)NCC34CC5CC(CC(C5)C3)C4)cccn2n1)C1CCOC1] | | 4-N-(adamantan-1-ylmethyl)-2-N-methyl-2-N-(tetrahydrofuran-3-yl)pyrazolo[1,5-a]pyridine-2,4-dicarboxamide | 437.3 | 1.28 | * |
| 29 | 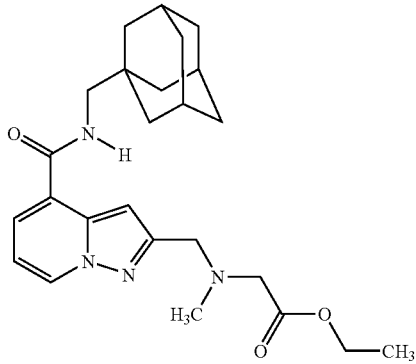 [SMILES: CCOC(=O)CN(C)Cc1cc2c(C(=O)NCC34CC5CC(CC(C5)C3)C4)cccn2n1] | | ethyl N-({4-[(adamantan-1-ylmethyl)carbamoyl]pyrazolo[1,5-a]pyridin-2-yl}methyl)-N-methylglycinate | 439.3 | 1.22 | * |
| 30 | 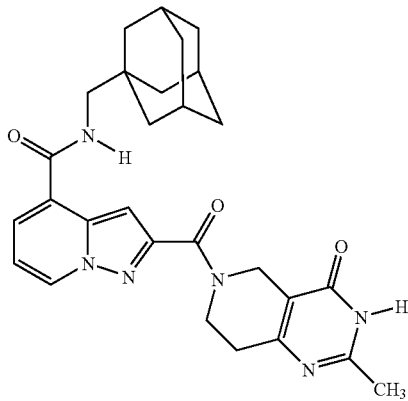 [SMILES: Cc1nc2c(c(=O)[nH]1)CN(C(=O)c1cc3c(C(=O)NCC45CC6CC(CC(C6)C4)C5)cccn3n1)CC2] | | N-(adamantan-1-ylmethyl)-2-[(2-methyl-4-oxo-3,5,7,8-tetrahydropyrido[4,3-d]pyrimidin-6(4H)-yl)carbonyl]pyrazolo[1,5-a]pyridine-4-carboxamide | 501.3 | 1.26 | * |

TABLE I-continued

Representative Heteroaryl Amide Analogues

| Compound | | Name | MS | $R_T$ | $IC_{50}$ |
|---|---|---|---|---|---|
| 31 | 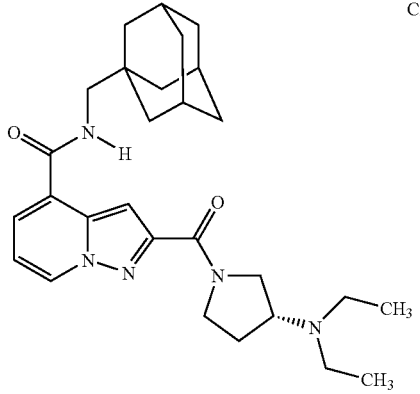 Chiral | N-(adamantan-1-ylmethyl)-2-{[(3R)-3-(diethylamino)pyrrolidin-1-yl]carbonyl}pyrazolo[1,5-a]pyridine-4-carboxamide | | | * |
| 32 | 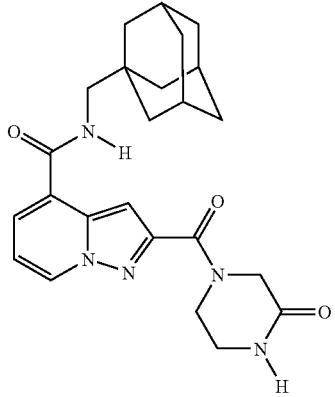 [SMILES: O=C1CN(C(=O)c2cc3c(C(=O)NCC45CC6CC(CC(C6)C4)C5)cccn3n2)CCN1] | N-(adamantan-1-ylmethyl)-2-[(3-oxopiperazin-1-yl)carbonyl]pyrazolo[1,5-a]pyridine-4-carboxamide | 436.2 | 1.26 | * |
| 33 | 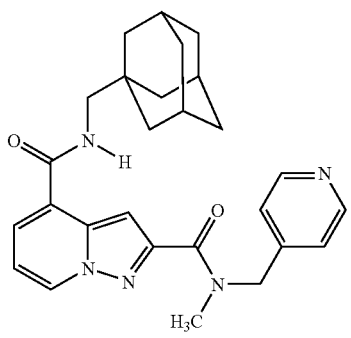 [SMILES: CN(Cc1ccncc1)C(=O)c1cc2c(C(=O)NCC34CC5CC(CC(C5)C3)C4)cccn2n1] | 4-N-(adamantan-1-ylmethyl)-2-N-methyl-2-N-(pyridin-4-ylmethyl)pyrazolo[1,5-a]pyridine-2,4-dicarboxamide | 458.2 | 1.31 | * |
| 34 | 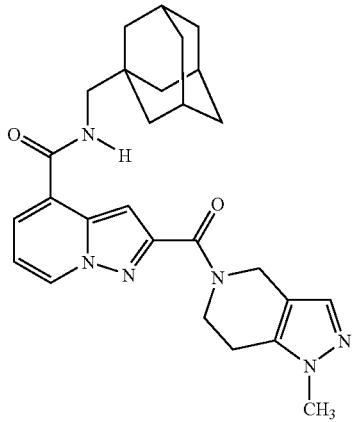 [SMILES: Cn1ncc2c1CCN(C(=O)c1cc3c(C(=O)NCC45CC6CC(CC(C6)C4)C5)cccn3n1)C2] | N-(adamantan-1-ylmethyl)-2-[(1-methyl-1,4,6,7-tetrahydro-5H-pyrazolo[4,3-c]pyridin-5-yl)carbonyl]pyrazolo[1,5-a]pyridine-4-carboxamide | 473.3 | 1.29 | * |

TABLE I-continued

Representative Heteroaryl Amide Analogues

| Compound | | Name | MS | $R_T$ | $IC_{50}$ |
|---|---|---|---|---|---|
| 35 | 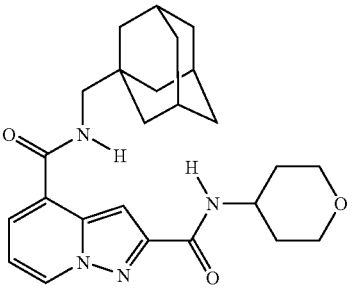 [SMILES: O=C(NC1CCOCC1)c1cc2c(C(=O)NCC34CC5CC(CC(C5)C3)C4)cccn2n1] | 4-N-(adamantan-1-ylmethyl)-2-N-(tetrahydro-2H-pyran-4-yl)pyrazolo[1,5-a]pyridine-2,4-dicarboxamide | 437.3 | 1.29 | * |
| 36 | 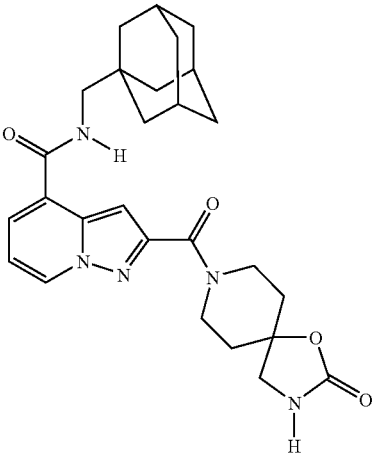 [SMILES: O=C1NCC2(CCN(C(=O)c3cc4c(C(=O)NCC56CC7CC(CC(C7)C5)C6)cccn4n3)CC2)O1] | N-(adamantan-1-ylmethyl)-2-[(2-oxo-1-oxa-3,8-diazaspiro[4.5]dec-8-yl)carbonyl]pyrazolo[1,5-a]pyridine-4-carboxamide | 492.3 | 1.26 | * |
| 37 | 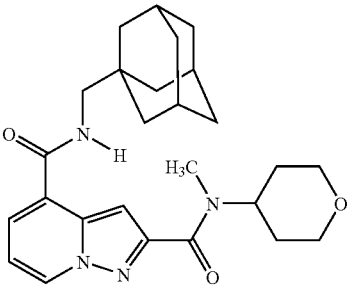 [SMILES: CN(C(=O)c1cc2c(C(=O)NCC34CC5CC(CC(C5)C3)C4)cccn2n1)C1CCOCC1] | 4-N-(adamantan-1-ylmethyl)-2-N-methyl-2-N-(tetrahydro-2H-pyran-4-yl)pyrazolo[1,5-a]pyridine-2,4-dicarboxamide | 451.3 | 1.3 | * |
| 38 | 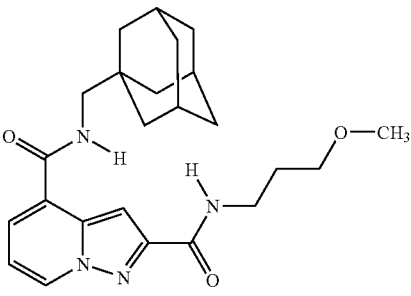 [SMILES: COCCCNC(=O)c1cc2c(C(=O)NCC34CC5CC(CC(C5)C3)C4)cccn2n1] | 4-N-(adamantan-1-ylmethyl)-2-N-(3-methoxypropyl)pyrazolo[1,5-a]pyridine-2,4-dicarboxamide | 425.3 | 1.3 | * |

TABLE I-continued

Representative Heteroaryl Amide Analogues

| Compound | Name | MS | R_T | IC_{50} |
|---|---|---|---|---|
| 39 | 4-N-(adamantan-1-ylmethyl)-2-N-methyl-2-N-pyridin-4-ylpyrazolo[1,5-a]pyridine-2,4-dicarboxamide | 444.3 | 1.21 | * |
| 40 | N-(adamantan-1-ylmethyl)-2-[(3-oxo-2,8-diazaspiro[4.5]dec-8-yl)carbonyl]pyrazolo[1,5-a]pyridine-4-carboxamide | 490.4 | 1.25 | * |
| 41 | ethyl N-({4-[(adamantan-1-ylmethyl)carbamoyl]pyrazolo[1,5-a]pyridin-2-yl}carbonyl)glycinate | 439.3 | 1.3 | * |
| 42 | 4-N-(adamantan-1-ylmethyl)-2-N-(2-methoxyethyl)pyrazolo[1,5-a]pyridine-2,4-dicarboxamide | 411.3 | 1.28 | * |

TABLE I-continued

Representative Heteroaryl Amide Analogues

| Compound | | Name | MS | R$_T$ | IC$_{50}$ |
|---|---|---|---|---|---|
| 43 | Chiral | 2-{[(3R)-3-aminopiperidin-1-yl]carbonyl}-N-(4-methyl-2-phenylpentyl)pyrazolo[1,5-a]pyridine-4-carboxamide | 448.4 | 1.2 | * |
| 44 | | tert-butyl [1-({4-[(4-methyl-2-phenylpentyl)carbamoyl]pyrazolo[1,5-a]pyridin-2-yl}carbonyl)pyrrolidin-3-yl]carbamate | 478.3 | 1.33 | |
| 45 | Chiral | 2-{[(3R)-3-aminopyrrolidin-1-yl]carbonyl}-N-(4-methyl-2-phenylpentyl)pyrazolo[1,5-a]pyridine-4-carboxamide | 434.4 | 1.21 | * |

US 8,580,812 B2

TABLE I-continued

Representative Heteroaryl Amide Analogues

| Compound | | | Name | MS | R$_T$ | IC$_{50}$ |
|---|---|---|---|---|---|---|
| 46 | 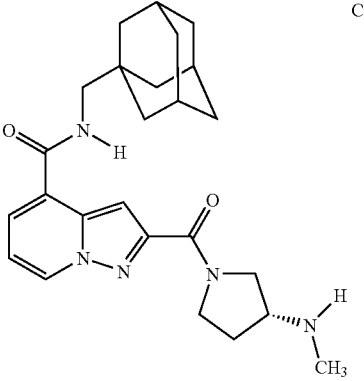 | Chiral | N-(adamantan-1-ylmethyl)-2-{[(3R)-3-(methylamino)pyrrolidin-1-yl]carbonyl}pyrazolo[1,5-a]pyridine-4-carboxamide | 436.4 | 1.2 | * |
| 47 | 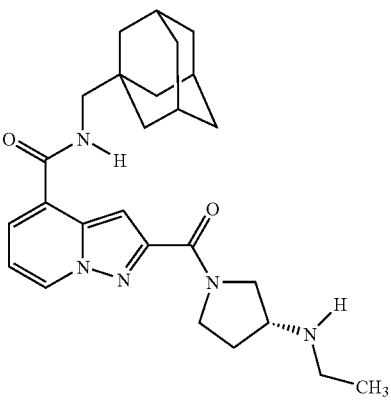 | Chiral | N-(adamantan-1-ylmethyl)-2-{[(3R)-3-(ethylamino)pyrrolidin-1-yl]carbonyl}pyrazolo[1,5-a]pyridine-4-carboxamide | 450.4 | 1.22 | * |
| 48 | 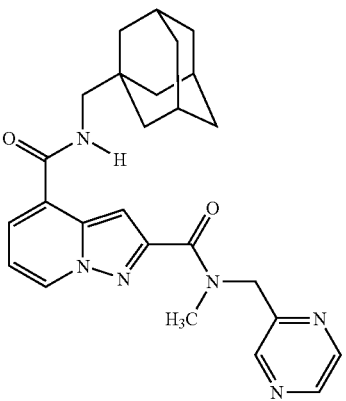 [SMILES: CN(Cc1cnccn1)C(=O)c1cc2c(C(=O)NCC34CC5CC(CC(C5)C3)C4)cccn2n1] | | 4-N-(adamantan-1-ylmethyl)-2-N-methyl-2-N-(pyrazin-2-ylmethyl)pyrazolo[1,5-a]pyridine-2,4-dicarboxamide | 459.3 | 1.28 | * |

TABLE I-continued

Representative Heteroaryl Amide Analogues

| Compound | Name | MS | R$_T$ | IC$_{50}$ |
|---|---|---|---|---|
| 49 | 4-N-(adamantan-1-ylmethyl)-2-N-methyl-2-N-[(1-methyl-1H-pyrazol-4-yl)methyl]pyrazolo[1,5-a]pyridine-2,4-dicarboxamide | 461.3 | 1.28 | * |
| 50 | 4-N-(adamantan-1-ylmethyl)-2-N-methyl-2-N-(pyridin-2-ylmethyl)pyrazolo[1,5-a]pyridine-2,4-dicarboxamide | 458.3 | .26 | * |
| 51 | 4-N-(adamantan-1-ylmethyl)-2-N-(pyridin-2-ylmethyl)pyrazolo[1,5-a]pyridine-2,4-dicarboxamide | 444.3 | 1.24 | * |

TABLE I-continued

Representative Heteroaryl Amide Analogues

| Compound | Name | MS | $R_T$ | $IC_{50}$ |
|---|---|---|---|---|
| 52 | N-(adamantan-1-ylmethyl)-2-(5,6-dihydroimidazo[1,5-a]pyrazin-7(8H)-ylmethyl)pyrazolo[1,5-a]pyridine-4-carboxamide | 445.4 | 1.21 | * |
| 53 | N-(adamantan-1-ylmethyl)-2-{[methyl(pyridin-2-ylmethyl)amino]methyl}pyrazolo[1,5-a]pyridine-4-carboxamide | 444.4 | 1.23 | * |
| 54 | N-(adamantan-1-ylmethyl)-2-{[methyl(pyridin-3-ylmethyl)amino]methyl}pyrazolo[1,5-a]pyridine-4-carboxamide | 444.4 | 1.21 | * |
| 55 | N-(adamantan-1-ylmethyl)-2-{[methyl(pyrazin-2-ylmethyl)amino]methyl}pyrazolo[1,5-a]pyridine-4-carboxamide | 445.4 | 1.21 | * |

TABLE I-continued

Representative Heteroaryl Amide Analogues

| Compound | | Name | MS | R$_T$ | IC$_{50}$ |
|---|---|---|---|---|---|
| 56 | 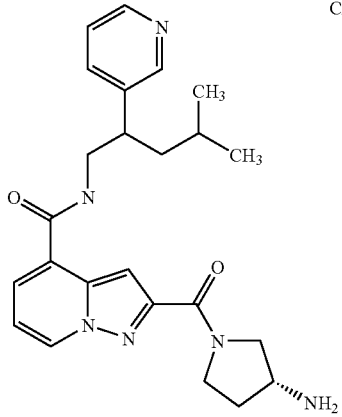 Chiral | 2-{[(3R)-3-aminopyrrolidin-1-yl]carbonyl}-N-(4-methyl-2-pyridin-3-ylpentyl)pyrazolo[1,5-a]pyridine-4-carboxamide | 435.4 | 1 | * |
| 57 | 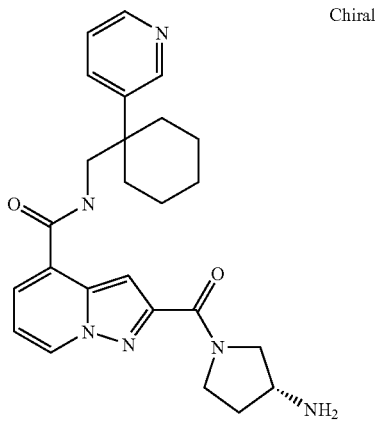 [SMILES: N[C@@H]1CCN(C(=O)c2cc3c(C(=O)NCC4(c5cccnc5)CCCCC4)cccn3n2)C1] Chiral | 2-{[(3R)-3-aminopyrrolidin-1-yl]carbonyl}-N-[(1-pyridin-3-ylcyclohexyl)methyl]pyrazolo[1,5-a]pyridine-4-carboxamide | 447.4 | 0.96 | * |
| 58 | 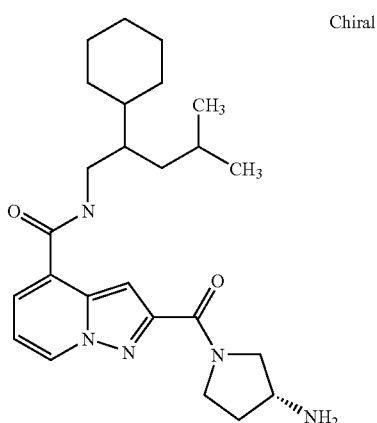 Chiral | 2-{[(3R)-3-aminopyrrolidin-1-yl]carbonyl}-N-(2-cyclohexyl-4-methylpentyl)pyrazolo[1,5-a]pyridine-4-carboxamide | 440.4 | 1.28 | |

TABLE I-continued

Representative Heteroaryl Amide Analogues

| Compound | Name | MS | R$_T$ | IC$_{50}$ |
|---|---|---|---|---|
| 59 | N-(adamantan-1-ylmethyl)-2-{2-[(2-fluoroethyl)amino]-2-oxoethyl}pyrazolo[1,5-a]pyridine-4-carboxamide | 413.3 | 1.26 | * |
| 60 | N-(adamantan-1-ylmethyl)-2-{2-[(2,2-difluoroethyl)amino]-2-oxoethyl}pyrazolo[1,5-a]pyridine-4-carboxamide | 431.3 | 1.28 | * |
| 61 | N-(adamantan-1-ylmethyl)-2-{2-oxo-2-[(2,2,2-trifluoroethyl)amino]ethyl}pyrazolo[1,5-a]pyridine-4-carboxamide | 449.3 | 1.29 | * |
| 62 | 4-N-(adamantan-1-ylmethyl)-2-N-(2-fluoroethyl)pyrazolo[1,5-a]pyridine-2,4-dicarboxamide | 399.3 | 1.28 | * |

TABLE I-continued

Representative Heteroaryl Amide Analogues

| Compound | Name | MS | $R_T$ | $IC_{50}$ |
|---|---|---|---|---|
| 63 | 4-N-(adamantan-1-ylmethyl)-2-N-(2,2-difluoroethyl)pyrazolo[1,5-a]pyridine-2,4-dicarboxamide | 417.3 | 1.29 | * |
| 64 | 4-N-(adamantan-1-ylmethyl)-2-N-(2,2,2-trifluoroethyl)pyrazolo[1,5-a]pyridine-2,4-dicarboxamide | 435.3 | 1.31 | * |
| 65 | 4-N-(adamantan-1-ylmethyl)-2-N-(2-fluorobenzyl)-2-N-methylpyrazolo[1,5-a]pyridine-2,4-dicarboxamide | 475.3 | 1.36 | * |

TABLE I-continued

Representative Heteroaryl Amide Analogues

| Compound | Name | MS | R$_T$ | IC$_{50}$ |
|---|---|---|---|---|
| 66 | 4-N-(adamantan-1-ylmethyl)-2-N-(3-fluorobenzyl)-2-N-methylpyrazolo[1,5-a]pyridine-2,4-dicarboxamide | 475.3 | 1.35 | * |
| 67 | 4-N-(adamantan-1-ylmethyl)-2-N-(4-fluorobenzyl)-2-N-methylpyrazolo[1,5-a]pyridine-2,4-dicarboxamide | 475.3 | 1.35 | * |
| 68 | N-(adamantan-1-ylmethyl)-2-{[(2-fluorobenzyl)(methyl)amino]methyl}pyrazolo[1,5-a]pyridine-4-carboxamide | 461.4 | 1.24 | * |

TABLE I-continued

Representative Heteroaryl Amide Analogues

| Compound | | Name | MS | $R_T$ | $IC_{50}$ |
|---|---|---|---|---|---|
| 69 | 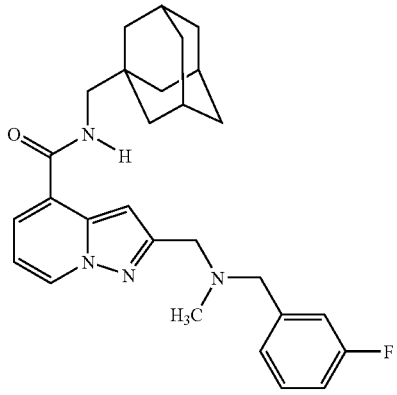 [SMILES: CN(Cc1cccc(F)c1)Cc1cc2c(C(=O)NCC34CC5CC(CC(C5)C3)C4)cccn2n1] | N-(adamantan-1-ylmethyl)-2-{[(3-fluorobenzyl)(methyl)amino]methyl}pyrazolo[1,5-a]pyridine-4-carboxamide | 461.4 | 1.24 | * |
| 70 | 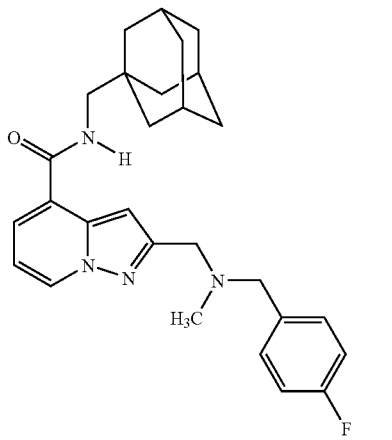 [SMILES: CN(Cc1ccc(F)cc1)Cc1cc2c(C(=O)NCC34CC5CC(CC(C5)C3)C4)cccn2n1] | N-(adamantan-1-ylmethyl)-2-{[(4-fluorobenzyl)(methyl)amino]methyl}pyrazolo[1,5-a]pyridine-4-carboxamide | 461.4 | 1.25 | * |
| 71 | 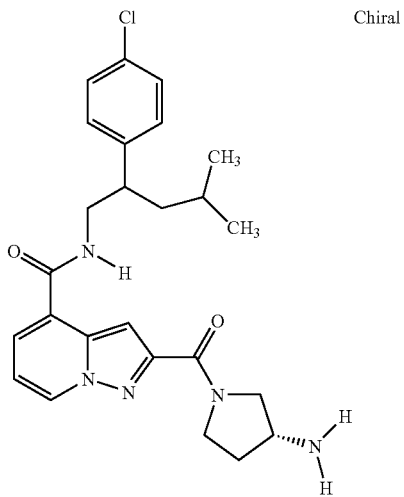 [SMILES: CC(C)CC(CNC(=O)c1cccn2nc(C(=O)N3CC[C@@H](N)C3)cc12)c1ccc(Cl)cc1] Chiral | 2-{[(3R)-3-aminopyrrolidin-1-yl]carbonyl}-N-[2-(4-chlorophenyl)-4-methylpentyl]pyrazolo[1,5-a]pyridine-4-carboxamide | 468.3 | 1.23 | * |

TABLE I-continued

Representative Heteroaryl Amide Analogues

| Compound | | Name | MS | $R_T$ | $IC_{50}$ |
|---|---|---|---|---|---|
| 72 | Chiral | 2-{[(3R)-3-aminopyrrolidin-1-yl]carbonyl}-N-(3-cyclohexyl-2-phenylpropyl)pyrazolo[1,5-a]pyridine-4-carboxamide | 474.4 | 1.27 | * |
| 73 | Chiral | 2-{[(3R)-3-aminopyrrolidin-1-yl]carbonyl}-N-[4-methyl-2-(4-methylphenyl)pentyl]pyrazolo[1,5-a]pyridine-4-carboxamide | 461.5 | 1.41 | * |
| 74 | | 4-N-(adamantan-1-ylmethyl)-2-N-(2-fluoroethyl)-2-N-methylpyrazolo[1,5-a]pyridine-2,4-dicarboxamide | 413.3 | 1.3 | * |

TABLE I-continued

Representative Heteroaryl Amide Analogues

| Compound | Name | MS | R$_T$ | IC$_{50}$ |
|---|---|---|---|---|
| 75 | 4-N-(adamantan-1-ylmethyl)-2-N-(2,2-difluoroethyl)-2-N-methylpyrazolo[1,5-a]pyridine-2,4-dicarboxamide | 431.3 | 1.31 | * |
| 76 | 4-N-(adamantan-1-ylmethyl)-2-N-methyl-2-N-(2,2,2-trifluoroethyl)pyrazolo[1,5-a]pyridine-2,4-dicarboxamide | 449.3 | 1.33 | * |
| 77 | N-(adamantan-1-ylmethyl)-2-{2-[(2-fluoroethyl)(methyl)amino]-2-oxoethyl}pyrazolo[1,5-a]pyridine-4-carboxamide | 427.3 | 1.29 | * |
| 78 | N-(adamantan-1-ylmethyl)-2-{2-[(2,2-difluoroethyl)(methyl)amino]-2-oxoethyl}pyrazolo[1,5-a]pyridine-4-carboxamide | 445.3 | 1.3 | * |

TABLE I-continued

Representative Heteroaryl Amide Analogues

| Compound | | Name | MS | R$_T$ | IC$_{50}$ |
|---|---|---|---|---|---|
| 79 | 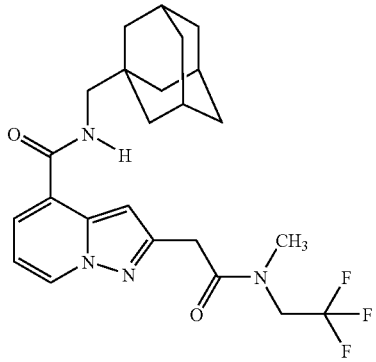 [SMILES: CN(CC(F)(F)F)C(=O)Cc1cc2c(C(=O)NCC34CC5CC(CC(C5)C3)C4)cccn2n1] | N-(adamantan-1-ylmethyl)-2-{2-[methyl(2,2,2-trifluoroethyl)amino]-2-oxoethyl}pyrazolo[1,5-a]pyridine-4-carboxamide | 463.3 | 1.32 | * |
| 80 | 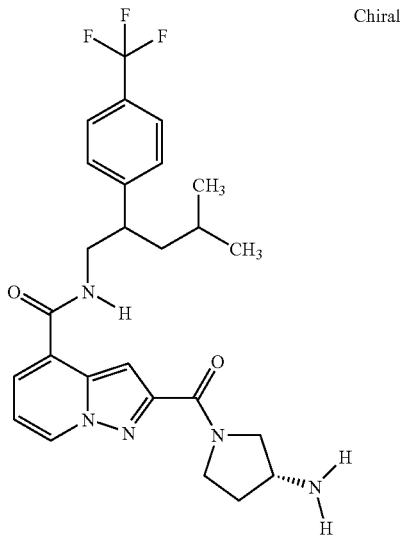 [SMILES: CC(C)CC(CNC(=O)c1cccn2nc(C(=O)N3CC[C@@H](N)C3)cc12)c1ccc(C(F)(F)F)cc1] Chiral | 2-{[(3R)-3-aminopyrrolidin-1-yl]carbonyl}-N-{4-methyl-2-[4-(trifluoromethyl)phenyl]pentyl}pyrazolo[1,5-a]pyridine-4-carboxamide | 502.3 | 1.25 | * |
| 81 | 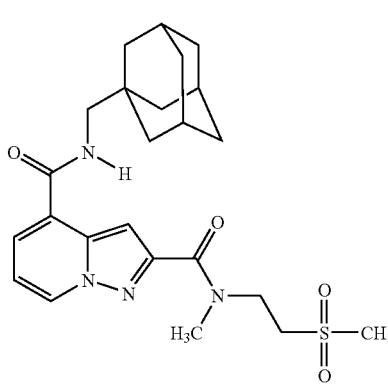 | 4-N-(adamantan-1-ylmethyl)-2-N-methyl-2-N-[2-(methylsulfonyl)ethyl]pyrazolo[1,5-a]pyridine-2,4-dicarboxamide | 473.3 | 1.26 | |

TABLE I-continued

Representative Heteroaryl Amide Analogues

| Compound | Name | MS | R$_T$ | IC$_{50}$ |
|---|---|---|---|---|
| 82 | 4-N-(adamantan-1-ylmethyl)-2-N-(1,1-dioxidotetrahydrothiophen-3-yl)pyrazolo[1,5-a]pyridine-2,4-dicarboxamide | 471.3 | 1.28 | * |
| 83 | N-{[1-(4-chlorophenyl)cyclohexyl]methyl}-2-(5,6-dihydroimidazo[1,5-a]pyrazin-7(8H)-ylcarbonyl)pyrazolo[1,5-a]pyridine-4-carboxamide | 517.3 | 1.25 | * |
| 84 | N-{[1-(4-chlorophenyl)cyclohexyl]methyl}-2-(morpholin-4-ylcarbonyl)pyrazolo[1,5-a]pyridine-4-carboxamide | 481.3 | 1.33 | * |

TABLE I-continued

Representative Heteroaryl Amide Analogues

| Compound | Name | MS | $R_T$ | $IC_{50}$ |
|---|---|---|---|---|
| 85 | 4-N-{[1-(4-chlorophenyl)cyclohex-yl]methyl}-2-N-(2-fluoroethyl)-2-N-methylpyrazolo[1,5-a]pyridine-2,4-dicarboxamide | 471.3 | 1.33 | * |
| 86 | 2-N-(2-fluoroethyl)-2-N-methyl-4-N-{4-methyl-2-[4-(trifluoromethyl)phenyl]pentyl}pyrazolo[1,5-a]pyridine-2,4-dicarboxamide | 493.3 | 1.34 | * |
| 87 | N-{4-methyl-2-[4-(trifluoromethyl)phenyl]pentyl}-2-(morpholin-4-ylcarbonyl)pyrazolo[1,5-a]pyridine-4-carboxamide | 503.3 | 1.33 | * |

TABLE I-continued

Representative Heteroaryl Amide Analogues

| Compound | | Name | MS | $R_T$ | $IC_{50}$ |
|---|---|---|---|---|---|
| 88 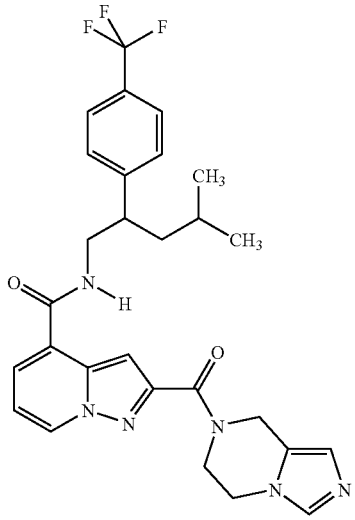 [SMILES: CC(C)CC(CNC(=O)c1cccn2nc(C(=O)N3CCn4cncc4C3)cc12)c1ccc(C(F)(F)F)cc1] | | 2-(5,6-dihydroimidazo[1,5-a]pyrazin-7(8H)-ylcarbonyl)-N-{4-methyl-2-[4-(trifluoromethyl)phenyl]pentyl}pyrazolo[1,5-a]pyridine-4-carboxamide | 539.3 | 1.25 | * |
| 89 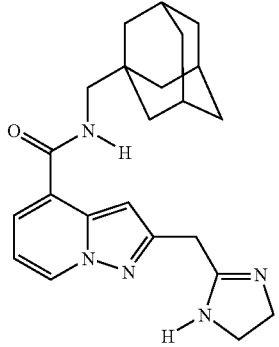 [SMILES: O=C(NCC12CC3CC(CC(C3)C1)C2)c1cccn2nc(CC3=NCCN3)cc12] | | N-(adamantan-1-ylmethyl)-2-(4,5-dihydro-1H-imidazol-2-ylmethyl)pyrazolo[1,5-a]pyridine-4-carboxamide | 405.5 | 1.31 | * |
| 90 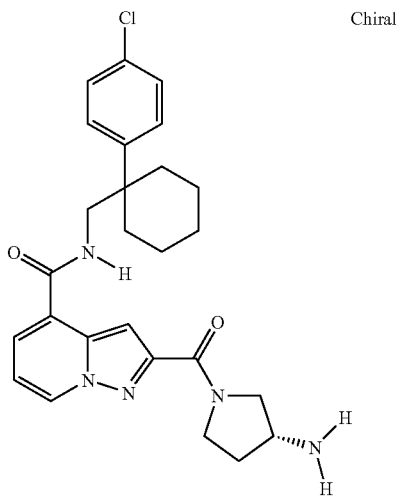 [SMILES: N[C@@H]1CCN(C(=O)c2cc3c(C(=O)NCC4(c5ccc(Cl)cc5)CCCCC4)cccn3n2)C1] | Chiral | 2-{[(3R)-3-aminopyrrolidin-1-yl]carbonyl}-N-{[1-(4-chlorophenyl)cyclohexyl]methyl}pyrazolo[1,5-a]pyridine-4-carboxamide | 480.3 | 1.25 | * |

TABLE I-continued

Representative Heteroaryl Amide Analogues

| Compound | | Name | MS | $R_T$ | $IC_{50}$ |
|---|---|---|---|---|---|
| 91 | 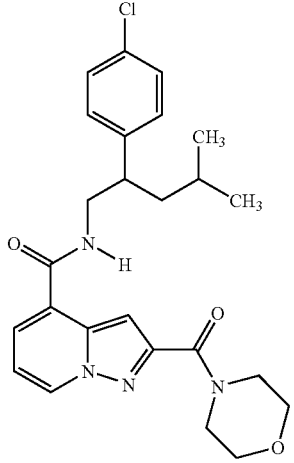 [SMILES: CC(C)CC(CNC(=O)c1cccn2nc(C(=O)N3CCOCC3)cc12)c1ccc(Cl)cc1] | N-[2-(4-chlorophenyl)-4-methylpentyl]-2-(morpholin-4-ylcarbonyl)pyrazolo[1,5-a]pyridine-4-carboxamide | 468.98 | 1.32 | * |
| 92 | 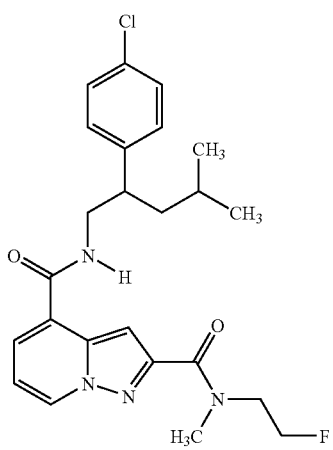 [SMILES: CC(C)CC(CNC(=O)c1cccn2nc(C(=O)N(C)CCF)cc12)c1ccc(Cl)cc1] | Pyrazolo[1,5-a]pyridine-2,4-dicarboxylic acid 4-{[2-(4-chloro-phenyl)-4-methyl-pentyl]-amide} 2-[(2-fluoro-ethyl)-methyl-amide] | 458.96 | 1.33 | * |
| 93 | 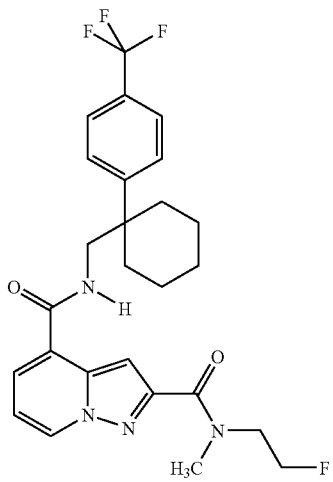 [SMILES: CN(CCF)C(=O)c1cc2c(C(=O)NCC3(c4ccc(C(F)(F)F)cc4)CCCCC3)cccn2n1] | Pyrazolo[1,5-a]pyridine-2,4-dicarboxylic acid 2-[(2-fluoro-ethyl)-methyl-amide]-4-{[1-(4-trifluoromethyl-phenyl)-cyclohexylmethyl]-amide} | 504.52 | | |

TABLE I-continued
Representative Heteroaryl Amide Analogues
| Compound | | Name | MS | R$_T$ | IC$_{50}$ |
|---|---|---|---|---|---|
| 94 | 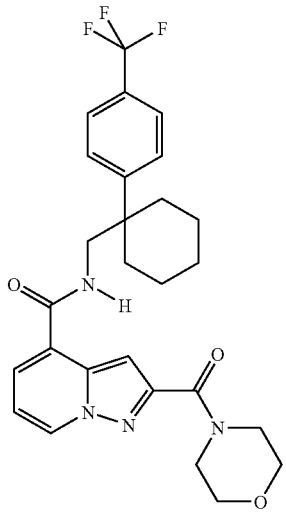 [SMILES: O=C(NCC1(c2ccc(C(F)(F)F)cc2)CCCCC1)c1cccn2nc(C(=O)N3CCOCC3)cc12] | 2-(morpholin-4-ylcarbonyl)-N-({1-[4-(trifluoromethyl)phenyl]cyclohexyl}methyl)pyrazolo[1,5-a]pyridine-4-carboxamide | 514.54 | 1.33 | * |
| 95 | 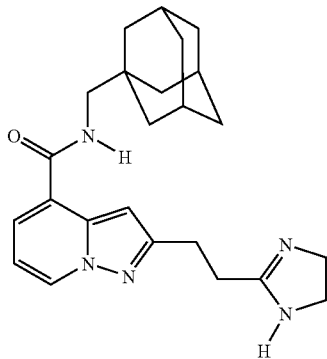 [SMILES: O=C(NCC12CC3CC(CC(C3)C1)C2)c1cccn2nc(CCC3=NCCN3)cc12] | N-(adamantan-1-ylmethyl)-2-[2-(4,5-dihydro-1H-imidazol-2-yl)ethyl]pyrazolo[1,5-a]pyridine-4-carboxamide | 405.54 | 1.21 | * |
| 96 | 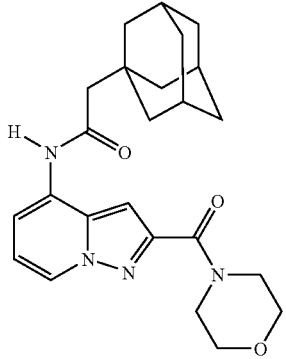 [SMILES: O=C(CC12CC3CC(CC(C3)C1)C2)Nc1cccn2nc(C(=O)N3CCOCC3)cc12] | 2-adamantan-1-yl-N-[2-(morpholin-4-ylcarbonyl)pyrazolo[1,5-a]pyridin-4-yl]acetamide | 422.52 | 1.33 | * |

TABLE I-continued

Representative Heteroaryl Amide Analogues

| Compound | Name | MS | R$_T$ | IC$_{50}$ |
|---|---|---|---|---|
| 97 | 2-adamantan-1-yl-N-[2-(5,6-dihydroimidazo[1,5-a]pyrazin-7(8H)-ylcarbonyl)pyrazolo[1,5-a]pyridin-4-yl]acetamide | 458.56 | 1.23 | * |
| 98 | 4-[(adamantan-1-ylacetyl)amino]-N-(2-fluoroethyl)-N-methylpyrazolo[1,5-a]pyridine-2-carboxamide | 412.50 | 1.33 | * |
| 99 (Chiral) | 2-adamantan-1-yl-N-(2-{[(3R)-3-aminopyrrolidin-1-yl]carbonyl}pyrazolo[1,5-a]pyridin-4-yl)acetamide | 421.54 | 1.22 | * |

TABLE I-continued

Representative Heteroaryl Amide Analogues

| Compound | | Name | MS | $R_T$ | $IC_{50}$ |
|---|---|---|---|---|---|
| 100 | 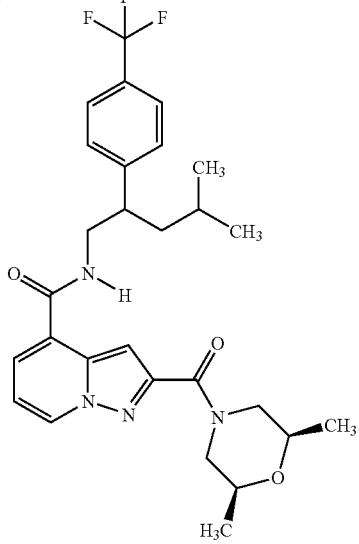 | rel-2-{[(2R,6S)-2,6-dimethylmorpholin-4-yl]carbonyl}-N-{4-methyl-2-[4-(trifluoromethyl)phenyl]pentyl}pyrazolo[1,5-a]pyridine-4-carboxamide | 530.58 | 1.36 | * |
| 101 | 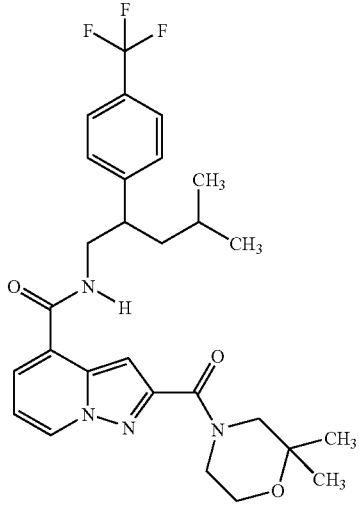 [SMILES: CC(C)CC(CNC(=O)c1cccn2nc(C(=O)N3CCOC(C)(C)C3)cc12)c1ccc(C(F)(F)F)cc1] | 2-[(2,2-dimethylmorpholin-4-yl)carbonyl]-N-{4-methyl-2-[4-(trifluoromethyl)phenyl]pentyl}pyrazolo[1,5-a]pyridine-4-carboxamide | 530.58 | 1.36 | * |
| 102 | 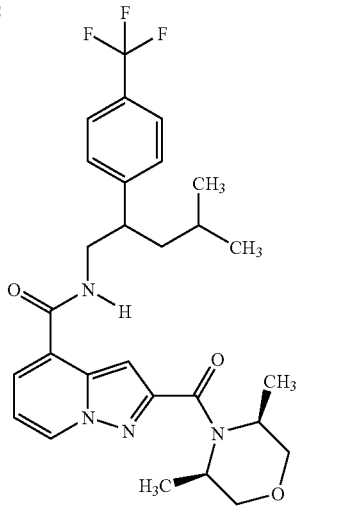 [SMILES: CC(C)CC(CNC(=O)c1cccn2nc(C(=O)N3[C@H](C)COC[C@@H]3C)cc12)c1ccc(C(F)(F)F)cc1] | rel-2-{[(3R,5S)-3,5-dimethylmorpholin-4-yl]carbonyl}-N-{4-methyl-2-[4-(trifluoromethyl)phenyl]pentyl}pyrazolo[1,5-a]pyridine-4-carboxamide | 530.58 | 1.36 | * |

TABLE I-continued

Representative Heteroaryl Amide Analogues

| Compound | | Name | MS | $R_T$ | $IC_{50}$ |
|---|---|---|---|---|---|
| 103 | 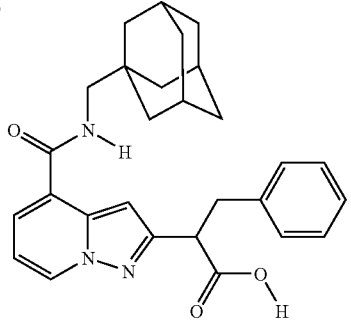 [SMILES: O=C(NCC12CC3CC(CC(C3)C1)C2)c1cccn2nc(C(Cc3ccccc3)C(=O)O)cc12] | 2-{4-[(adamantan-1-ylmethyl)carbamoyl]pyrazolo[1,5-a]pyridin-2-yl}-3-phenylpropanoic acid | 457.56 | 1.30 | * |
| 104 | 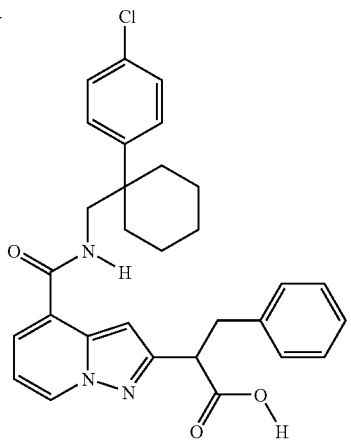 | 2-[4-({[1-(4-chlorophenyl)cyclohex-yl]methyl}carbamoyl)pyrazolo[1,5-a]pyridin-2-yl]-3-phenyl propanoic acid | 516.03 | 1.38 | * |
| 105 | 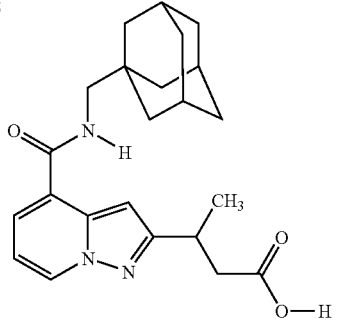 [SMILES: CC(CC(=O)O)c1cc2c(C(=O)NCC34CC5CC(CC(C5)C3)C4)cccn2n1] | 3-{4-[(adamantan-1-ylmethyl)carbamoyl]pyrazolo[1,5-a]pyridin-2-yl}butanoic acid | 395.49 | 1.32 | * |
| 106 | 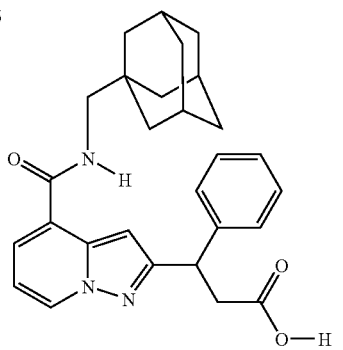 | 3-{4-[(adamantan-1-ylmethyl)carbamoyl]pyrazolo[1,5-a]pyridin-2-yl}-3-phenylpropanoic acid | 457.56 | 1.36 | * |

TABLE I-continued

Representative Heteroaryl Amide Analogues

| Compound | Name | MS | R_T | IC_{50} |
|---|---|---|---|---|
| 107 | 3-{4-[(adamantan-1-ylmethyl)carbamoyl]pyrazolo[1,5-a]pyridin-2-yl}-4-phenylbutanoic acid | 471.59 | 1.38 | * |
| 108 | 4-{8-[(adamantan-1-ylmethyl)carbamoyl]indolizin-2-yl}benzoic acid | 428.11 | 1.58 | * |
| 109 | N-(adamantan-1-ylmethyl)-3-(4-cyanobenzoyl)indolizine-8-carboxamide | 438.23 | 1.39 | * |

TABLE I-continued

Representative Heteroaryl Amide Analogues

| Compound | | Name | MS | $R_T$ | $IC_{50}$ |
|---|---|---|---|---|---|
| 110 | | N-(adamantan-1-ylmethyl)-3-(4-carbamoylbenzoyl)indolizine-8-carboxamide | 456.21 | 1.33 | * |
| 111 | | 2-(4-cyanophenyl)-N-[(1-pyridin-3-ylcyclohexyl)methyl]indolizine-8-carboxamide | 435.20 | 1.17 | |
| 112 | | N-(adamantan-1-ylmethyl)-2-(4-carbamoylphenyl)indolizine-8-carboxamide | 428.22 | 1.31 | * |

TABLE II

Additional Representative Heteroaryl Amide Analogues

| Compound | | Name |
|---|---|---|
| 120 | | (R)-2-(3-aminopyrrolidine-1-carbonyl)-N-((1-(4-(trifluoromethyl)phenyl)cyclohexyl)methyl)H-pyrazolo[1,5-a]pyridine-4-carboxamide |

TABLE II-continued

Additional Representative Heteroaryl Amide Analogues

| Compound | | Name |
|---|---|---|
| 121 | 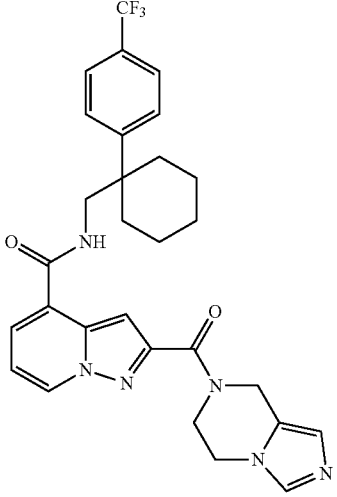 [SMILES: O=C(NCC1(c2ccc(C(F)(F)F)cc2)CCCCC1)c1cccn2nc(C(=O)N3CCn4cncc4C3)cc12] | 2-(5,6,7,8-tetrahydroimidazo[1,5-a]pyrazine-7-carbonyl)-N-((1-(4-(trifluoromethyl)phenyl)cyclohexyl)methyl)H-pyrazolo[1,5-a]pyridine-4-carboxamide |
| 122 | 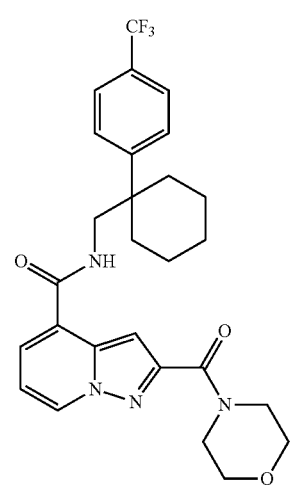 [SMILES: O=C(NCC1(c2ccc(C(F)(F)F)cc2)CCCCC1)c1cccn2nc(C(=O)N3CCOCC3)cc12] | 2-(morpholine-4-carbonyl)-N-((1-(4-(trifluoromethyl)phenyl)cyclohexyl)methyl)H-pyrazolo[1,5-a]pyridine-4-carboxamide |
| 123 | 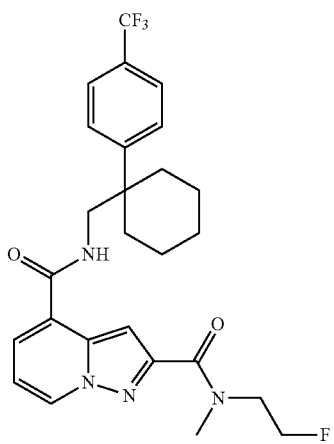 [SMILES: CN(CCF)C(=O)c1cc2c(C(=O)NCC3(c4ccc(C(F)(F)F)cc4)CCCCC3)cccn2n1] | Pyrazolo[1,5-a]pyridine-2,4-dicarboxylic acid 2-[(2-fluoro-ethyl)-methyl-amide] 4-{[1-(4-trifluoromethyl-phenyl)-cyclohexylmethyl]-amide} |

TABLE II-continued

Additional Representative Heteroaryl Amide Analogues

| Compound | | Name |
|---|---|---|
| 124 | 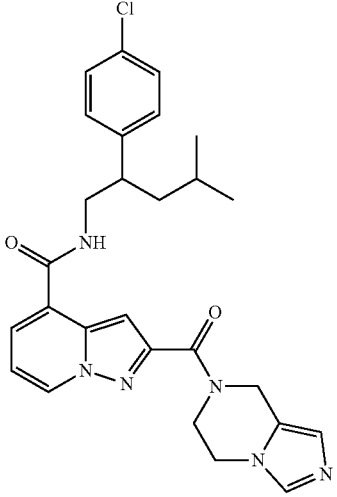 [SMILES: CC(C)CC(CNC(=O)c1cccn2nc(C(=O)N3CCn4cncc4C3)cc12)c1ccc(Cl)cc1] | N-(2-(4-chlorophenyl)-4-methylpentyl)-2-(5,6,7,8-tetrahydroimidazo[1,5-a]pyrazine-7-carbonyl)H-pyrazolo[1,5-a]pyridine-4-carboxamide |
| 125 | 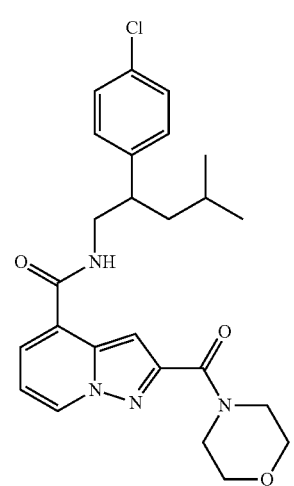 [SMILES: CC(C)CC(CNC(=O)c1cccn2nc(C(=O)N3CCOCC3)cc12)c1ccc(Cl)cc1] | N-(2-(4-chlorophenyl)-4-methylpentyl)-2-(morpholine-4-carbonyl)H-pyrazolo[1,5-a]pyridine-4-carboxamide |
| 126 | 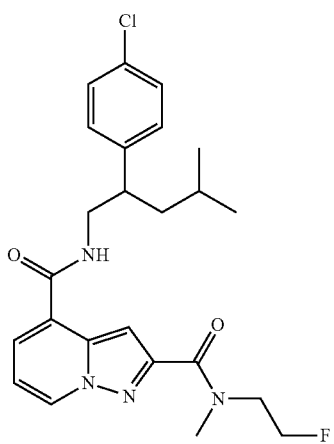 [SMILES: CC(C)CC(CNC(=O)c1cccn2nc(C(=O)N(C)CCF)cc12)c1ccc(Cl)cc1] | Pyrazolo[1,5-a]pyridine-2,4-dicarboxylic acid 2-[(2-fluoro-ethyl)-methyl-amide] 4-{[4-methyl-2-(4-trifluoromethyl-phenyl)-pentyl]-amide} |

TABLE II-continued

Additional Representative Heteroaryl Amide Analogues

| Compound | | Name |
|---|---|---|
| 127 | | N-(adamantan-1-ylmethyl)-2-{[5-(2-hydroxyethyl)-2H-tetrazol-2-yl]methyl}pyrazolo[1,5-a]pyridine-4-carboxamide |
| 128 | | N-(adamantan-1-ylmethyl)-2-{[5-(2-hydroxyethyl)-1H-tetrazol-1-yl]methyl}pyrazolo[1,5-a]pyridine-4-carboxamide |
| 129 | | N-[2-(3-Amino-pyrrolidine-1-carbonyl)-pyrazolo[1,5-a]pyridin-4-yl]-2-(3-ethyl-bicyclo[3.3.1]non-1-yl)acetamide |
| 130 | | 4-[2-(3-Ethyl-bicyclo[3.3.1]non-1-yl)-acetylamino]-pyrazolo[1,5-a]pyridine-2-carboxylic acid (2-fluoro-ethyl)-methyl-amide |

TABLE II-continued

Additional Representative Heteroaryl Amide Analogues

| | Compound | Name |
|---|---|---|
| 131 | | 2-(3-Ethyl-bicyclo[3.3.1]non-1-yl)-N-[2-(morpholine-4-carbonyl)-pyrazolo[1,5-a]pyridin-4-yl]-acetamide |
| 132 | | N-[2-(5,6-Dihydro-8H-imidazo[1,5-a]pyrazine-7-carbonyl)-pyrazolo[1,5-a]pyridin-4-yl]-2-(3-ethyl-bicyclo[3.3.1]non-1-yl)-acetamide |

Example 4

P2X$_7$ Assays

This Example illustrates representative assays for use in evaluating test compounds for agonist and antagonist activity.

A. High Throughput P2X$_7$ Calcium Mobilization Assay

SH-SY5Y cells, ATCC Number CRL-2266, (American Type Culture Collection, Manassas, Va.) are cultured under DMEM/High medium supplemented with 10% FBS, and 10 mM HEPES (Invitrogen Corp., Carlsbad, Calif.) in 5% $CO_2$ and at 37° C. One day prior to the experiment, cells are plated at a density of 100,000 cells/well in a 96 well black/clear TC plate (Corning® Costar®, Sigma-Aldrich Co., St. Louis, Mo.). At the beginning of the experiment, the culture medium is removed and cells are incubated with 50 µL of 2.3 µM Fluo-4 AM dye (Invitrogen Corp.) in the assay solution (5 mM KCl, 9.6 mM $NaH_2PO_4 \cdot H_2O$, 25 mM HEPES, 280 mM Sucrose, 5 mM Glucose, and 0.5 mM $CaCl_2$; pH is adjusted to 7.4 with NaOH) for an hour at 37° C. After one hour dye incubation, wells are rinsed once with 50 µL assay solution, and are then incubated for an hour at room temperature with 100 µL assay solution containing the test compound. The final concentration of test compound generally ranges from 1 to 2500 nM; for positive control cells, no test compound is added. After the one hour incubation, plates are transferred to a FLIPR$^{TETRA}$ instrument (Molecular Devices, Sunnyvale, Calif.) for calcium mobilization analysis.

For determination of antagonist activity, 50 µL of P2X$_7$ agonist (2'(3')-O-(4-benzoyl-benzoyl)adenosine 5'-triphosephate (BzATP; Sigma-Aldrich) in the assay solution is transferred using the FLIPR into the plate, such that the final agonist concentration is 80 µM (about EC$_{50}$). In negative control cells, 50 µL of assay solution without agonist is added at this stage. The peak fluorescence signal over a 2 minute period is then measured.

The data is analyzed as follows. First, the average maximum relative fluorescent unit (RFU) response from the negative control wells (no agonist) is subtracted from the maximum response detected for each of the other experimental wells. Second, average maximum RFU response is calculated for the positive control wells (agonist wells). Then, percent inhibition for each compound tested is calculated using the equation:

Percent Inhibition=100−100×(Peak Signal in Test Cells/Peak Signal in Control Cells)

The % inhibition data is plotted as a function of test compound concentration and test compound IC$_{50}$ is determined using, for example, KALEIDAGRAPH software (Synergy Software, Reading, Pa.) best fit of the data to the equation:

$$y = m_1 * (1/(1+(m_2/m_0)^{m_3}))$$

where y is the percent inhibition, $m_0$ is the concentration of the agonist, $m_1$ is the maximum RFU, $m_2$ corresponds to the test compound IC$_{50}$ (the concentration required to provide a 50% decrease, relative to the response observed in the presence of agonist and without antagonist) and $m_3$ is the Hill coefficient. Alternatively, test compound IC$_{50}$ is determined using a linear regression in which x is ln(concentration of test compound) and y is ln(percent inhibition/(100−percent inhibition). Data with a percent inhibition that is greater than 90% or less than 15% are rejected and are not used in the regression. The IC$_{50}$ calculated in this fashion is $e^{(-intercept/slope)}$. For antagonists of the P2X$_7$, the calculated IC$_{50}$ is preferably below 20 micromolar, more preferably below 10 micromolar, even more preferably below 5 micromolar and most preferably below 1 micromolar.

Similar assays are performed in the absence of added agonist for the determination of agonist activity of the test compounds. Within such assays, the ability of a test compound to act as an agonist of P2X$_7$ is determined by measuring the fluorescence response elicited by the test compound as a function of compound concentration. P2X$_7$ antagonists that exhibit no detectable agonist activity elicit no detectable fluorescence response at a concentration of 2,500 nM.

B. Electrophysiological P2X$_7$ Assays

SH-SY5Y cells are cultured under DMEM/High medium supplemented with 10% FBS, and 10 mM HEPES (Invitrogen Corp., Carlsbad, Calif.) in 5% $CO_2$ and at 37° C., and are split onto 12 mm round Poly-D-Lysine (PDL) coated coverslips (BD Biosciences, San Jose, Calif.) in a 35 mm dish with a density of 130K cells/dish a day prior to the experiment.

Whole cell voltage clamp recordings are made with the Axopatch-200B amplifier (Axon Instruments, Foster City, Calif.). The recording electrodes are pulled from borosilicate pipettes (World Precision Instruments, Sarasota, Fla.) on a horizontal puller (Sutter Instrument Model P-87) and have resistances ranging from 2 to 3 MΩ when backfilled with internal solution. All voltage protocols are generated using pClamp 8 (Axon Instruments) software. Data are digitized at 1 or 5 kHz and recorded onto a PC for further analysis. Data are analyzed using Clampfit (Axon Instruments), Excel (Microsoft, Redmond, Wash.), and Origin software (MicroCal, LLC; Northampton, Mass.). All whole-cell recordings are conducted at room temperature. Internal solution contains (in mM): 100 KF, 40 KCl, 5 NaCl, 10 EGTA and 10 HEPES (pH=7.4 adjusted with KOH). The external solution contains 70 mM NaCl, 0.3 mM $CaCl_2$, 5 mM KCl, 20 mM HEPES, 10 mM glucose, and 134 mM sucrose (pH=7.4 adjusted with NaOH). All chemicals are from Sigma, unless otherwise stated.

$P2X_7$ is activated by 200 μM of $P2X_7$ agonist, BzATP. At a holding potential of −80 mV, the activated inward current is recorded in the presence and absence of the test compound. Then, percent inhibition for each compound tested is calculated using the equation:

% Inhibition=100−100×(Current Amplitude in Compound/Current Amplitude in Control).

To determine a test compound's $IC_{50}$ for $P2X_7$ electrophysiologically, several concentrations of the compound are tested and their inhibitions on $P2X_7$ currents are calculated as above. This dose-response curve is best fitted using Origin software (Microcal, Mass.) with the following equation:

Percent Inhibition=$100/(1+(IC_{50}/C)^N)$ where C is the concentration of the antagonist, N is the Hill coefficient, and $IC_{50}$ represents the compound $IC_{50}$ value against $P2X_7$.

Example 5

Carrageenan-Induced Mechanical Hyperalgesia (Paw Pressure) Assay for Determining Pain Relief This Example illustrates a representative method for assessing the degree of pain relief provided by a test compound.

Adult male Sprague Dawley rats (200-300 g; obtained from Harlan Sprague Dawley, Inc., Indianapolis, Ind.) are housed under a 12 h light/dark cycle with access to food and water ad libitum. For the assay, all animals are habituated once, baselined twice and tested once, with each procedure being conducted on a separate day. Prior to each day's procedure, animals are allowed to acclimate for at least 1 hour in the testing room before the start of the procedure. For habituation, each animal is gently restrained with each hindpaw consecutively extended in front of the animal as is necessary for testing. This procedure is performed by alternating hindpaws and repeated three times for each hindpaw. Animals are then subjected to the first baseline, second baseline and testing on consecutive days. For each baseline, the animal is restrained as in the habituation session and the paw tested using the paw pressure testing apparatus (Digital Randall Selitto, IITC Inc., Woodland Hills, Calif.). Animals are baselined and tested in groups of ten, each animal being tested once on the left and right hindpaws, followed by the next consecutive animal. This procedure is repeated three times for a total of three measurements on each hindpaw. If any individual read is drastically different (varies by more than about 100 g) from the other two on a given hindpaw, the hindpaw is retested a $4^{th}$ time, and the average of the three most consistent scores is used. On test day, all animals are injected with 0.1 mL intraplantar 0.5%-1.5% carrageenan (dissolved in saline) 3 hours prior to testing. Test compounds or vehicle may be administered by various routes at various timepoints prior to testing, but for any particular assay, the routes and timepoints are the same for animals in each treatment group administered test compound (a different dosage of test compound may be administered to each such group) and those in the treatment group administered vehicle control. If a compound is orally administered, the animals are food-deprived the evening before testing. As with the baseline, each hindpaw is tested three times and the results recorded for analysis.

Hypersensitivity of nociception values are calculated for each treatment group as the mean of the left foot gram force scores on test day (left foot only or LFO score). Statistical significance between treatment groups is determined by running an ANOVA on LFO scores followed with a least significant difference (LSD) post hoc test. A $p<0.05$ is considered to be a statistically significant difference.

Compounds are said to relieve pain in this model if they result in a statistically significant reduction in hypersensitivity of nociception values compared to vehicle controls, determined as described above, when administered (0.01-50 mg/kg, orally, parenterally or topically) immediately prior to testing as a single bolus, or for several days: once or twice or three times daily prior to testing.

What is claimed is:

1. A compound of the formula:

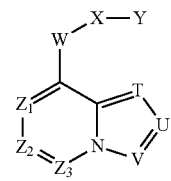

or a pharmaceutically acceptable salt thereof, wherein:

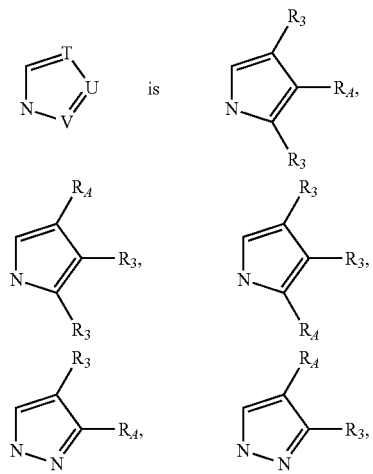

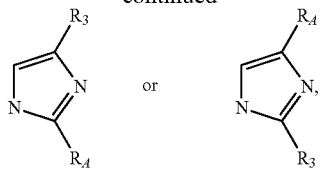

W is —C(=O)NR₄—, —NR₄C(=O)— or —NR₄—NR₄—C(=O)—;

X is absent or $C_1$-$C_6$alkylene that is substituted with from 0 to 4 substituents independently chosen from:
(i) $C_1$-$C_4$alkyl, ($C_3$-$C_8$cycloalkyl)$C_0$-$C_2$alkyl and phenyl$C_0$-$C_2$alkyl;
(ii) substituents that are taken together to form a 3- to 7-membered cycloalkyl or heterocycloalkyl ring; and
(iii) substituents that are taken together with $R_4$ to form a 4- to 7-membered heterocycloalkyl;

Y is $C_3$-$C_{16}$cycloalkyl, 4- to 16-membered heterocycloalkyl, 6- to 16-membered aryl or 5- to 16-membered heteroaryl, each of which is substituted with from 0 to 6 substituents independently chosen from hydroxy, halogen, cyano, amino, nitro, oxo, aminocarbonyl, aminosulfonyl, COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$-aminoalkyl, $C_1$-$C_6$alkoxy, $C_1$-$C_4$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$Z_1$ and $Z_3$ is $CR_2$;
$Z_2$ is $CR_2$ or $CR_4$;

Each $R_2$ and each $R_3$ is independently chosen from hydrogen, halogen, cyano, amino, nitro, aminocarbonyl, aminosulfonyl, COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

Each $R_4$ is independently hydrogen, $C_1$-$C_6$alkyl, ($C_3$-$C_8$cycloalkyl)$C_0$-$C_2$alkyl or taken together with a substituent of X to form a 4- to 7-membered heterocycloalkyl;

$R_A$ is a group of the formula -L-A-M, wherein:
L is absent or $C_1$-$C_6$alkylene that is optionally modified by the replacement of a carbon-carbon single bond with a double or triple carbon-carbon bond, which alkylene is optionally substituted with oxo, —COOH, —SO₃H, —SO₂NH₂, —PO₃H₂, tetrazole or oxadiazaolone;
A is absent or CO, O, $NR_6$, S, SO, $SO_2$, $CONR_6$, $NR_6CO$, ($C_4$-$C_7$cycloalkyl)$C_0$-$C_4$alkylene or (4- to 7-membered heterocycloalkyl)$C_0$-$C_4$alkylene; wherein $R_6$ is hydrogen or $C_1$-$C_6$alkyl; and
M is:
(i) hydroxy, cyano, amino, aminocarbonyl, aminosulfonyl or COOH; or
(ii) $C_1$-$C_6$haloalkyl, $C_1$-$C_6$alkoxy, 5- to 10-membered carbocycle, 4- to 10-membered heterocycle, $C_1$-$C_6$alkanoyloxy, $C_1$-$C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is optionally substituted and each of which is preferably substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

2. A compound or salt thereof according to claim 1, wherein each $R_3$ is independently hydrogen or $C_1$-$C_4$alkyl.

3. A compound or salt thereof according to claim 1, wherein $R_A$ is $C_1$-$C_6$hydroxyalkyl, $C_1$-$C_6$cyanoalkyl, $C_2$-$C_6$alkenyl, $C_2$-$C_6$alkyl ether, phenyl$C_0$-$C_4$alkyl, (4- to 10-membered heterocycle)$C_0$-$C_4$alkyl, ($C_1$-$C_6$alkylsulfonylamino)$C_0$-$C_4$alkyl, ($C_1$-$C_6$alkanoyloxy)$C_0$-$C_4$alkyl, ($C_1$-$C_6$alkylsulfonyloxy)$C_0$-$C_4$alkyl, (mono- or di-$C_1$-$C_6$alkylamino)$C_0$-$C_4$alkyl, and (mono- or di-$C_1$-$C_6$alkylaminocarbonyl)$C_0$-$C_4$alkyl; each of which is substituted with from 0 to 4 substituents independently chosen from:
(i) oxo, halogen, amino, cyano, hydroxy, aminocarbonyl, aminosulfonyl and COOH; and
(ii) $C_1$-$C_6$alkyl, $C_1$-$C_6$hydroxyalkyl, $C_1$-$C_6$alkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-$C_1$-$C_6$alkylaminocarbonyl, mono- or di-$C_1$-$C_6$alkylaminosulfonyl, phenyl and 4- to 7-membered heterocycle; each of which is substituted with from 0 to 4 substituents independently chosen from halogen, hydroxy, amino, oxo, aminocarbonyl, aminosulfonyl, COOH, $C_1$-$C_4$alkyl and $C_1$-$C_4$haloalkyl.

4. A compound or salt thereof according to claim 3, wherein $R_A$ is $C_1$-$C_6$hydroxyalkyl, $C_1$-$C_6$cyanoalkyl, $C_2$-$C_6$cyanoalkenyl, $C_2$-$C_6$alkyl ether, (mono- or di-$C_1$-$C_6$alkylamino)$C_0$-$C_4$alkyl, (mono- or di-$C_1$-$C_6$alkylaminocarbonyl)$C_0$-$C_4$alkyl, or (4- to 7-membered heterocycle)$C_1$-$C_4$alkyl; each of which is substituted with from 0 to 4 substituents independently chosen from amino, hydroxy, oxo, halogen, aminocarbonyl, aminosulfonyl, $C_1$-$C_6$alkyl, $C_1$-$C_6$hydroxyalkyl, $C_1$-$C_6$alkoxy, $C_2$-$C_6$alkyl ether, mono- or di-($C_1$-$C_6$alkyl)amino, mono- or di-$C_1$-$C_6$alkylaminocarbonyl, $C_1$-$C_6$alkylsulfonyl, $C_1$-$C_6$alkylsulfonylamino, 4- to 7-membered heterocycloalkyl, and 5- or 6-membered heteroaryl.

5. A compound or salt thereof according to claim 3, wherein $R_A$ is a group of te formula:

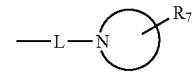

wherein:

L is absent or $C_1$-$C_6$alkylene that is optionally substituted with oxo;

represents a 4- to 7-membered heterocycloalkyl that is optionally fused to phenyl or to a 5- or 6-membered heteroaryl; and $R_7$ represents from 0 to 4 substituents independently chosen from:

(i) hydroxy, amino, oxo, aminocarbonyl, aminosulfonyl and COOH;

(ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, and 4- to 7-membered heterocycle; each of which is substituted with from 0 to 4 substituents independently chosen from halogen, hydroxy, amino, oxo, aminocarbonyl, aminosulfonyl, COOH, $C_1$-$C_6$alkyl, $C_1$-$C_6$alkoxy, mono- or di-($C_1$-$C_6$alkyl)amino, and $C_1$-$C_6$alkylsulfonylamino;

(iii) substituents that are taken together to form a bridge of the Formula —$(CH_2)_q$—P—$(CH_2)_r$—, wherein q and r are independently 0 or 1 and P is $CH_2$, O, NH or S; and (iv) substituents that are taken together to form a spiro 4- to 7-membered heterocycloalkyl ring that is substituted with from 0 to 2 substituents independently chosen from oxo and $C_1$-$C_4$alkyl.

6. A compound or salt thereof according to claim 5, wherein $R_A$ is a group of the formula:

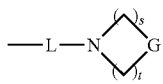

wherein:

L is $C_1$-$C_2$alkylene that is optionally substituted with oxo;

G is $CHR_8$, NH or O;

s and t are independently 0, 1, 2, 3 or 4, such that the sum of s and t ranges from 2 to 5; and $R_8$ is:

(i) hydrogen, amino, aminocarbonyl, aminosulfonyl or COOH; or (ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, or 4- to 7-membered heterocycle; each of which is substituted with from 0 to 4 substituents independently chosen from halogen, hydroxy, amino, oxo, aminocarbonyl, aminosulfonyl, COOH, $C_1$-$C_6$alkyl, $C_1$-$C_6$alkoxy, mono- or di-($C_1$-$C_6$alkyl)amino, and $C_1$-$C_6$alkylsulfonylamino.

7. A compound or salt thereof according to claim 5, wherein $R_A$ is:

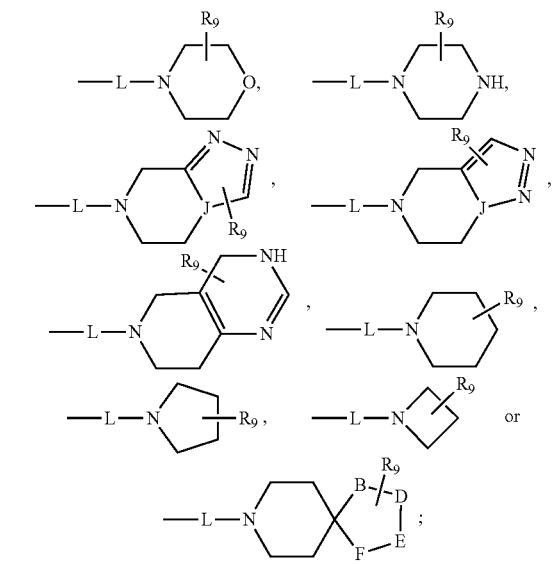

wherein:

J is CH or N;

B, D, E and F are independently chosen from $CH_2$, NH and O; and $R_9$ represents from 0 to 2 substituents independently chosen from:

(i) amino, aminocarbonyl and COOH; and (ii) $C_1$-$C_6$alkyl, mono- or di-($C_1$-$C_6$alkyl)amino$C_0$-$C_2$alkyl, $C_1$-$C_6$alkylsulfonyl and $C_1$-$C_6$alkylsulfonylamino; each of which is substituted with from 0 to 3 substituents independently chosen from halogen, hydroxy, oxo and COOH.

8. A compound or salt thereof according to claim 3, wherein $R_A$ is $C_1$-$C_6$alkyl, $C_2$-$C_6$alkenyl, $C_2$-$C_6$alkyl ether, or mono- or di-($C_1$-$C_6$alkyl)amino$C_0$-$C_4$alkyl, each of which is substituted with from 1 to 4 substituents independently chosen from halogen, hydroxy, cyano, amino, oxo, aminocarbonyl, aminosulfonyl, COOH, $C_1$-$C_6$alkyl, $C_1$-$C_6$alkoxy, mono- or di-($C_1$-$C_6$alkyl)amino, $C_1$-$C_6$alkanoylamino, $C_1$-$C_6$alkylsulfonyl, $C_1$-$C_6$alkylsulfonyloxy, $C_1$-$C_6$alkylsulfonylamino, phenyl that is optionally substituted with halogen or $C_1$-$C_4$alkyl, and 4- to 7-membered heterocycle that is optionally substituted with $C_1$-$C_4$alkyl.

9. A compound or salt thereof according to claim 8, wherein $R_A$ is mono-($C_1$-$C_6$alkyl)amino$C_0$-$C_2$alkyl or $C_2$-$C_6$alkyl ether, each of which is substituted with from 1 to 4 substituents independently chosen from hydroxy, halogen, oxo, COOH, $C_1$-$C_4$alkyl and $C_1$-$C_4$alkoxy.

10. A compound or salt thereof according to claim 1, wherein:

L is not absent;

A is absent; and

M is phenyl or a 5- or 6-membered heteroaryl, each of which is substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

11. A compound or salt thereof according to claim 1, wherein:

L is $C_0$-$C_3$alkylene that is optionally substituted with oxo or COOH;

A is absent; and

M is phenyl that is substituted with amino, cyano, aminocarbonyl, aminosulfonyl, COOH or $C_1$-$C_6$alkyl.

12. A compound or salt thereof according to claim 1, wherein:

L is $C_1$-$C_2$alkylene that is optionally substituted with oxo;

A is absent; and

M is mono- or di-($C_1$-$C_6$alkyl)amino that is substituted with a 5- or 6-membered heteroaryl, each of which heteroaryl is substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

13. A compound or salt thereof according to claim 1, wherein each $R_2$ is hydrogen or $C_1$-$C_6$alkyl.

14. A compound or salt thereof according to claim 1, wherein:

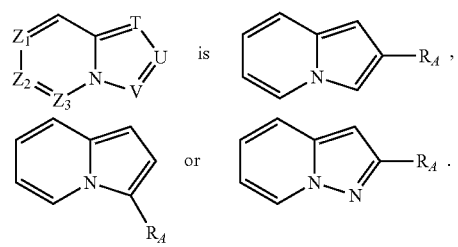

15. A compound or salt thereof according to claim 1, wherein X is methylene or ethylene, each of which is substituted with from 0 to 4 substituents independently chosen from $C_1$-$C_4$alkyl, ($C_3$-$C_8$cycloalkyl)$C_0$-$C_2$alkyl, phenyl and substituents that are taken together to form a 3- to 7-membered cycloalkyl or heterocycloalkyl ring.

16. A compound or salt thereof according to claim 1, wherein Y is cyclopropyl, cyclobutyl, cyclopentyl, cyclohexyl, cycloheptyl, piperidinyl, piperazinyl, morpholinyl, or adamantyl, each of which is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino.

17. A compound or salt thereof according to claim 1, wherein —W—X—Y is:

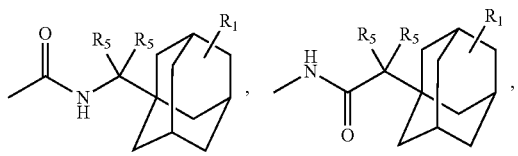

-continued

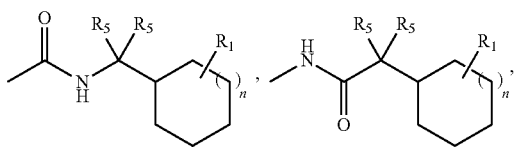

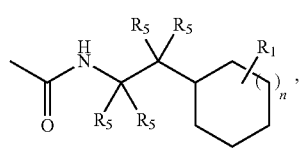

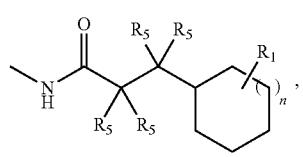

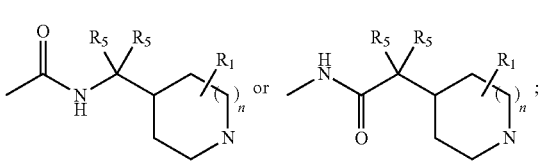

wherein:

n is 0, 1 or 2;

$R_1$ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; or two substituents represented by $R_1$ are taken together to form a $C_1$-$C_3$alkylene bridge or a fused or spiro 3- to 7-membered carbocyclic or heterocyclic ring; and Each $R_5$ is independently hydrogen, $C_1$-$C_6$alkyl, $C_3$-$C_7$cycloalkyl or phenyl; or two $R_5$ are taken together to form a $C_3$-$C_8$cycloalkyl.

18. A compound or salt thereof according to claim 17, wherein the compound has the formula:

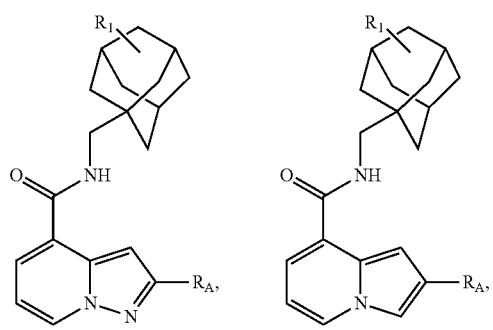

-continued

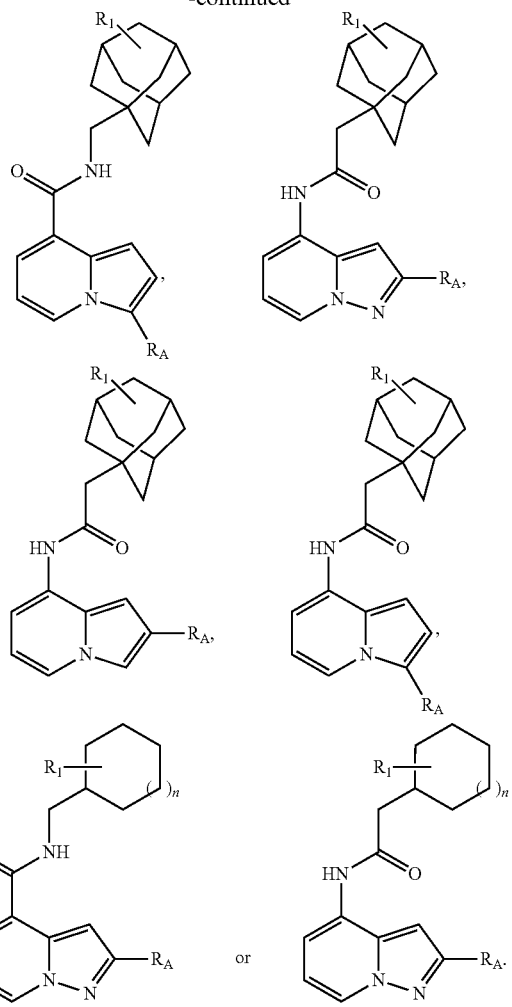

19. A compound or salt thereof according to claim 17, wherein the compound has the formula:

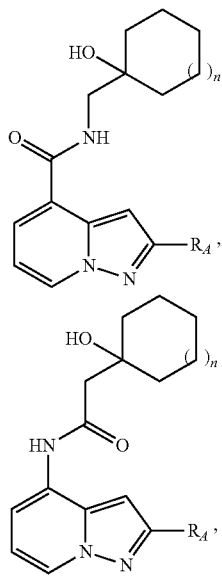

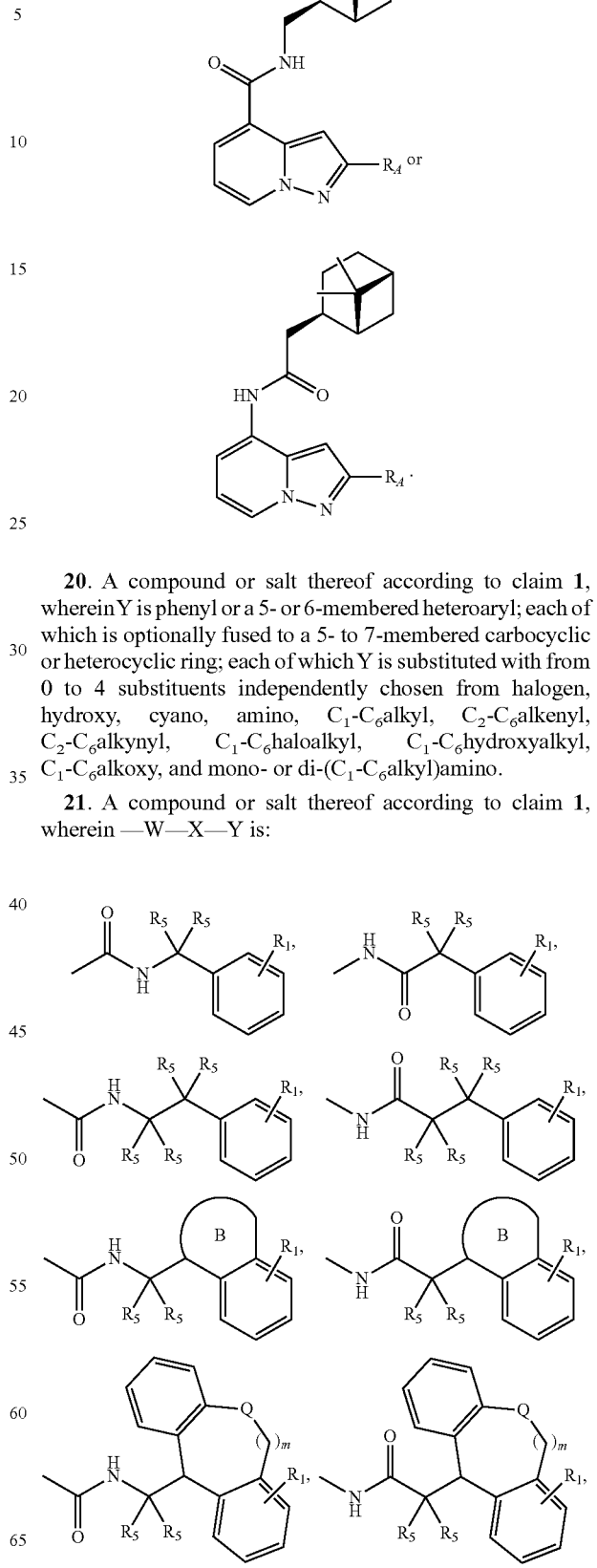

20. A compound or salt thereof according to claim 1, wherein Y is phenyl or a 5- or 6-membered heteroaryl; each of which is optionally fused to a 5- to 7-membered carbocyclic or heterocyclic ring; each of which Y is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino.

21. A compound or salt thereof according to claim 1, wherein —W—X—Y is:

-continued

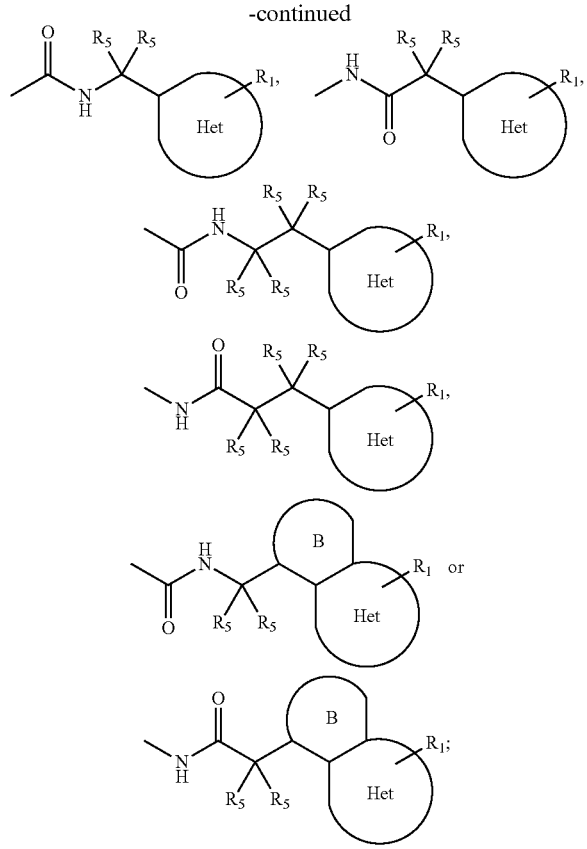

wherein:

is a 5- to 7-membered carbocyclic or heterocyclic ring;

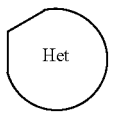

is a 5- or 6-membered heteroaryl;

R₁ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; or two substituents represented by R₁ are taken together to form a fused or spiro 3- to 7-membered carbocyclic or heterocyclic ring;

Each R₅ is independently hydrogen, $C_1$-$C_6$alkyl, $C_3$-$C_7$cycloalkyl or phenyl; or two R₅ are taken together to form a $C_3$-$C_8$cycloalkyl;

Q is $CH_2$, CO, O, NH, S, SO or $SO_2$; and m is 0 or 1.

22. A compound or salt thereof according to claim 1, wherein the compound has the formula:

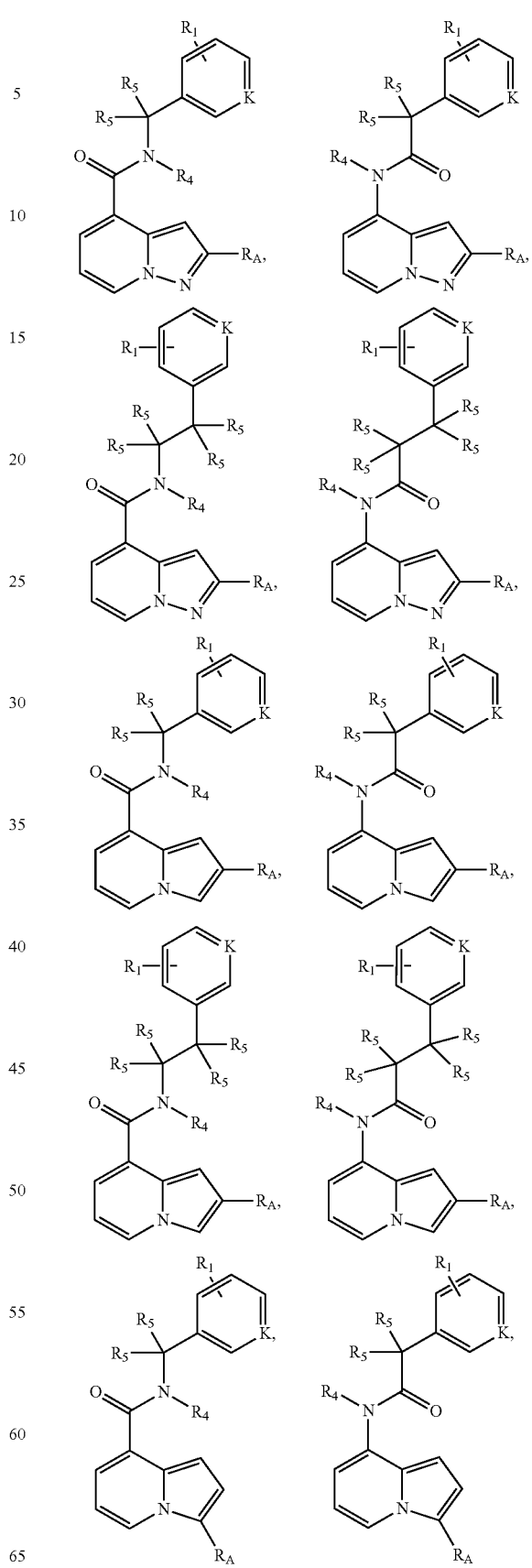

-continued

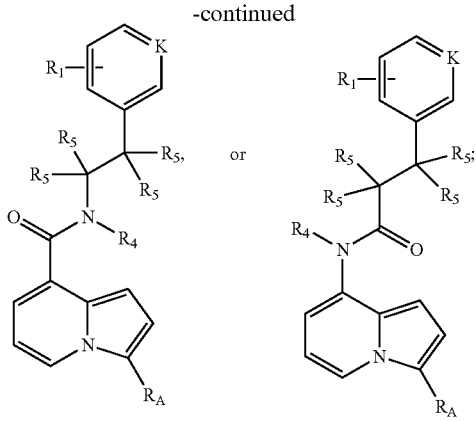

wherein K is CH or N,

R₁ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; or two substituents represented by R₁ are taken together to form a fused or spiro 3- to 7-membered carbocyclic or heterocyclic ring;

R₄ is hydrogen, $C_1$-$C_6$alkyl, ($C_3$-$C_8$cycloalkyl)$C_0$-$C_2$alkyl or taken together with any R₅ to form a 4- to 6-membered heterocycloalkyl;

Each R₅ is independently hydrogen, $C_1$-$C_6$alkyl, $C_3$-$C_7$cycloalkyl or phenyl; or is joined with R₄ to form a 4- to 6-membered heterocycloalkyl; or two R₅ are taken together to form a $C_3$-$C_8$cycloalkyl;

and R_A is a group of the formula -L-A-M, wherein:
L is absent or $C_1$-$C_6$alkylene that is optionally modified by the replacement of a carbon-carbon single bond with a double or triple carbon-carbon bond, which alkylene is optionally substituted with oxo, —COOH, —SO₃H, —SO₂NH₂, —POH₂, tetrazole or oxadiazolone;

A is absent or CO, O, NR₆, S, SO, SO₂, CONR₆, NR₆CO, ($C_4$-$C_7$cycloalkyl)$C_0$-$C_4$alkylene or (4- to 7-membered heterocycloalkyl)$C_0$-$C_4$alkylene; wherein R₆ is hydrogen or $C_1$-$C_6$alkyl; and M is:
(i) hydroxy, cyano, amino, aminocarbonyl, aminosulfonyl or COOH; or
(ii) $C_1$-$C_6$haloalkyl, $C_1$-$C_6$alkoxy, 5- to 10-membered carbocycle, 4- to 10-membered heterocycle, $C_1$-$C_6$alkanoyloxy, $C_1$-$C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is optionally substituted and each of which is preferably substituted with from 0 to 4 substituents independently chosen from oxo, amino, halogen, hydroxy, cyano, aminocarbonyl, aminosulfonyl, COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

23. A compound or salt thereof according to claim 1, wherein the compound is:
4-[(adamantan-1-ylmethyl)carbamoyl]pyrazolo[1,5-a]pyridine-2-carboxylic acid ethyl ester
N-(adamantan-1-ylmethyl)-2-{[(3R)-3-aminopyrrolidin-1-yl]carbonyl}pyrazolo[1,5-a]pyridine-4-carboxamide;
N-(adamantan-1-ylmethyl)-2-(hydroxymethyl)pyrazolo[1,5-a]pyridine-4-carboxamide;
N-(adamantan-1-ylmethyl)-2-{[(3R)-3-aminopyrrolidin-1-yl]methyl}pyrazolo[1,5-a]pyridine-4-carboxamide;
N-(adamantan-1-ylmethyl)-2-(cyanomethyl)pyrazolo[1,5-a]pyridine-4-carboxamide;
{4-[(adamantan-1-ylmethyl)carbamoyl]pyrazolo[1,5a]pyridin-2-yl}acetic acid;
N-(adamantan-1-ylmethyl)-2-{2-[(3R)-3-aminopiperidin-1-yl]-2-oxoethyl}pyrazolo[1,5-a]pyridine-4-carboxamide;
{4-[(adamantan-1-ylmethyl)carbamoyl]pyrazolo[1,5-a]pyridin-2-ylmethoxy}acetic acid ethyl ester;
{4-[(adamantan-1-ylmethyl)carbamoyl]pyrazolo[1,5-a]pyridin-2-ylmethoxy}acetic acid;
4-(2-adamantan-1-ylacetylamino)pyrazolo[1,5-a]pyridine-2-carboxylic acid ethyl ester;
2-(2-cyano-vinyl)-pyrazolo[1,5-a]pyridine-4-carboxylic acid (adamantan-1-ylmethyl)-amide;
N-(adamantan-1-ylmethyl)-2-(2-cyanoethyl)pyrazolo[1,5-a]pyridine-4-carboxamide;
2-[2-(1H-tetrazol-5yl)-ethyl]-pyrazolo[1,5-a]pyridine-4-carboxylic acid (adamantan-1-ylmethyl)-amide;
N-(adamantan-1-ylmethyl)-2-{[(3R)-3-(isopropylamino)pyrrolidin-1yl]carbonyl}pyrazolo[1,5-a]pyridine-4-carboxamide;
N-(adamantan-1-ylmethyl)-2-{[(3R)-3-aminopiperidin-1-yl]carbonyl}pyrazolo[1,5-a]pyridine-4-carboxamide;
4-N-(adamantan-1-ylmethyl)-2-N-(2-methoxyethyl)-2-N-methylpyrazolo[1,5-a]pyridine-2,4-dicarboxamide,
4-N-(adamantan-1-ylmethyl)-2-N-methyl-2-N-pyridin-2-ylpyrazolo[1,5-a]pyridine-2,4-dicarboxamide;
N-(adamantan-1-ylmethyl)-2-(5,6-dihydroimidazo[1,5-a]pyrazin-7(8H)-ylcarbonyl)pyrazolo[1,5-a]pyridine-4-carboxamide;
4-N-(adamantan-1-ylmethyl)-2-N-methyl-2-N-(pyridin-3-ylmethyl)pyrazolo[1,5-a]pyridine-2,4-dicarboxamide;
N-(adamantan-1-ylmethyl)-2-(morpholin-4-ylcarbonyl)pyrazolo[1,5-a]pyridine-4-carboxamide;
ethyl N-({4-[(adamantan-1ylmethyl)carbamoyl]pyrazolo[1,5-a]pyridin-2-yl}carbonyl)-N-methylglycinate;
N-(adamantan-1-ylmethyl)-2-(5,6-dihydro[1,2,4]triazolo[4,3-a]pyrazin-7(8H)-ylcarbonyl)pyrazolo[1,5-a]pyridine-4-carboxamide;
N-(adamantan-1-ylmethyl)-2-(2-morpholin-4-yl-2-oxoethyl)pyrazolo[1,5-a]pyridine-4-carboxamide;
4-N-(adamantan-1-ylmethyl)-2-N-methyl-2-N-[(1-methyl-1H-imidazol-5-yl)methyl]pyrazolo[1,5-a]pyridine-2,4-dicarboxamide;
N-(adamantan-1-ylmethyl)-2-{[(3R)-3-(dimethylamino)pyrrolidin-1-yl]carbonyl}pyrazolo[1,5-a]pyridine-4-carboxamide;
4-N-(adamantan-1-ylmethyl)-2-N-methyl-2-N-(tetrahydrofuran-3-yl)pyrazolo[1,5-a]pyridine-2,4-dicarboxamide;

ethyl N-({4-[(adamantan-1-ylmethyl)carbamoyl]pyrazolo[1,5-a]pyridin-2-yl}methyl)-N-methylglycinate;
N-(adamantan-1-ylmethyl)-2-[(2-methyl-4-oxo-3,5,7,8-tetrahydropyrido[4,3-d]pyrimidin-6(4H)-yl)carbonyl]pyrazolo[1,5-a]pyridine-4-carboxamide;
N-(adamantan-1-ylmethyl)-2-{[(3R)-3-(diethylamino)pyrrolidin-1-yl]carbonyl}pyrazolo[1,5-a]pyridine-4-carboxamide;
N-(adamantan-1-ylmethyl)-2-[(3-oxopiperazin-1-yl)carbonyl]pyrazolo[1,5-a]pyridine-4-carboxamide;
4-N-adamantan-1-ylmethyl)-2-N-methyl-2-N-(pyridin-4-ylmethyl)pyrazolo[1,5-a]pyridine-2,4-dicarboxamide;
N-(adamantan-1-ylmethyl)-2-[(1-methyl-1,4,6,7-tetrahydro-5H-pyrazolo[4,3-c]pyridin-5-yl)carbonyl]pyrazolo[1,5-a]pyridine-4-carboxamide;
4-N-(adamantan-1-ylmethyl)-2-N-(tetrahydro-2H-pyran-4-yl)pyrazolo[1,5-a]pyridine-2,4-dicarboxamide;
N-(adamantan-1-ylmethyl)-2-[(2-oxo-1-oxa-3,8-diazaspiro[4,5]dec-8-yl)carbonyl]pyrazolo[1,5-a]pyridine-4-carboxamide;
4-N-(adamantan-1-ylmethyl)-2-N-methyl-2-N-(tetrahydro-2H-pyran-4-yl)pyrazolo[1,5-a]pyridine-2,4-dicarboxamide;
4-N-(adamantan-1-ylmethyl)-2-N-(3-methoxypropyl)pyrazolo[1,5-a]pyridine-2,4-dicarboxamide;
4-N-(adamantan-1-ylmethyl)-2-N-methyl-2-N-pyridin-4-ylpyrazolo[1,5-a]pyridine-2,4-dicarboxamide;
N-(adamantan-1-ylmethyl)-2-[(3-oxo-2,8-diazaspiro[4.5]dec-8-yl)carbonyl]pyrazolo[1,5-a]pyridine-4-carboxamide;
ethyl N-({4-[(adamantan-1-ylmethyl)carbamoyl]pyrazolo[1,5-a]pyridin-2-yl}carbonyl)glycinate;
4-N-(adamantan-1-ylmethyl)-2-N-(2-methoxyethyl)pyrazolo[1,5-a]pyridine-2,4-dicarboxamide;
2-{[(3R)-3-aminopiperidin-1-yl]carbonyl}-N-(4-methyl-2-phenylpentyl)pyrazolo[1,5-a]pyridine-4-carboxamide;
N-(adamantan-1-ylmethyl)-2-[2-(1H-tetrazol-5-yl)ethyl]pyrazolo[1,5-a]pyridine-4-carboxamide;
tert-butyl[1-({4-[(4-methyl-2-phenylpentyl)carbamoyl]pyrazolo[1,5-a]pyridin-2-yl}carbonyl)pyrrolidin-3-yl]carbamate;
2-{[(3R)-3-aminopyrrolidin-1-yl]carbonyl}-N-(4-methyl-2-phenylpentyl)pyrazolo[1,5-a]pyridine-4-carboxamide;
N-(adamantan-1-ylmethyl)-2-{[(3R)-3-methylamino)pyrrolidin-1-yl]carbonyl}pyrazolo[1,5-a]pyridine-4-carboxamide;
N-(adamantan-1-ylmethyl)-2-{[(3R)-3-(ethylamino)pyrrolidin-1-yl]carbonyl}pyrazolo[1,5-a]pyridine-4-carboxamide;
4-N-(adamantan-1-ylmethyl)-2-N-methyl-2-N-(pyrazin-2-ylmethyl)pyrazolo[1,5-a]pyridine-2,4-dicarboxamide;
4-N-(adamantan-1-ylmethyl)-2-N-methyl-2-N-[(1-methyl-1H-pyrazol-4-yl)methylpyrazolo[1,5-a]pyridine-2,4-dicarboxamide;
4-N-(adamantan-1-ylmethyl)-2-N-methyl-2-N-pyridin-2-ylmethyl)pyrazolo[1,5-a]pyridine-2,4-dicarboxamide;
4-N-(adamantan-1-ylmethyl)-2-N-(pyridin-2-ylmethyl)pyrazolo[1,5-a]pyridine-2,4-dicarboxamide;
N-(adamantan-1-ylmethyl)-2-(5,6-dihydroimidazo[1,5-a]pyrazin-7(8H)-ylmethyl)pyrazolo[1,5-a]pyridine-4-carboxamide;
N-(adamantan-1-ylmethyl)-2-{[methyl(pyridin-2-ylmethyl)amino]methyl}pyrazolo[1,5-a]pyridine-4-carboxamide;
N-(adamantan-1-ylmethyl)-2-{[methyl(pyridin-3-ylmethyl)amino]methyl}pyrazolo[1,5-a]pyridine-4-carboxamide;
N-(adamantan-1-ylmethyl)-2-{[methyl(pyrazin-2-ylmethyl)amino]methyl}pyrazolo[1,5-a]pyridine-4-carboxamide;
2-{[(3R)-3-aminopyrrolidin-1-yl]carbonyl}-N-(4-methyl-2-pyridin-3-ylpentyl)pyrazolo[1,5-a]pyridine-4-carboxamide;
2-{[(3R)-3-aminopyrrolidin-1-yl]carbonyl}-N-(1-pyridin-3-ylcyclohexyl)methylpyrazolo[1,5-a]pyridine-4-carboxamide;
2-{[(3R)-3-aminopyrrolidin-1-yl]carbonyl}-N-(2-cyclohexyl-4-methylpentyl)pyrazolo[1,5-a]pyridine-4-carboxamide;
N-(adamantan-1-ylmethyl)-2-{2-[(2-fluoroethyl)amino]-2-oxoethyl}pyrazolo[1,5-a]pyridine-4-carboxamide;
N-(adamantan-1-ylmethyl)-2-{2-[(2,2-difluoroethyl)amino]-2-oxoethyl}pyrazolo[1,5-a]pyridine-4-carboxamide;
N-(adamantan-1-ylmethyl)-2-{2-oxo-2-[(2,2,2-trifluoroethyl)amino]ethyl}pyrazolo[1,5-a]pyridine-4-carboxamide;
4-N-(adamantan-1-ylmethyl)-2-N-(2-fluoroethyl)pyrazolo[1,5-a]pyridine-2,4-dicarboxamide;
4-N-(adamantan-1-ylmethyl)-2-N-2,2-difluoroethyl)pyrazolo[1,5-a]pyridine-2,4-dicarboxamide;
4-N-(adamantan-1-ylmethyl)-2-N-(2,2,2-trifluoroethyl)pyrazolo[1,5-a]pyridine-2,4-dicarboxamide;
4-N-(adamantan-1-ylmethyl)-2-N-(2-fluorobenzyl)-2-N-methylpyrazolo[1,5-a]pyridine-2,4-dicarboxamide;
4-N-(adamantan-1-ylmethyl)-2-N-(3-fluorobenzyl)-2-N-methylpyrazolo[1,5-a]pyridine-2,4-dicarboxamide;
4-N-(adamantan-1-ylmethyl)-2-N-(4-fluorobenzyl)-2-N-methylpyrazolo[1,5-a]pyridine-2,4-dicarboxamide;
N-(adamantan-1-ylmethyl)-2-{[(2-fluorobenzyl)(methyl)amino]methyl}pyrazolo[1,5-a]pyridine-4-carboxamide;
N-(adamantan-1-ylmethyl)-2-{[(3-fluorobenzyl)(methyl)amino]methyl}pyrazolo[1,5-a]pyridine-4-carboxamide;
N-(adamantan-1-ylmethyl)-2-{[(4-fluorobenzyl)(methyl)amino]methyl}pyrazolo[1,5-a]pyridine-4-carboxamide;
2-{[(3R)-3-aminopyrrolidin-1-yl]carbonyl}-N-[2-(4-chlorophenyl)-4-methylpentyl]pyrazolo[1,5-a]pyridine-4-carboxamide;
2-{[(3R)-3-aminopyrrolidin-1-yl]carbonyl}-N-(3-cyclohexyl-2-phenylpropyl)pyrazolo[1,5-a]pyridine-4-carboxamide;
2-{[(3R)-3-aminopyrrolidin-1-yl]carbonyl}-N-[4-methyl-2-(4-methylphenyl)pentyl]pyrazolo[1,5-a]pyridine-4-carboxamide;
4-N-adamantan-1-ylmethyl)-2-N-(2-fluoroethyl)-2-N-methylpyrazolo[1,5-a]pyridine-2,4-dicarboxamide;
4-N-(adamantan-1-ylmethyl)-2-N-(2,2-difluoroethyl)-2-N-methylpyrazolo[1,5-a]pyridine-2,4-dicarboxamide;
4-N-(adamantan-1-ylmethyl)-2-N-methyl-2-N-(2,2,2-trifluoroethyl)pyrazolo[1,5-a]pyridine-2,4-dicarboxamide;
N-(adamantan-1-ylmethyl)-2-{2-[(2-fluoroethyl)(methyl)amino]-2-oxoethyl}pyrazolo[1,5-a]pyridine-4-carboxamide;
N-(adamantan-1-ylmethyl)-2-{2-[(2,2-difluoroethyl)(methyl)amino]-2-oxoethyl}pyrazolo[1,5-a]pyridine-4-carboxamide;

N-(adamantan-1-ylmethyl)-2-{2-[methyl(2,2,2-trifluoro-ethyl)amino]-2-oxoethyl}pyrazolo[1,5-a]pyridine-4-carboxamide;
2-{[(3R)-3-aminopyrrolidin-1-yl]carbonyl}-N-{4-methyl-2-[4-(trifluoromethyl)phenyl]pentyl}pyrazolo[1,5-a]pyridine-4-carboxamide:
4-N-(adamantan-1-ylmethyl)-2-N-methyl-2-N-[2-(methylsulfonyl)ethyl]pyrazolo[1,5-a]pyridine-2,4-dicarboxamide;
4-N-(adamantan-1-ylmethyl)-2-N-(1,1-dioxidotetrahydrothiophen-3-yl)pyrazolo[1,5-a]pyridine-2,4-dicarboxamide;
N-{[1-(4-chlorophenyl)cyclohexyl]methyl}-2-(5,6-dihydroimidazo[1,5-a]pyrazin-7(8H)-ylcarbonyl)pyrazolo[1,5-a]pyridine-4-carboxamide;
N-{[1-(4-chlorophenyl)cyclohexyl]methyl}-2-(morpholin-4-ylcarbonyl)pyrazolo[1,5-a]pyridine-4-carboxamide;
4-N-{[1-(4-chlorophenyl)cyclohexyl]methyl}-2-N-(2-fluoroethyl)-2-N-methylpyrazolo[1,5-a]pyridine-2,4-dicarboxamide;
2-N-(2-fluoroethyl)-2-N-methyl-4-N-{4-methyl-2-[4-(trifluoromethyl)phenyl]pentyl}pyrazolo[1,5-a]pyridine-2,4-dicarboxamide;
N-{4-methyl-2-[4-(trifluoromethyl)phenyl]pentyl}-2-(morpholin-4-ylcarbonyl)pyrazolo[1,5-a]pyridine-4-carboxamide;
2-(5,6-dihydroimidazo[1,5-a]pyrazin-7(8H)-ylcarbonyl)-N-{4-methyl-2-[4-(trifluoromethyl)phenyl]pentyl}pyrazolo[1,5-a]pyridine-4-carboxamide;
N-(adamantan-1-ylmethyl)-2-(4,5-dihydro-1H-imidazol-2-ylmethyl)pyrazolo[1,5-a]pyridine-4-carboxamide;
2-{[(3R)-3-aminopyrrolidin-1-yl]carbonyl}-N-{[1-(4-chlorophenyl)cyclohexyl]methyl}pyrazolo[1,5-a]pyridine-4-carboxamide;
N-[2-(4-chlorophenyl)-4-methylpentyl]-2-(morpholin-4-ylcarbonyl)pyrazolo[1,5-a]pyridine-4-carboxamide;
Pyrazolo[1,5-a]pyridine-2,4-dicarboxylic acid 4-{[2-(4-chloro-phenyl)-4-methyl-pentyl]-amide}2-[(2-fluoro-ethyl)-methyl-amide];
Pyrazolo[1,5-a]pyridine-2,4-dicarboxylic acid 2-[(2-fluoro-ethyl)-methyl-amide]-4-{[1-(4-trifluoromethyl-phenyl)-cyclohexylmethyl]-amide};
2-(morpholin-4-ylcarbonyl)-N-({1-[4-trifluoromethyl)phenyl]cyclohexyl}methyl)pyrazolo[1,5-a]pyridine-4-carboxamide;
N-(adamantan-1-ylmethyl)-2-[2-(4,5-dihydro-1H-imidazol-2-yl)ethyl]pyrazolo[1,5-a]pyridine-4-carboxamide;
2-adamantan-1-yl-N-[2-(morpholin-4-ylcarbonyl)pyrazolo[1,5-a]pyridin-4-yl]acetamide;
2-adamantan-1-yl-N-[2-(5,6-dihydroimidazo[1,5-a]pyrazin-7(8H)-ylcarbonyl)pyrazolo[1,5-a]pyridin-4-yl]acetamide;
4-[(adamantan-1-ylacetyl)amino]-N-(2-fluoroethyl)-N-methylpyrazolo[1,5-a]pyridine-2-carboxamide;
2-adamantan-1-yl-N-(2-{[(3R)-3-aminopyrrolidin-1-yl]carbonyl}pyrazolo[1,5-a]pyridin-4-yl)acetamide;
rel-2-{[(2R,6S)-2,6-dimethylmorpholin-4-yl]carbonyl}-N-{4-methyl-2-[4-(trifluoromethyl)phenyl]pentyl}pyrazolo[1,5-a]pyridine-4-carboxamide;
2-[(2,2-dimethylmorpholin-4-yl)carbonyl]-N-{4-methyl-2-[4-(trifluoromethyl)phenyl]pentyl}pyrazolo[1,5-a]pyridine-4-carboxamide;
rel-2-{[(3R,5S)-3,5-dimethylmorpholin-4-yl]carbonyl}-N-{4-methyl-2-[4-(trifluoromethyl)phenyl]pentyl}pyrazolo[1,5-a]pyridine-4-carboxamide;
2-{4-[(adamantan-1-ylmethyl)carbamoyl]pyrazolo[1,5-a]pyridin-2-yl}-3-phenylpropanoic acid;
2-[4-({[1-(4-chlorophenyl)cyclohexyl]methyl}carbamoyl)pyrazolo[1,5-a]pyridin-2-yl]-3-phenylpropanoic acid;
3-{4-[(adamantan-1-ylmethyl)carbamoyl]pyrazolo[1,5-a]pyridin-2-yl}butanoic acid;
3-{4-[(adamantan-1-ylmethyl)carbamoyl]pyrazolo[1,5-a]pyridin-2-yl}-3-phenylpropanoic acid
3-{4-[(adamantan-1-ylmethyl)carbamoyl]pyrazolo[1,5-a]pyridin-2-yl}-4-phenylbutanoic acid;
4-{8-[(adamantan-1-ylmethyl)carbamoyl]indolizin-2-yl}benzoic acid;
N-(adamantan-1-ylmethyl)-3-(4-cyanobenzoyl)indolizine-8-carboxamide;
N-(adamantan-1-ylmethyl)-3-(4-carbamoylbenzoyl)indolizine-8-carboxamide;
2-(4-cyanophenyl)-N-[(1-pyridin-3-ylcyclohexyl)methyl]indolizine-8-carboxamide;
N-(adamantan-1-ylmethyl)-3-(3-cyanobenzoyl)indolizine-8-carboxamide;
N-(adamantan-1-ylmethyl)-3-(3-carbamoylbenzoyl)indolizine-8-carboxamide; or
N-(adamantan-1-ylmethyl)-2-(4-carbamoylphenyl)indolizine-8-carboxamide.

24. A pharmaceutical composition, comprising at least one compound or salt thereof according to claim 1 in combination with a physiologically acceptable carrier or excipient.

25. The pharmaceutical composition according to claim 24, wherein the composition is formulated as an injectible fluid, an aerosol, a cream, an ointment, an oral liquid, a tablet, a troche, a lozenge a sprinkle, a powder, a dispersible powder, granules, a pill, a capsule, a gel, a paste, a foam, a lotion, an aqueous liquid, an emulsion, a syrup, a suppository or a transdermal patch.

26. A packaged pharmaceutical preparation, comprising:
(a) a pharmaceutical composition according to claim 24 in a container; and
(b) instructions for using the composition to treat pain.

* * * * *